US012617779B2

(12) United States Patent
Kamioka et al.

(10) Patent No.: US 12,617,779 B2
(45) Date of Patent: May 5, 2026

(54) SELF DEGRADATION-TYPE CDK9 INHIBITOR PRODRUG AND LIPOSOME ENCAPSULATING SAME

(71) Applicant: Sumitomo Pharma Co., Ltd., Osaka (JP)

(72) Inventors: Seiji Kamioka, Osaka (JP); Naoaki Shimada, Osaka (JP); Makoto Matsuoka, Osaka (JP); Hitoshi Ban, Osaka (JP)

(73) Assignee: Sumitomo Pharma Co., Ltd., Osaka (JP)

( * ) Notice: Subject to any disclaimer, the term of this patent is extended or adjusted under 35 U.S.C. 154(b) by 108 days.

(21) Appl. No.: 18/685,618

(22) PCT Filed: Aug. 22, 2022

(86) PCT No.: PCT/JP2022/031584

§ 371 (c)(1),
(2) Date: Feb. 22, 2024

(87) PCT Pub. No.: WO2023/027032

PCT Pub. Date: Mar. 2, 2023

(65) Prior Publication Data

US 2024/0368138 A1 Nov. 7, 2024

(30) Foreign Application Priority Data

Aug. 23, 2021 (JP) ................................ 2021-135603

(51) Int. Cl.

| | |
|---|---|
| ***C07D 405/14*** | (2006.01) |
| ***A61K 9/1271*** | (2025.01) |
| ***A61K 31/4545*** | (2006.01) |
| ***A61K 31/5377*** | (2006.01) |
| ***A61P 35/00*** | (2006.01) |
| ***C07D 413/14*** | (2006.01) |

(52) U.S. Cl.

CPC .......... *C07D 405/14* (2013.01); *A61K 9/1271* (2013.01); *A61K 31/4545* (2013.01); *A61K 31/5377* (2013.01); *A61P 35/00* (2018.01); *C07D 413/14* (2013.01)

(58) Field of Classification Search

CPC .. C07D 405/14; C07D 412/14; A61K 9/1271; A61K 31/4545; A61K 31/5377; A61P 35/00

See application file for complete search history.

(56) References Cited

U.S. PATENT DOCUMENTS

| | | | |
|---|---|---|---|
| 6,352,996 | B1 | 3/2002 | Cao et al. |
| 2020/0048228 | A1 | 2/2020 | Siddiqui-Jain et al. |
| 2020/0207782 | A1 | 7/2020 | Kamioka et al. |
| 2021/0253626 | A1 | 8/2021 | Purohit et al. |

FOREIGN PATENT DOCUMENTS

| | | | |
|---|---|---|---|
| CN | 106866733 | A | 6/2017 |
| WO | WO 2016/187316 | A1 | 11/2016 |
| WO | WO 2018/094275 | A1 | 5/2018 |
| WO | WO 2019/059344 | A1 | 3/2019 |
| WO | WO 2019/224790 | A2 | 11/2019 |
| WO | WO 2021/172359 | A1 | 9/2021 |

OTHER PUBLICATIONS

International Search Report issued Oct. 25, 2022 in PCT/JP2022/031584, filed on Aug. 22, 2022, 2 pages.
International Search Report issued Oct. 25, 2022, in PCT/JP2022/031584, 2 pages.
Suoping Zhai et al., "Flavopiridol, a Novel Cyclin-Dependent Kinase Inhibitor, in Clinical Development", The Annals of Pharmacotherapy 36: 905-911. (2002) and cover page.

(Continued)

*Primary Examiner* — Trevor Love

(74) *Attorney, Agent, or Firm* — Hamilton, Brook, Smith & Reynolds, P.C.

(57) ABSTRACT

Provided is a self-degradation type CDK9 inhibitor prodrug and a liposome encapsulating the same. The present disclosure provides a compound represented by formula (1) or a pharmaceutically acceptable salt thereof:

(1)

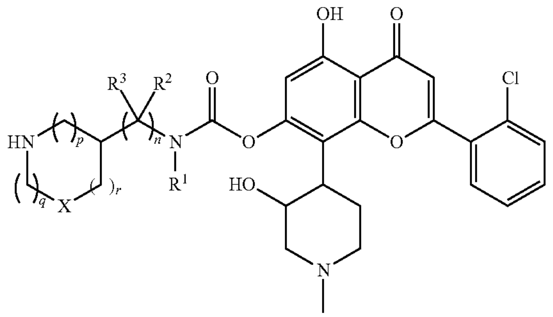

wherein $R^1$ is an optionally substituted $C_{1-6}$ alkyl group, $R^2$ and $R^3$ are the same or different, each independently a hydrogen atom or an optionally substituted $C_{1-6}$ alkyl group, X is $CH_2$ or an oxygen atom, n is 1 or 2, p is 0, 1 or 2, q is 1 or 2, and r is 0, 1 or 2, wherein, if X is an oxygen atom, q is 2.

33 Claims, No Drawings

(56) References Cited

OTHER PUBLICATIONS

Atiar M. Rahman et al., “Anthracycline-induced cardiotoxicity and the cardiac-sparing effect of liposomal formulation”, International Journal of Nanomedicine 2(4): 567-583. (2007) and cover page.
Yechezkel (Chezy) Barenholz, “Doxil®—The first FDA-approved nano-drug: Lessons learned”, Journal of Controlled Release 160: 117-134. (2012).
Xiaojuan Yang et al., “A novel liposomal formulation of flavopiridol”, International Journal of Pharmaceutics 365; 170-174. (2009), pp. 1-16.

SELF DEGRADATION-TYPE CDK9 INHIBITOR PRODRUG AND LIPOSOME ENCAPSULATING SAME

TECHNICAL FIELD

The present disclosure relates to prodrugs of the CDK9 inhibitor Alvocidib, pharmaceutically acceptable salts thereof, or hydrates or solvates thereof. The present disclosure also relates to pharmaceutical compositions comprising the same, and the like.

BACKGROUND ART

Cyclin-dependent kinases (CDKs) are important regulatory factors that regulate cell cycle progression and the like, and selective CDK inhibitors are useful chemotherapeutic agents.

Alvocidib (flavopiridol) is a synthetic flavone having the following structure:

[Chemical Formula 5]

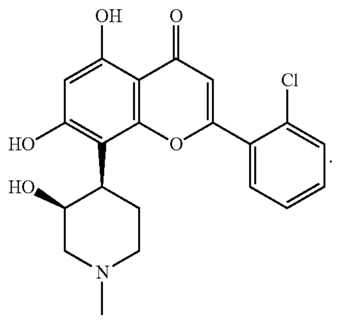

Alvocidib is a potent and selective inhibitor of CDK, has anti-tumor activity against various tumor cell lines, including human lung cancer and breast cancer, and inhibits tumor growth in tumor-bearing mouse models. Alvocidib inhibits polymerase II-driven transcription through CDK9 inhibition. Treatment with Alvocidib inhibits positive transcription elongation factors, or CDK9, which forms part of a complex known as P-TEFb, and decreases the expression of important oncogenes such as MYC and important anti-apoptotic proteins such as MCL1. Therefore, Alvocidib is an attractive cancer therapeutic agent, and is currently in clinical development for use in blood cancers.

On the other hand, while Alvocidib has excellent pharmacological activity, it has been reported to cause many side effects such as diarrhea and neutropenia in clinical trials, which may limit its clinical application. In clinical trials to date, long-term intravenous administration of Alvocidib (for example, 24-hour or 72-hour continuous administration) has been investigated with the aim of reducing side effects, but no clear improvement in side effects has been achieved (Non-Patent Document 1).

CITATION LIST

Patent Documents

[Patent Document 1]: WO 2016/187316
[Patent Document 2]: WO 2018/094275
[Patent Document 3]: WO 2019/059344

Non-Patent Documents

[Non-Patent Document 1]: Suoping Zhai et al. The Annals of Pharmacotherapy 36: 905-911. (2002)

[Non-Patent Document 2]: Atiar M. Rahman et al. International Journal of Nanomedicine 2(4): 567-583. (2007)

[Non-Patent Document 3]: Yechezkel (Chezy) Barenholz. Journal of Controlled Release 160: 117-134. (2012)

[Non-Patent Document 4]: Xiaojuan Yang et al. International Journal of Pharmaceutics 365; 170-174. (2009)

SUMMARY OF THE INVENTION

Means of Solving the Problems

The present disclosure provides Alvocidib derivatives as having excellent pharmacological activity. The Alvocidib derivatives of the present disclosure have anti-tumor activity. The Alvocidib derivatives of the present disclosure do not have side effects that limit their clinical application. The Alvocidib derivatives of the present disclosure can be released from liposomes in a sustained release manner. The present disclosure provides Alvocidib prodrugs that are highly efficiently encapsulated in liposomes by a remote loading method, are released from the liposomes in a sustained release manner, and are efficiently converted to Alvocidib in the in vivo environment after release.

In recent years, liposomal formulations in which compounds are encapsulated in liposomes have been used clinically. These liposomal formulations have been reported to alter the biodistribution of compounds and improve their retention in vivo, compared to conventional direct administration of low-molecular-weight compounds (Non-Patent Document 2).

Remote loading methods that utilize the principle of solubility gradient are often used to encapsulate compounds in liposomes. The remote loading method generally has the advantage of being able to encapsulate compounds with high efficiency (Non-Patent Document 3), but in order to use the remote loading method, the compound needs to have high water solubility and exhibit a pH- or ion concentration-dependent solubility gradient. Therefore, the compounds to which the remote loading method is applicable are limited.

It is extremely important if compounds can be encapsulated in liposomes with high efficiency because loss of compounds during the liposome formulation stage will be reduced.

Non-Patent Document 4 discloses that Alvocidib is encapsulated in liposomes by a remote loading method. However, there is no disclosure or suggestion regarding the concentration of the prepared liposome solution. Furthermore, the half-life ($T_{1/2\beta}$) of liposomal Alvocidib in mice is 340 minutes, which is longer than that of Alvocidib alone, but its efficacy is insufficient. Similarly, the AUC of liposomal Alvocidib was only 10.8 min μmol/L compared to Alvocidib alone (3.4 min μmol/L) (both at 2.5 mg/kg administration), which does not show ideal pharmacokinetics.

Patent Document 1 describes the following compound as a phosphate-type prodrug of Alvocidib.

[Chemical Formula 6]

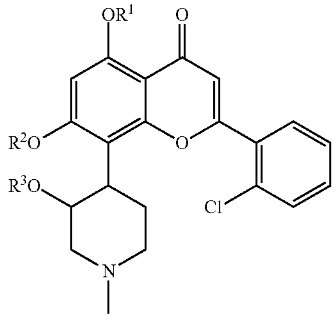

wherein one of $R^1$, $R^2$ and $R^3$ is —P(═O)(OH)$_2$, and the other two are each a hydrogen atom.

Patent Document 2 describes the following compound as a prodrug of Alvocidib.

[Chemical Formula 7]

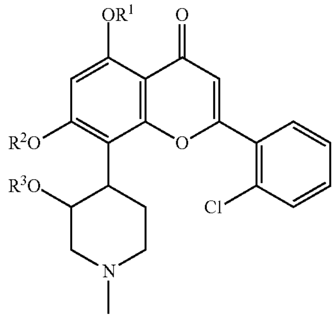

wherein $R^1$, $R^2$ and $R^3$ are independently a hydrogen atom, or —C(═O)$R^a$ or the like, and $R^a$ is an optionally substituted linear $C_{1-12}$ alkyl or the like.

Patent Document 3 describes the following compound as a prodrug of Alvocidib.

[Chemical Formula 8]

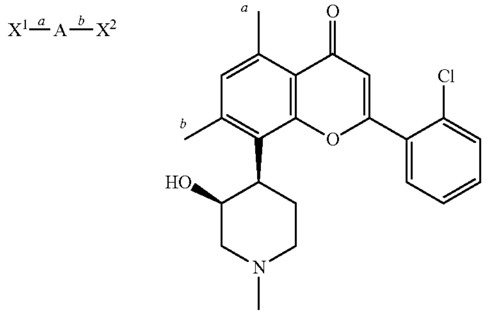

wherein $X^1$ and $X^2$ are the same or different, each independently a hydroxy group, or —O—C(═O)—Y—(C($R^{1A}$) ($R^{1B}$)) n-NH—$R^2$, wherein $X^1$ and $X^2$ are not simultaneously a hydroxyl group, n is 2, 3 or 4, Y is an oxygen atom, or —$NR^4$, $R^{1A}$ and $R^{1B}$ are the same or different, each independently a hydrogen atom or the like, and $R^2$ is a hydrogen atom or the like.

The prodrugs described in Patent Documents 1, 2, and 3 are significantly different from the prodrug of the present invention in the structure of the prodrug moiety. Furthermore, there is no disclosure or suggestion that they are encapsulated in liposomes and exhibit excellent pharmacokinetics.

When attempting to encapsulate Alvocidib in liposomes using a remote loading method based on the findings of Non-Patent Document 4, the present inventors were able to obtain Alvocidib-encapsulated liposomes with high efficiency and high content, but found a new problem in that Alvocidib was unexpectedly immediately released from the liposomes and did not exhibit the sustained-release effect intended in the present disclosure.

The present inventors have conducted intensive studies in an attempt to solve the above-mentioned problem and found that carbamate-type Alvocidib prodrugs, the compounds of formula (1), formula (1'), formula (1A) and formula (1A') in which the substituents on the nitrogen atom in the carbamate are "(1) an alkyl group" and "(2) a methyl group or an ethyl group, which is each substituted with a 4- to 9-membered monocyclic saturated heterocyclic group having one secondary amine in the ring", are rapidly converted to Alvocidib by chemical degradation without any difference between species. Furthermore, the present inventors also found that the Alvocidib prodrug of the present disclosure is efficiently encapsulated in liposomes, has excellent storage stability, and exhibits excellent pharmacokinetics. In addition, the present inventors also found that, when the Alvocidib prodrug-encapsulated liposome formulation of the present disclosure is administered to tumor-bearing mouse models, it has exceptional and heterogeneous effects, that is, it exhibits excellent anti-tumor activity and not cause weight loss as a side effect. These findings resulted in the completion of the present disclosure.

Continuous administration over a long period of time is a burden on patients. However, according to the present disclosure, it is possible to administer in a relatively short period of time, and to change the pharmacokinetics of Alvocidib in vivo, thereby reducing the burden on the patient and reducing side effects. The present disclosure achieves Alvocidib formulations that exhibit such ideal pharmacokinetics and administration methods.

Accordingly, the present disclosure is as follows.

[Item 1]

A compound represented by formula (1):

[Chemical Formula 9]

(1)

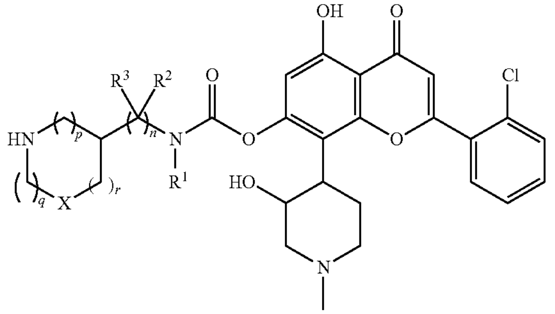

or a pharmaceutically acceptable salt thereof,
wherein $R^1$ is an optionally substituted $C_{1-6}$ alkyl group,
$R^2$ and $R^3$ are the same or different, each independently a hydrogen atom or an optionally substituted $C_{1-6}$ alkyl group,
X is $CH_2$ or an oxygen atom,
n is 1 or 2,
p is 0, 1 or 2,
q is 1 or 2, and
r is 0, 1 or 2,
wherein, if X is an oxygen atom, q is 2.

[Item 2]

The compound or the pharmaceutically acceptable salt thereof of item 1, wherein formula (1) is the following structure represented by formula (1'):

[Chemical Formula 10]

(1')

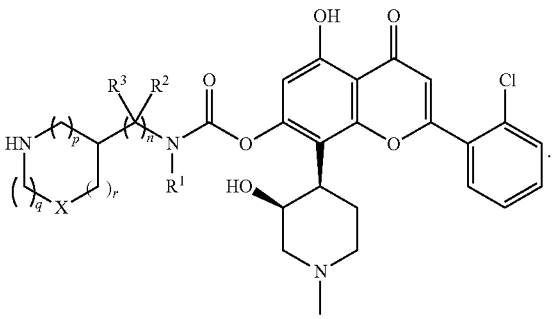

[Item 3]

The compound or the pharmaceutically acceptable salt thereof of item 1 or 2, wherein the substituent of the optionally substituted $C_{1-6}$ alkyl groups in $R^1$, $R^2$, and $R^3$ are each independently a group optionally substituted with 1 to 5 of the same or different substituents selected from the group consisting of:

(1) a halogen atom,
(2) a hydroxyl group,
(3) a carboxyl group,
(4) a sulfinic acid group,
(5) a sulfonic acid group,
(6) a phosphoric acid group,
(7) an optionally substituted $C_{3-8}$ cycloalkyl group,
(8) an optionally substituted $C_{6-10}$ aryl group,
(9) an optionally substituted 5- to 10-membered heteroaryl group,
(10) an optionally substituted $C_{1-6}$ alkoxy group,
(11) an optionally substituted $C_{3-10}$ cycloalkoxy group,
(12) an optionally substituted $C_{1-6}$ alkoxycarbonyl group,
(13) an optionally substituted $C_{1-6}$ alkylcarbonyl group,
(14) an optionally substituted 3- to 10-membered saturated heterocyclic group,
(15) —$NR^4R^5$,
(16) —$CO_2R^4$,
(17) a guanidine group,
(18) —$CONR^4R^5$,
(19) —$SO_2R^4$,
(20) —$SO_2NR^4R^5$, and
(21) cyano, wherein the substituents in (7), (8), (9), (10), (11), (12), (13), and (14) are groups which are optionally substituted with 1 to 5 of the same or different substituents selected from the group consisting of:

(a) a halogen atom,
(b) a hydroxyl group,
(c) a $C_{1-6}$ alkyl group,
(d) a $C_{1-6}$ alkoxy group,
(e) a cyano group,
(f) a carboxyl group,
(g) a sulfinic acid group,
(h) a sulfonic acid group,
(i) a phosphoric acid group,
(j) a $C_{1-6}$ alkoxycarbonyl group,
(k) a $C_{1-6}$ alkylcarbonyl group,
(l) —$NR^4R^5$,
(m) —$CO_2R^4$,
(n) a guanidine group,
(o) —$CONR^4R^5$,
(p) —$SO_2R^4$, and
(q) —$SO_2NR^4R^5$, and $R^4$ and $R^5$ are the same or different hydrogen atoms or $C_{1-10}$ alkyl groups, which are optionally substituted with 1 to 2 substituents selected from the group consisting of a halogen atom and a carboxyl group, wherein $R^4$ and $R^5$, if both are $C_{1-10}$ alkyl groups, together with the nitrogen to which they are attached, may form a 3- to 10-membered nitrogen-containing saturated heterocyclic group.

[Item 4]

The compound or the pharmaceutically acceptable salt thereof of any one of items 1 to 3, wherein the substituent of the optionally substituted $C_{1-6}$ alkyl groups in $R^1$, $R^2$, and $R^3$ are each independently a group optionally substituted with 1 to 5 of the same or different substituents selected from the group consisting of:

(1) a halogen atom,
(2) a hydroxyl group,
(3) a carboxyl group,
(4) a sulfinic acid group,
(5) a sulfonic acid group,
(6) a phosphoric acid group
(7) a $C_{6-10}$ aryl group,
(8) $C_{1-6}$ alkoxy,
(9) —$NR^4R^5$,
(10) —$CO_2R^4$,
(11) —$CONR^4R^5$,
(12) —$SO_2R^4$, and
(13) —$SO_2NR^4R^5$, wherein $R^4$ and $R^5$ are the same or different hydrogen atoms or $C_{1-10}$ alkyl groups, which are optionally substituted with 1 to 2 substituents selected from the group consisting of a halogen atom and a carboxyl group, wherein $R^4$ and $R^5$, if both are $C_{1-10}$ alkyl groups, together with the nitrogen to which they are attached, may form a 3- to 10-membered nitrogen-containing saturated heterocyclic group.

[Item 5]

The compound or the pharmaceutically acceptable salt thereof of any one of items 1 to 4, wherein p is 0 or 1.

[Item 6]

The compound or the pharmaceutically acceptable salt thereof of any one of items 1 to 5, wherein p is 0.

[Item 7]

The compound or the pharmaceutically acceptable salt thereof of any one of items 1 to 6, wherein q is 1.

[Item 8]

The compound or the pharmaceutically acceptable salt thereof of any one of items 1 to 7, wherein r is 2.

[Item 9]

The compound or the pharmaceutically acceptable salt thereof of any one of items 1 to 8, wherein n is 1.

[Item 10]

The compound or the pharmaceutically acceptable salt thereof of any one of items 1 to 9, wherein $R^2$ and $R^3$ are the same or different, each independently (1) a hydrogen atom, or (2) a $C_{1-6}$ alkyl group, which is optionally substituted with 1 to 3 substituents selected from the group consisting of a fluorine atom and $C_{1-6}$ alkoxy.

[Item 11]

The compound or the pharmaceutically acceptable salt thereof of any one of items 1 to 10, wherein $R^2$ and $R^3$ are the same or different, each independently (1) a hydrogen atom, or (2) a $C_{1-6}$ alkyl group optionally substituted with 1 to 3 fluorine atoms.

[Item 12]

The compound or the pharmaceutically acceptable salt thereof of any one of items 1 to 11, wherein $R^2$ and $R^3$ are the same or different, each independently a hydrogen atom or a $C_{1-3}$ alkyl group.

[Item 13]

The compound or the pharmaceutically acceptable salt thereof of any one of items 1 to 12, wherein $R^2$ and $R^3$ are hydrogen atoms.

[Item 14]

The compound or the pharmaceutically acceptable salt thereof of any one of items 1 to 13, wherein X is $CH_2$.

[Item 15]

The compound or the pharmaceutically acceptable salt thereof of items 1 to 14, wherein formula (1) is the following structure represented by formula (1A):

[Chemical Formula 11]

(1A)

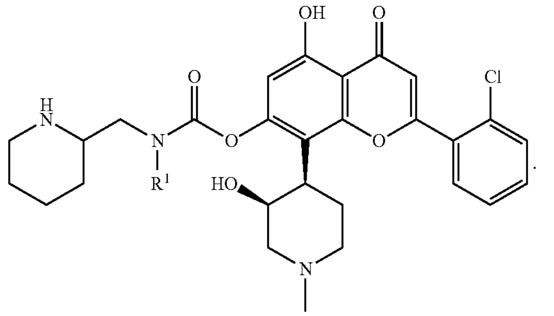

[Item 16]

The compound or the pharmaceutically acceptable salt thereof of item 15, wherein formula (1A) is the following structure represented by formula (1A'):

[Chemical Formula 12]

(1A')

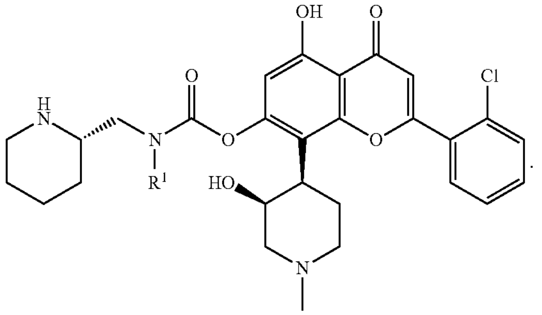

[Item 17]

The compound or the pharmaceutically acceptable salt thereof of any one of items 1 to 16, wherein $R^1$ is a $C_{1-6}$ alkyl group, which is optionally substituted with 1 to 3 substituents selected from the group consisting of a halogen atom, a $C_{6-10}$ aryl group, a hydroxyl group, a carboxyl group, a sulfinic acid group, a sulfonic acid group, a phosphoric acid group, $C_{1-6}$ alkoxy, $—NR^4R^5$, $—CO_2R^4$, $—CONR^4R^5$, $—SO_2R^4$, and $—SO_2NR^4R^5$.

[Item 18]

The compound or the pharmaceutically acceptable salt thereof of any one of items 1 to 17, wherein $R^4$ and $R^5$ are the same or different hydrogen atoms or $C_{1-6}$ alkyl groups, which are optionally substituted with 1 to 2 substituents selected from the group consisting of a fluorine atom and a carboxyl group, wherein $R^4$ and $R^5$, if both are $C_{1-6}$ alkyl groups, together with the nitrogen atom to which they are attached, may form a 3- to 8-membered nitrogen-containing saturated heterocyclic group.

[Item 19]

The compound or the pharmaceutically acceptable salt thereof of any one of items 1 to 18, wherein $R^4$ and $R^5$ are the same or different hydrogen atoms or $C_{1-6}$ alkyl groups.

[Item 20]

The compound or the pharmaceutically acceptable salt thereof of any one of items 1 to 19, wherein $R^1$ is a $C_{1-6}$ alkyl group, which is optionally substituted with 1 to 3 substituents selected from the group consisting of a halogen atom, a phenyl group, $C_{1-6}$ alkoxy, and $—CO_2R^4$.

[Item 21]

The compound or the pharmaceutically acceptable salt thereof of any one of items 1 to 20, wherein $R^1$ is a $C_{1-6}$ alkyl group, which is optionally substituted with 1 to 3 substituents selected from the group consisting of a fluorine atom and $C_{1-6}$ alkoxy.

[Item 22]

The compound or the pharmaceutically acceptable salt thereof of any one of items 1 to 21, wherein $R^1$ is a $C_{1-6}$ alkyl group optionally substituted with 1 to 3 fluorine atoms.

[Item 23]

The compound or the pharmaceutically acceptable salt thereof of any one of items 1 to 22, wherein $R^1$ is a $C_{1-6}$ alkyl group.

[Item 24]

The compound or the pharmaceutically acceptable salt thereof of any one of items 1 to 23, wherein $R^1$ is a methyl group, an ethyl group, or a propyl group.

[Item 25]

The compound or the pharmaceutically acceptable salt thereof of any one of items 1 to 24, wherein $R^1$ is an ethyl group.

[Item 26]

The compound or the pharmaceutically acceptable salt thereof of item 1, which is selected from the following compounds:

2-(2-chlorophenyl)-5-hydroxy-8-[(3S,4R)-3-hydroxy-1-methylpiperidin-4-yl]-4-oxo-4H-1-benzopyran-7-yl ethyl{[(2S)-piperidin-2-yl]methyl}carbamate (Example 1), 2-(2-chlorophenyl)-5-hydroxy-8-[(3S,4R)-3-hydroxy-1-methylpiperidin-4-yl]-4-oxo-4H-1-benzopyran-7-yl ethyl{[(2R)-piperidin-2-yl]methyl}carbamate (Example 2), 2-(2-chlorophenyl)-5-hydroxy-8-[(3S,4R)-3-hydroxy-1-methylpiperidin-4-yl]-4-oxo-4H-1-benzopyran-7-yl methyl{[(2S)-piperidin-2-yl]methyl}carbamate (Example 3), 2-(2-chlorophenyl)-5-hydroxy-8-[(3S,4R)-3-hydroxy-1-methylpiperidin-4-yl]-4-oxo-4H-1-benzopyran-7-yl methyl{[(2R)-piperidin-2-yl]methyl}carbamate (Example 4), 2-(2-chlorophenyl)-5-hydroxy-8-[(3S,4R)-3-hydroxy-1-methylpiperidin-4-yl]-4-oxo-4H-1-benzopyran-7-yl {[(2S)-piperidin-2-yl]methyl}propylcarbamate (Example 5), 2-(2-chlorophenyl)-5-hydroxy-8-[(3S,4R)-3-hydroxy-1-methylpiperidin-4-yl]-4-oxo-4H-1-benzopyran-7-yl {[(2R)-piperidin-2-yl]methyl}propylcarbamate (Example 6), 2-(2-chlorophenyl)-5-hydroxy-8-[(3S,4R)-3-hydroxy-1-methylpiperidin-4-yl]-4-oxo-4H-1-benzopyran-7-yl ethyl [(piperidin-2-yl)methyl]carbamate (Example 7), 2-(2-chlorophenyl)-5-hydroxy-8-[(3S,4R)-3-hydroxy-1-methylpiperidin-4-yl]-4-oxo-4H-1-benzopyran-7-yl methyl[(piperidin-2-yl)methyl]carbamate (Example 8), 2-(2-chlorophenyl)-5-hydroxy-8-[(3S,4R)-3-hydroxy-1-methylpiperidin-4-yl]-4-oxo-4H-1-benzopyran-7-yl [(piperidin-2-yl)methyl]propylcarbamate (Example 9), 2-(2-chlorophenyl)-5-hydroxy-8-[(3S,4R)-3-hydroxy-1-methylpiperidin-4-yl]-4-oxo-4H-1-benzopyran-7-yl [(piperidin-2-yl)methyl]propan-2-ylcarbamate (Example 10), 2-(2-chlorophenyl)-5-hydroxy-8-[(3S,4R)-3-hydroxy-1-methylpiperidin-4-yl]-4-oxo-4H-1-benzopyran-7-yl (2-fluoroethyl) [(piperidin-2-yl)methyl]carbamate (Example 11), 2-(2-chlorophenyl)-5-hydroxy-8-[(3S,4R)-3-hydroxy-1-methylpiperidin-4-yl]-4-oxo-4H-1-benzopyran-7-yl (2-methoxyethyl) [(piperidin-2-yl)methyl]carbamate (Example 12), 2-(2-chlorophenyl)-5-hydroxy-8-[(3S,4R)-3-hydroxy-1-methylpiperidin-4-yl]-4-oxo-4H-1-benzopyran-7-yl [(piperidin-2-yl)methyl](3,3,3-trifluoropropyl)carbamate (Example 13), 2-(2-chlorophenyl)-5-hydroxy-8-[(3S,4R)-3-hydroxy-1-methylpiperidin-4-yl]-4-oxo-4H-1-benzopyran-7-yl [(piperidin-2-yl)methyl](4,4,4-trifluorobutyl)carbamate (Example 14), 2-(2-chlorophenyl)-5-hydroxy-8-[(3S,4R)-3-hydroxy-1-methylpiperidin-4-yl]-4-oxo-4H-1-benzopyran-7-yl benzyl [(piperidin-2-yl)methyl]carbamate (Example 15), 2-(2-chlorophenyl)-5-hydroxy-8-[(3S,4R)-3-hydroxy-1-methylpiperidin-4-yl]-4-oxo-4H-1-benzopyran-7-yl ethyl [2-(piperidin-2-yl)ethyl]carbamate (Example 16), 2-(2-chlorophenyl)-5-hydroxy-8-[(3S,4R)-3-hydroxy-1-methylpiperidin-4-yl]-4-oxo-4H-1-benzopyran-7-yl methyl{[(3R)-morpholin-3-yl]methyl}carbamate (Example 17), 2-(2-chlorophenyl)-5-hydroxy-8-[(3S,4R)-3-hydroxy-1-methylpiperidin-4-yl]-4-oxo-4H-1-benzopyran-7-yl ethyl [(pyrrolidin-2-yl)methyl]carbamate (Example 18), 2-(2-chlorophenyl)-5-hydroxy-8-[(3S,4R)-3-hydroxy-1-methylpiperidin-4-yl]-4-oxo-4H-1-benzopyran-7-yl methyl{1-[(2R)-piperidin-2-yl]ethyl}carbamate (Example 19), 2-(2-chlorophenyl)-5-hydroxy-8-[(3S,4R)-3-hydroxy-1-methylpiperidin-4-yl]-4-oxo-4H-1-benzopyran-7-yl methyl{1-[(2S)-piperidin-2-yl]ethyl}carbamate (Example 20), 2-(2-chlorophenyl)-5-hydroxy-8-[(3S,4R)-3-hydroxy-1-methylpiperidin-4-yl]-4-oxo-4H-1-benzopyran-7-yl ethyl [(piperidin-3-yl)methyl]carbamate (Example 21), and 2-(2-chlorophenyl)-5-hydroxy-8-[(3S,4R)-3-hydroxy-1-methylpiperidin-4-yl]-4-oxo-4H-1-benzopyran-7-yl ethyl [(pyrrolidin-3-yl)methyl]carbamate (Example 22).

[Item 27]

The compound or the pharmaceutically acceptable salt thereof of any one of items 1, 2, 15, and 16, selected from the following compounds:

2-(2-chlorophenyl)-5-hydroxy-8-[(3S,4R)-3-hydroxy-1-methylpiperidin-4-yl]-4-oxo-4H-1-benzopyran-7-yl ethyl{[(2S)-piperidin-2-yl]methyl}carbamate (Example 1), 2-(2-chlorophenyl)-5-hydroxy-8-[(3S,4R)-3-hydroxy-1-methylpiperidin-4-yl]-4-oxo-4H-1-benzopyran-7-yl ethyl{[(2R)-piperidin-2-yl]methyl}carbamate (Example 2), 2-(2-chlorophenyl)-5-hydroxy-8-[(3S,4R)-3-hydroxy-1-methylpiperidin-4-yl]-4-oxo-4H-1-benzopyran-7-yl methyl{[(2S)-piperidin-2-yl]methyl}carbamate (Example 3), 2-(2-chlorophenyl)-5-hydroxy-8-[(3S,4R)-3-hydroxy-1-methylpiperidin-4-yl]-4-oxo-4H-1-benzopyran-7-yl methyl{[(2R)-piperidin-2-yl]methyl}carbamate (Example 4), 2-(2-chlorophenyl)-5-hydroxy-8-[(3S,4R)-3-hydroxy-1-methylpiperidin-4-yl]-4-oxo-4H-1-benzopyran-7-yl {[(2S)-piperidin-2-yl]methyl}propylcarbamate (Example 5), 2-(2-chlorophenyl)-5-hydroxy-8-[(3S,4R)-3-hydroxy-1-methylpiperidin-4-yl]-4-oxo-4H-1-benzopyran-7-yl {[(2R)-piperidin-2-yl]methyl}propylcarbamate (Example 6), 2-(2-chlorophenyl)-5-hydroxy-8-[(3S,4R)-3-hydroxy-1-methylpiperidin-4-yl]-4-oxo-4H-1-benzopyran-7-yl ethyl[(piperidin-2-yl)methyl]carbamate (Example 7), 2-(2-chlorophenyl)-5-hydroxy-8-[(3S,4R)-3-hydroxy-1-methylpiperidin-4-yl]-4-oxo-4H-1-benzopyran-7-yl methyl[(piperidin-2-yl)methyl]carbamate (Example 8), 2-(2-chlorophenyl)-5-hydroxy-8-[(3S,4R)-3-hydroxy-1-methylpiperidin-4-yl]-4-oxo-4H-1-benzopyran-7-yl [(piperidin-2-yl)methyl]propylcarbamate (Example 9), 2-(2-chlorophenyl)-5-hydroxy-8-[(3S,4R)-3-hydroxy-1-methylpiperidin-4-yl]-4-oxo-4H-1-benzopyran-7-yl [(piperidin-2-yl)methyl]propan-2-ylcarbamate (Example 10), 2-(2-chlorophenyl)-5-hydroxy-8-[(3S,4R)-3-hydroxy-1-methylpiperidin-4-yl]-4-oxo-4H-1-benzopyran-7-yl (2-fluoroethyl) [(piperidin-2-yl)methyl]carbamate (Example 11), 2-(2-chlorophenyl)-5-hydroxy-8-[(3S,4R)-3-hydroxy-1-methylpiperidin-4-yl]-4-oxo-4H-1-benzopyran-7-yl (2-methoxyethyl) [(piperidin-2-yl)methyl]carbamate (Example 12), 2-(2-chlorophenyl)-5-hydroxy-8-[(3S,4R)-3-hydroxy-1-methylpiperidin-4-yl]-4-oxo-4H-1-benzopyran-7-yl [(piperidin-2-yl)methyl](3,3,3-trifluoropropyl)carbamate (Example 13), 2-(2-chlorophenyl)-5-hydroxy-8-[(3S,4R)-3-hydroxy-1-methylpiperidin-4-yl]-4-oxo-4H-1-benzopyran-7-yl [(piperidin-2-yl)methyl](4,4,4-trifluorobutyl)carbamate (Example 14), and 2-(2-chlorophenyl)-5-hydroxy-8-[(3S,4R)-3-hydroxy-1-methylpiperidin-4-yl]-4-oxo-4H-1-benzopyran-7-yl benzyl [(piperidin-2-yl)methyl]carbamate (Example 15).

[Item 28]

The compound or the pharmaceutically acceptable salt thereof of any one of items 1, 2, 15, and 16, selected from the following compounds:

2-(2-chlorophenyl)-5-hydroxy-8-[(3S,4R)-3-hydroxy-1-methylpiperidin-4-yl]-4-oxo-4H-1-benzopyran-7-yl ethyl{[(2S)-piperidin-2-yl]methyl}carbamate (Example 1), 2-(2-chlorophenyl)-5-hydroxy-8-[(3S,4R)-3-hydroxy-1-methylpiperidin-4-yl]-4-oxo-4H-1-benzopyran-7-yl ethyl{[(2R)-piperidin-2-yl]methyl}carbamate (Example 2), 2-(2-chlorophenyl)-5-hydroxy-8-[(3S,4R)-3-hydroxy-1-methylpiperidin-4-yl]-4-oxo-4H-1-benzopyran-7-yl methyl{[(2S)-piperidin-2-yl]methyl}carbamate (Example 3), 2-(2-chlorophenyl)-5-hydroxy-8-[(3S,4R)-3-hydroxy-1-methylpiperidin-4-yl]-4-oxo-4H-1-benzopyran-7-yl methyl{[(2R)-piperidin-2-yl]methyl}carbamate (Example 4), 2-(2-chlorophenyl)-5-hydroxy-8-[(3S,4R)-3-hydroxy-1-methylpiperidin-4-yl]-4-oxo-4H-1-benzopyran-7-yl {[(2S)-piperidin-2-yl]methyl}propylcarbamate (Example 5), and 2-(2-chlorophenyl)-5-hydroxy-8-[(3S,4R)-3-hydroxy-1-methylpiperidin-4-yl]-4-oxo-4H-1-benzopyran-7-yl {[(2R)-piperidin-2-yl]methyl}propylcarbamate (Example 6).

[Item 29]

The compound or the pharmaceutically acceptable salt thereof of any one of items 1, 2, 15, and 16, selected from the following compounds:

2-(2-chlorophenyl)-5-hydroxy-8-[(3S,4R)-3-hydroxy-1-methylpiperidin-4-yl]-4-oxo-4H-1-benzopyran-7-yl ethyl{[(2S)-piperidin-2-yl]methyl}carbamate (Example 1), and 2-(2-chlorophenyl)-5-hydroxy-8-[(3S,4R)-3-hydroxy-1-methylpiperidin-4-yl]-4-oxo-4H-1-benzopyran-7-yl ethyl{[(2R)-piperidin-2-yl]methyl}carbamate (Example 2).

[Item 30]

The compound or the pharmaceutically acceptable salt thereof of any one of items 1, 2, 15, and 16, selected from the following compound:

2-(2-chlorophenyl)-5-hydroxy-8-[(3S,4R)-3-hydroxy-1-methylpiperidin-4-yl]-4-oxo-4H-1-benzopyran-7-yl ethyl{[(2S)-piperidin-2-yl]methyl}carbamate (Example 1).

[Item 31]

A pharmaceutical composition comprising the compound or the pharmaceutically acceptable salt thereof of any one of items 1 to 30.

[Item 32]

A liposome comprising the compound or the pharmaceutically acceptable salt thereof of any one of items 1 to 30.

[Item 33]

A pharmaceutical composition comprising a liposome encapsulating the compound or the pharmaceutically acceptable salt thereof of any one of items 1 to 30.

[Item 34]

The pharmaceutical composition of item 33, wherein the liposome comprises (1) the compound or the pharmaceutically acceptable salt thereof of any one of items 1 to 30, and (2) a phospholipid.

[Item 35]

The pharmaceutical composition of item 33, wherein the phospholipid is one phospholipid selected from the group consisting of phosphatidylcholine, phosphatidylglycerol, phosphatidic acid, phosphatidylethanolamine, phosphatidylserine, phosphatidylinositol, sphingomyelin, soybean lecithin, egg yolk lecithin, hydrogenated egg yolk lecithin, and hydrogenated soybean lecithin, or a combination of two or more thereof.

[Item 36]

The pharmaceutical composition of any one of items 33 to 35, wherein the liposome further comprises a sterol.

[Item 37]

The pharmaceutical composition of item 36, wherein the sterol is a cholesterol.

[Item 38]

The pharmaceutical composition of any one of items 33 to 37, wherein the liposome further comprises a polymer-modified lipid.

[Item 39]

The pharmaceutical composition of item 38, wherein a polymer moiety of the polymer-modified lipid is polyethylene glycol, polypropylene glycol, polyvinyl alcohol, polyvinylpyrrolidone, methoxypolyethylene glycol, methoxypolypropylene glycol, methoxypolyvinyl alcohol, methoxypolyvinylpyrrolidone, ethoxypolyethylene glycol, ethoxypolypropylene glycol, ethoxypolyvinyl alcohol, ethoxypolyvinylpyrrolidone, propoxypolyethylene glycol, propoxypolypropylene glycol, propoxypolyvinyl alcohol, or propoxypolyvinylpyrrolidone.

[Item 40]

The pharmaceutical composition of item 38 or 39, wherein a lipid moiety of the polymer-modified lipid is phosphatidylethanolamine or diacylglycerol.

[Item 41]

The pharmaceutical composition of any one of items 33 to 40, wherein the liposome further comprises an additive selected from the group consisting of an inorganic acid, an inorganic acid salt, an organic acid, an organic acid salt, a saccharide, buffer, an antioxidant, and a polymer.

[Item 42]

A therapeutic agent and/or prophylactic agent for cancer, comprising the compound or the pharmaceutically acceptable salt thereof of any one of items 1 to 30 as an active ingredient.

[Item 43]

The therapeutic agent and/or prophylactic agent of item 42, wherein the cancer is at least one type of cancer selected from the group consisting of acute leukemia, chronic lymphocytic leukemia, chronic myelogenous leukemia, polycythemia vera, malignant lymphoma, plasma cell tumor, multiple myeloma, myelodysplastic syndrome, brain tumor, head and neck cancer, esophageal cancer, thyroid cancer, small cell lung cancer, non-small cell lung cancer, thymoma/thymic carcinoma, breast cancer, gastric cancer, gallbladder/bile duct cancer, liver cancer, hepatocellular carcinoma, pancreatic cancer, colon cancer, rectal cancer, anal cancer, gastrointestinal stromal tumor, choriocarcinoma, endometrial cancer, cervical cancer, ovarian cancer, bladder cancer, prostate cancer, urothelial cancer, renal cancer, renal cell cancer, testicular tumor, testicular germ cell tumor, ovarian germ cell tumor, Wilms tumor, skin cancer, malignant melanoma, neuroblastoma, osteosarcoma, Ewing sarcoma, and soft tissue sarcoma.

[Item 44]

A method for treating and/or preventing cancer in a subject in need thereof, comprising administering a therapeutically and/or prophylactically effective amount of the compound or the pharmaceutically acceptable salt thereof of any one of items 1 to 30, or the pharmaceutical composition of any one of items 31 and 33 to 41, or the liposome of item 42, or the therapeutic agent and/or prophylactic agent of any one of items 42 to 43, to the subject.

[Item 45]

The method of item 44, wherein the cancer is at least one type of cancer selected from the group consisting of acute leukemia, chronic lymphocytic leukemia, chronic myelogenous leukemia, polycythemia vera, malignant lymphoma, plasma cell tumor, multiple myeloma, myelodysplastic syndrome, brain tumor, head and neck cancer, esophageal cancer, thyroid cancer, small cell lung cancer, non-small cell lung cancer, thymoma/thymic carcinoma, breast cancer, gastric cancer, gallbladder/bile duct cancer, liver cancer, hepatocellular carcinoma, pancreatic cancer, colon cancer, rectal cancer, anal cancer, gastrointestinal stromal tumor, choriocarcinoma, endometrial cancer, cervical cancer, ovarian cancer, bladder cancer, prostate cancer, urothelial cancer, renal cancer, renal cell cancer, testicular tumor, testicular germ cell tumor, ovarian germ cell tumor, Wilms tumor, skin cancer, malignant melanoma, neuroblastoma, osteosarcoma, Ewing sarcoma, and soft tissue sarcoma.

[Item 46]

Use of the compound or the pharmaceutically acceptable salt thereof of any one of items 1 to 30, or the pharmaceutical composition of any one of items 31 and 33 to 41, or the liposome of item 31, or the therapeutic agent and/or prophylactic agent of any one of items 42 to 43, for the manufacture of therapeutic agent and/or prophylactic agent for cancer.

[Item 47]

The use of the compound or the pharmaceutically acceptable salt thereof, or the pharmaceutical composition, or the liposome, or the therapeutic agent and/or prophylactic agent of item 46, wherein the cancer is at least one type of cancer selected from the group consisting of acute leukemia, chronic lymphocytic leukemia, chronic myelogenous leukemia, polycythemia vera, malignant lymphoma, plasma cell tumor, multiple myeloma, myelodysplastic syndrome, brain tumor, head and neck cancer, esophageal cancer, thyroid cancer, small cell lung cancer, non-small cell lung cancer, thymoma/thymic carcinoma, breast cancer, gastric cancer, gallbladder/bile duct cancer, liver cancer, hepatocellular carcinoma, pancreatic cancer, colon cancer, rectal cancer, anal cancer, gastrointestinal stromal tumor, choriocarcinoma, endometrial cancer, cervical cancer, ovarian cancer, bladder cancer, prostate cancer, urothelial cancer, renal cancer, renal cell cancer, testicular tumor, testicular germ cell tumor, ovarian germ cell tumor, Wilms tumor, skin cancer, malignant melanoma, neuroblastoma, osteosarcoma, Ewing sarcoma, and soft tissue sarcoma.

[Item 48]

The compound or the pharmaceutically acceptable salt thereof of any one of items 1 to 30, or the pharmaceutical composition of any one of items 31 and 33 to 41, or the liposome of item 31, or the therapeutic agent and/or prophylactic agent of any one of items 42 to 43 for use in the treatment and/or prophylaxis of cancer.

[Item 49]

The compound or the pharmaceutically acceptable salt thereof, or the pharmaceutical composition, or the liposome, or the therapeutic agent and/or prophylactic agent of item 48, wherein the cancer is at least one type of cancer selected from the group consisting of acute leukemia, chronic lymphocytic leukemia, chronic myelogenous leukemia, polycythemia vera, malignant lymphoma, plasma cell tumor, multiple myeloma, myelodysplastic syndrome, brain tumor, head and neck cancer, esophageal cancer, thyroid cancer, small cell lung cancer, non-small cell lung cancer, thymoma/thymic carcinoma, breast cancer, gastric cancer, gallbladder/bile duct cancer, liver cancer, hepatocellular carcinoma, pancreatic cancer, colon cancer, rectal cancer, anal cancer, gastrointestinal stromal tumor, choriocarcinoma, endometrial cancer, cervical cancer, ovarian cancer, bladder cancer, prostate cancer, urothelial cancer, renal cancer, renal cell cancer, testicular tumor, testicular germ cell tumor, ovarian germ cell tumor, Wilms tumor, skin cancer, malignant melanoma, neuroblastoma, osteosarcoma, Ewing sarcoma, and soft tissue sarcoma.

[Item 50]

The compound or the pharmaceutically acceptable salt thereof of any one of items 1 to 30, or the liposome of item 32, or the pharmaceutical composition of any one of items 31 and 33 to 41, or the therapeutic agent and/or prophylactic agent of any one of items 42 to 43, for treating cancer in concomitant use with a concomitantly used medicament or a pharmaceutically acceptable salt thereof, wherein the concomitantly used medicament is at least one selected from the group consisting of a hormonal therapy agent, a chemotherapeutic agent, an immunotherapeutic agent, and an agent that inhibits a cell growth factor or its receptor action.

[Item 51]

The compound or the pharmaceutically acceptable salt thereof of any one of items 1 to 30, or a pharmaceutical as composition comprising the liposome of item 31, or the pharmaceutical composition of any one of items 31 and 33 to 41, or the therapeutic agent and/or prophylactic agent of any one of items 42 to 43, comprised as a combination with a concomitantly used medicament, wherein the concomitantly used medicament is at least one selected from the group consisting of a hormonal therapy agent, a chemotherapeutic agent, an immunotherapeutic agent, and an agent that inhibits a cell growth factor and its receptor action.

[Item 52]

A combination of the compound or the pharmaceutically acceptable salt thereof of any one of items 1 to 30, or the liposome of item 31, or the pharmaceutical composition of any one of items 31 and 33 to 41, or the therapeutic agent and/or prophylactic agent of any one of items 42 to 43 with a concomitantly used medicament, wherein the concomitantly used medicament is at least one selected from the group consisting of a hormonal therapy agent, a chemotherapeutic agent, an immunotherapeutic agent, and an agent that inhibits a cell growth factor and its receptor action.

[Item 53]

The compound or the pharmaceutically acceptable salt thereof of any one of items 1 to 30, or the liposome of item 32, or the pharmaceutical composition of any one of items 31 and 33 to 41, or the therapeutic agent and/or prophylactic agent of any one of items 42 to 43, wherein the compound or the pharmaceutically acceptable salt thereof, or the pharmaceutical composition, or the liposome, or the therapeutic agent and/or prophylactic agent is administered in combination with a concomitantly used medicament or a pharmaceutically acceptable salt thereof, and wherein the concomitantly used medicament is at least one selected from the group consisting of a hormonal therapy agent, a chemotherapeutic agent, an immunotherapeutic agent, and an agent that inhibits a cell growth factor and its receptor action.

The present disclosure also provides, in addition to the above, therapeutic methods, preventive methods, uses, etc., using the compound of the present disclosure, a pharmaceutically acceptable salt thereof, a liposome encapsulant, a pharmaceutical composition, a therapeutic agent or a prophylactic agent, and further details and embodiments of such methods and uses can be understood by those skilled in the art from the description herein.

It is understood that the features described above can be used in combination with one or more. These further embodiments and advantages of the present disclosure will be recognized by those skilled in the art upon reading and understanding the following detailed description, as appropriate.

Effect of the Invention

Alvocidib is a potent and selective inhibitor of CDK, has anti-tumor activity against various tumor cell lines, including human lung cancer and breast cancer, and is therefore expected to be an attractive cancer therapeutic agent, but its pharmacokinetic-based side effects may limit its clinical application. The present disclosure was able to solve such limitations. Furthermore, the present disclosure was able to solve the problem found by the present inventors that the application of Alvocidib to liposomal formulations is limited due to its physical properties.

DESCRIPTION OF EMBODIMENTS

Hereinafter, the present disclosure will be described in more detail. Throughout the entire specification, a singular expression should be understood as encompassing the concept thereof in the plural form unless specifically noted otherwise. Thus, singular articles (e.g., "a", "an", "the" and the like in case of English) should also be understood as encompassing the concept thereof in the plural form unless specifically noted otherwise. Further, the terms used herein should be understood as being used in the meaning that is commonly used in the art, unless specifically noted otherwise. Thus, unless defined otherwise, all terminologies and scientific technical terms that are used herein have the same meaning as the terms commonly understood by those skilled in the art to which the present disclosure pertains. In case of a contradiction, the present specification (including the definitions) takes precedence.

The compounds of the present disclosure may exist in the form of hydrates and/or solvates, and therefore, hydrates and/or solvates of the compounds represented by formula (1), formula (1'), formula (1A) or formula (1A') or pharmaceutically acceptable salts thereof are also encompassed in the compound of the present disclosure.

The compounds represented by formula (1), formula (1'), formula (1A) or formula (1A') may have one or sometimes more asymmetric carbon atoms and may exhibit geometric isomerism or axial chirality, and therefore may exist as several stereoisomers. In the present disclosure, such stereoisomers, mixtures thereof and racemates are also encompassed in the compound of the present disclosure.

Deuterium-substituted compounds in which any one or more $^{1}H$ in the compounds represented by formula (1), formula (1'), formula (1A) or formula (1A') are replaced with $^{2}H(D)$ are also encompassed in the compounds represented by formula (1), formula (1'), formula (1A) or formula (1A').

The compounds represented by formula (1), formula (1'), formula (1A) or formula (1A') and pharmaceutically acceptable salts thereof obtained as crystals may have crystal polymorphs, and all crystal forms are also encompassed in the compound of the present disclosure.

The terms used herein are explained below.

In the present specification, unless otherwise indicated, the number of substituents of the group defined by "optionally substituted" is not particularly limited as long as they can be substituted, and is one or more. Furthermore, unless otherwise indicated, the description of each group also applies when the group is a part or substituent of another group.

Examples of substituent in the present disclosure include a hydrogen atom, a hydroxy group, a carboxyl group, a sulfinic acid group, a sulfonic acid group, a phosphoric acid group, a guanidine group, a cyano group, a halogen atom (a fluorine atom, a chlorine atom, etc.), an alkyl group, an alkylthio group, a cycloalkylthio group, an alkenyl group, an alkynyl group, a cycloalkyl group, a cycloalkenyl group, a cycloalkylcarbonyl group, an alkylcarbonyloxy group, an alkylsulfinyl group, a cycloalkylsulfinyl group, an alkoxy group, a cycloalkoxy group, an alkoxycarbonyl group, a cycloalkyloxycarbonyl group, an alkylcarbonyl group, an aryl group, an arylcarbonyl group, an arylthio group, an aryloxycarbonyl group, a heteroaryl group, a heterocyclic group, an amino group, a cyclic amino group, an aminocarbonyl group, an aminosulfinyl group, an aminosulfonyl group, a heterocyclyloxycarbonyl group, a heterocyclylsulfinyl group, a heterocyclylsulfonyl group, a heterocyclylcarbonyl group, an alkylsulfonyl group, a cycloalkylsulfonyl group, an arylsulfonyl group, an arylsulfinyl group, a heteroarylsulfonyl group, a heteroarylsulfinyl group, and a triphenylphosphonium cationic group. The above-mentioned substituent may be further substituted with the above-mentioned substituent.

In the present specification, "halogen atom" includes a fluorine atom, a chlorine atom, a bromine atom, or an iodine atom. The preferred is a fluorine atom or a chlorine atom.

"Alkyl group" means a linear or branched saturated hydrocarbon group. For example, "$C_{1-4}$ alkyl group" or "$C_6$ alkyl group" means an alkyl group having 1 to 4 or 6 carbon atoms. The same applies to other numbers.

The "$C_{1-10}$ alkyl group" is preferably "$C_{1-6}$ alkyl group", more preferably "$C_{1-3}$ alkyl group".

Specific examples of "$C_{1-10}$ alkyl group" include a methyl group, an ethyl group, a propyl group, a 1-methylethyl group, a butyl group, a 2-methylpropyl group, a 1-methylpropyl group, a 1,1-dimethylethyl group, a pentyl group, a 3-methylbutyl group, a 2-methylbutyl group, a 2,2-dimethylpropyl group, a 1-ethylpropyl group, a 1,1-dimethylpropyl group, a hexyl group, a 4-methylpentyl group, a 3-methylpentyl group, a 2-methylpentyl group, a 1-methylpentyl group, a heptyl group, an octyl group, a nonyl group, or a decyl group, and the like. Propyl group includes a 1-propyl group (a n-propyl group) and a 1-methylethyl group (an isopropyl group).

Specific examples of "$C_{1-6}$ alkyl group" include those having 1 to 6 carbon atoms listed in the specific examples of "$C_{1-10}$ alkyl group". Specific examples of "$C_{1-6}$ alkyl group" include a methyl group, an ethyl group, a propyl group, a 1-methylethyl group, a butyl group, a 2-methylpropyl group, a 1-methylpropyl group, a 1,1-dimethylethyl group, a pentyl group, a 3-methylbutyl group, a 2-methylbutyl group, a 2,2-dimethylpropyl group, a 1-ethylpropyl group, a 1,1-dimethylpropyl group, a hexyl group, a 4-methylpentyl group, a 3-methylpentyl group, a 2-methylpentyl group, a 1-methylpentyl group, and the like.

Specific examples of "$C_{1-3}$ alkyl group" include those having 1 to 3 carbon atoms listed in the specific examples of "$C_{1-10}$ alkyl group". Specific examples of "$C_{1-3}$ alkyl group" include a methyl group, an ethyl group, a propyl group, a 1-methylethyl group, and the like.

"$C_{3-8}$ cycloalkyl group" means cyclic alkyl having 3 to 8 carbon atoms, including those with a partially bridged structure. The "$C_{3-8}$ cycloalkyl group" is preferably "$C_{3-6}$ cycloalkyl group". Specific examples of "$C_{3-8}$ cycloalkyl group" include a cyclopropyl group, a cyclobutyl group, a cyclopentyl group, a cyclohexyl group, a cycloheptyl group or a cyclooctyl group, and the like.

Specific examples of "$C_{3-6}$ cycloalkyl group" include those having 3 to 6 carbon atoms listed in the specific examples of "$C_{3-8}$ cycloalkyl group".

The "$C_{3-8}$ cycloalkyl group" also includes a saturated bicyclo group. Specific examples thereof include groups represented by the following, and the like.

[Chemical Formula 13]

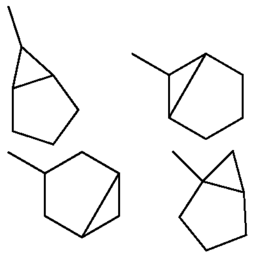

"$C_{1-6}$ alkoxy group" means "$C_{1-6}$ alkyloxy group", and the "$C_{1-6}$ alkyl" moiety has the same meaning as the above-mentioned "$C_{1-6}$ alkyl group".

Specific examples of "$C_{1-6}$ alkoxy group" include a methoxy group, an ethoxy group, a propoxy group, a 1-methylethoxy group, a butoxy group, a 2-methylpropoxy group, a 1-methylpropoxy group, a 1,1-dimethylethoxy group, a pentyloxy group, a 3-methylbutoxy group, a 2-methylbutoxy group, a 2,2-dimethylpropoxy group, a 1-ethylpropoxy group, a 1,1-dimethylpropoxy group, a hexyloxy group, a 4-methylpentyloxy group, a 3-methylpentyloxy group, a 2-methylpentyloxy group, a 1-methylpentyloxy group, a 3,3-dimethylbutoxy group, a 2,2-dimethylbutoxy group, a 1,1-dimethylbutoxy group, or a 1,2-dimethylbutoxy group, and the like.

"$C_{3-8}$ cycloalkoxy group" means "$C_{3-8}$ cycloalkyloxy group", and the "$C_{3-8}$ cycloalkyl" moiety has the same meaning as the above-mentioned "$C_{3-8}$ cycloalkyl group". The "$C_{3-8}$ cycloalkoxy group" is preferably "$C_{3-6}$ cycloalkoxy group". Specific examples of "$C_{3-8}$ cycloalkoxy group" include a cyclopropoxy group, a cyclobutoxy group, a cyclopentyloxy group, a cyclohexyloxy group, a cycloheptyloxy group, a cyclooctyloxy group, and the like.

Specific examples of "$C_{3-6}$ cycloalkoxy group" include those having 3 to 6 carbon atoms listed in the specific examples of "$C_{3-10}$ cycloalkoxy group".

The "$C_{1-6}$ alkoxy" moiety of "$C_{1-6}$ alkoxycarbonyl group" has the same meaning as the above-mentioned "$C_{1-6}$ alkoxy group". Specific examples of "$C_{1-6}$ alkoxycarbonyl group" include a methoxycarbonyl group, an ethoxycarbonyl group, a propoxycarbonyl group, a 1-methylethoxycarbonyl group, butoxycarbonyl group, a 2-methylpropoxycarbonyl group, a 1-methylpropoxycarbonyl group, or a 1,1-dimethylethoxycarbonyl group, and the like.

The "$C_{1-6}$ alkyl" moiety of "$C_{1-6}$ alkylcarbonyl group" has the same meaning as the above-mentioned "$C_{1-6}$ alkyl group". Specific examples of "$C_{1-6}$ alkylcarbonyl group" include a methylcarbonyl group, an ethylcarbonyl group, a propylcarbonyl group, a 1-methylethylcarbonyl group, a butylcarbonyl group, a 2-methylpropylcarbonyl group, a 1-methylpropylcarbonyl group, or a 1,1-dimethylethylcarbonyl group, and the like.

"$C_{6-10}$ aryl group" means an aromatic hydrocarbon group having 6 to 10 carbon atoms. Specific examples of "$C_{6-10}$ aryl group" include a phenyl group, a 1-naphthyl group, or a 2-naphthyl group, and the like. Among them, the preferred is a phenyl group.

The "$C_{6-10}$ aryl group" also includes an 8-membered to 14-membered polycyclic group in which an aromatic group is fused with a $C_{4-6}$ cycloalkane are ring-fused, and a 9-membered to 14-membered polycyclic group in which an aromatic group is fused with, for example, a 5- to 6-membered heterocycle having 1 to 3 same or different atom selected from a nitrogen atom, an oxygen atom and a sulfur atom. Specific examples thereof include groups represented by the following, and the like.

[Chemical Formula 14]

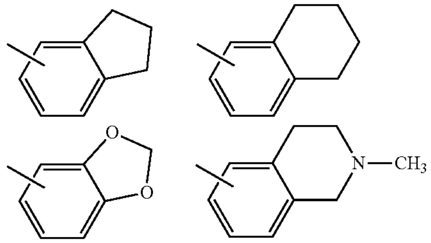

"5-membered to 10-membered heteroaryl group" includes a 5- to 7-membered monocyclic aromatic heterocyclic group ("5-membered to 7-membered heteroaryl group") and an 8- to 10-membered bicyclic aromatic heterocyclic group ("8-membered to 10-membered heteroaryl group"), each containing 1 to 4 atoms independently selected from the group consisting of a nitrogen atom, an oxygen atom and a sulfur atom.

The "5-membered to 10-membered heteroaryl group" is preferably a 5- to 7-membered monocyclic aromatic heterocyclic group ("5-membered to 7-membered heteroaryl group"), more preferably a 5-membered or 6-membered monocyclic aromatic heterocyclic group ("5-membered to 6-membered heteroaryl group"), most preferably a 6-membered monocyclic aromatic heterocyclic group ("6-membered heteroaryl group").

Specific examples of "5-membered to 10-membered heteroaryl group" include a pyridyl group, a pyridazinyl group, an isothiazolyl group, a pyrrolyl group, a furyl group, a thienyl group, a thiazolyl group, an imidazolyl group, a pyrimidinyl group, a thiadiazolyl group, a pyrazolyl group, an oxazolyl group, an isoxazolyl group, a pyrazinyl group, a triazinyl group, a triazolyl group, an oxadiazolyl group, a tetrazolyl group, an indolyl group, an indazolyl group, a quinolyl group, an isoquinolyl group, a benzofuranyl group, a benzothienyl group, a benzoxazolyl group, a benzothiazolyl group, a benzisoxazolyl group, a benzisothiazolyl group, a benzotriazolyl group, a benzimidazolyl group, a quinoxalyl group, a naphthyridinyl group, a pyrrolo[3,2-c]pyridinyl group, a pyrrolo[3,2-c]pyridinyl group, a pyrido[3,2-d]pyridinyl group, a pyrido[3,2-d]pyrimidinyl group, an imidazo[4,5-c]pyridyl group, or a 2-oxo-1,2-dihydro-1,7-naphthyridinyl group, and the like.

The "5-membered to 10-membered heteroaryl group" is preferably a pyridyl group, a pyrimidinyl group, an imidazolyl group, or a pyridazinyl group, more preferably a pyridyl group, a pyrimidinyl group, or an imidazolyl group.

"3- to 10-membered saturated heterocyclic group" includes monocyclic or polycyclic saturated heterocyclic group containing 1 to 4 atoms independently selected from the group consisting of a nitrogen atom, an oxygen atom and a sulfur atom, and the like.

The nitrogen atom, oxygen atom and sulfur atom are all ring-constituting atoms.

The saturated heterocyclic group also includes a saturated heterocyclic group substituted with an oxo group, and a saturated heterocyclic group having a bridged structure. In the saturated heterocyclic group, the ring-constituting nitrogen atom may have a bond.

The "3- to 10-membered saturated heterocyclic group" is preferably "3-membered to 6-membered saturated heterocyclic group", more preferably "4-membered to 6-membered saturated heterocyclic group".

Specific examples of "3- to 10-membered saturated heterocyclic group" include an oxiranyl group, an oxetanyl group, a tetrahydrofuranyl group, a tetrahydrofuranonyl group, a dihydrofuranyl group, a dioxolanyl group, a dioxolanonyl group, a tetrahydropyranyl group, a dioxanyl group, a morpholinyl group, a morpholinonyl group, an oxepanyl group, a dioxepanyl group, an oxathiepanyl group, an oxathiepanonyl group, an oxazepanyl group, an oxazepanonyl group, an oxabicyclooctanyl group, an oxabicycloheptanyl group, an oxabicyclooctanonyl group, an oxabicycloheptanonyl group, an oxaazabicyclooctanyl group, an oxaazabicyclooctanonyl group, a dioxaspirononanyl group, an octahydropyranopyridinyl group, an aziridinyl group, an azetidinyl group, a pyrrolidinyl group, a pyrrolidinoly group, an imidazolidyl group, an imidazolidinonyl group, an oxazolidyl group, an oxazolidinonyl group, an isoxazolidinyl group, an isoxazolidinonyl group, a thiazolidinyl group, a thiazolidinonyl group, an isothiazolidinyl group, an isothiazolidinonyl group, a piperidinyl group, a piperidinonyl group, a thiomorpholinyl group, a thiomorpholinonyl group, a thiomorpholinedioxinyl group, a tetrahydropyrimidinonyl group, a piperazinyl group, a piperazinonyl group, a diketopiperazinyl group, an azepanyl group, a thiazepanyl group, a thiazepanonyl group, a diazepanyl group, a diazepanonyl group, an azabicyclooctanyl group, an azabicyclooctanonyl group, an azabicycloheptanyl group, an azabicycloheptanonyl group, a diazabicyclooctanyl group, a diazabicyclooctanonyl group, a diazabicycloheptanyl group, a diazabicycloheptanonyl group, an azaspirononanyl group, a decahydronaphthyridinyl group, a decahydroquinolyl group or a decahydroisoquinolyl group, and the like.

The "3- to 10-membered saturated heterocyclic group" is preferably a tetrahydropyranyl group, a tetrahydrofuranyl group, an oxetanyl group, a piperidinyl group, a pyrrolidinyl group, or an azetidinyl group.

"3- to 10-membered nitrogen-containing saturated heterocyclic group" includes a monocyclic or polycyclic saturated heterocyclic group containing 1 to 4 ring-constituting nitrogen atoms, and the like.

The nitrogen-containing saturated heterocyclic group also includes a nitrogen-containing saturated heterocyclic group substituted with an oxo group, and a nitrogen-containing saturated heterocyclic group having a bridged structure. In the nitrogen-containing saturated heterocyclic group, the ring-constituting nitrogen atom may have a bond.

The "3- to 10-membered nitrogen-containing saturated heterocyclic group" is preferably "3-membered to 6-membered nitrogen-containing saturated heterocyclic group", more preferably "4-membered to 6-membered nitrogen-containing saturated heterocyclic group".

Specific examples of "3- to 10-membered nitrogen-containing saturated heterocyclic group" include a morpholinyl group, a morpholinonyl group, an oxazepanyl group, an oxazepanonyl group, an oxaazabicyclooctanyl group, an oxaazabicyclooctanonyl group, an octahydropyranopyridinyl group, an aziridinyl group, an azetidinyl group, a pyrrolidinyl group, a pyrrolidinoly group, an imidazolidyl group, an imidazolidinonyl group, an oxazolidyl group, an oxazolidinonyl group, an isoxazolidinyl group, an isoxazolidinonyl group, a thiazolidinyl group, a thiazolidinonyl group, an isothiazolidinyl group, an isothiazolidinonyl group, a piperidinyl group, a piperidinonyl group, a thiomorpholinyl group, a thiomorpholinonyl group, a thiomorpholinedioxinyl group, a tetrahydropyrimidinonyl group, a piperazinyl group, a piperazinonyl group, a diketopiperazinyl group, an azepanyl group, a thiazepanyl group, a thiazepanonyl group, a diazepanyl group, a diazepanonyl group, an azabicyclooctanyl group, an azabicyclooctanonyl group, an azabicycloheptanyl group, an azabicycloheptanonyl group, a diazabicyclooctanyl group, a diazabicyclooctanonyl group, a diazabicycloheptanyl group, a diazabicycloheptanonyl group, an azaspirononanyl group, a decahydronaphthyridinyl group, a decahydroquinolyl group or a decahydroisoquinolyl group, and the like.

The "3- to 10-membered nitrogen-containing saturated heterocyclic group" is preferably a piperidinyl group, a pyrrolidinyl group, or an azetidinyl group.

"4- to 9-membered monocyclic saturated heterocyclic group having one secondary amine in the ring" means a 4- to 9-membered monocyclic heterocyclic group containing one nitrogen atom substituted with hydrogen in the ring. The "4- to 9-membered monocyclic saturated heterocyclic group having one secondary amine in the ring" is preferably "4- to 7-membered monocyclic saturated heterocyclic group having one secondary amine in the ring", more preferably "5- to 6-membered monocyclic saturated heterocyclic group having one secondary amine in the ring", most preferably "6-membered monocyclic saturated heterocyclic group having one secondary amine in the ring".

Specific examples of "4- to 9-membered monocyclic saturated heterocyclic group having one secondary amine in the ring" include groups represented by the following, and the like.

[Chemical Formula 15]

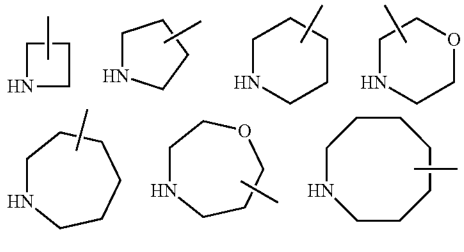

-continued

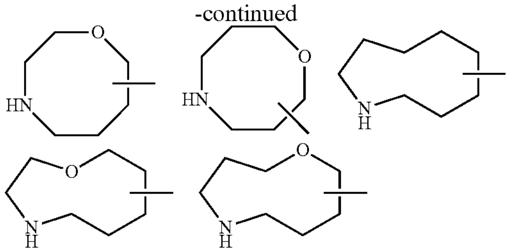

In the compounds represented by formula (1), formula (1'), formula (1A) or formula (1A') of the present disclosure, preferred $R^1$, $R^2$, $R^3$, $R^4$, $R^5$, X, n, p, q and r are as follows, but the technical scope of the present disclosure is not limited to the range of the compounds listed below.

$R^1$ is preferably a $C_{1-6}$ alkyl group (the alkyl group is optionally substituted with 1 to 3 substituents selected from the group consisting of a halogen atom, a $C_{6-10}$ aryl group, a hydroxy group, a carboxyl group, a sulfinic acid group, a sulfonic acid group, a phosphoric acid group, $C_{1-6}$ alkoxy, $—NR^4R^5$, $—CO_2R^4$, $—CONR^4R^5$, $—SO_2R^4$ and $—SO_2NR^4R^5$). $R^1$ is more preferably a $C_{1-6}$ alkyl group (the alkyl group is optionally substituted with 1 to 3 substituents selected from the group consisting of a fluorine atom and $C_{1-6}$ alkoxy).

$R^1$ is still more preferably a methyl group, an ethyl group or a propyl group.

$R^1$ is most preferably an ethyl group.

$R^2$ is preferably a hydrogen atom, or a $C_{1-6}$ alkyl group (the alkyl group is optionally substituted with 1 to 3 substituents selected from the group consisting of a fluorine atom and $C_{1-6}$ alkoxy).

$R^2$ is more preferably a hydrogen atom, or a $C_{1-6}$ alkyl group optionally substituted with 1 to 3 fluorine atoms.

$R^2$ is still more preferably a hydrogen atom, or a $C_{1-3}$ alkyl group.

$R^2$ is most preferably a hydrogen atom.

$R^3$ is preferably a hydrogen atom, or a $C_{1-6}$ alkyl group (the alkyl group is optionally substituted with 1 to 3 substituents selected from the group consisting of a fluorine atom and $C_{1-6}$ alkoxy).

$R^3$ is more preferably a hydrogen atom, or a $C_{1-6}$ alkyl group optionally substituted with 1 to 3 fluorine atoms.

$R^3$ is still more preferably a hydrogen atom, or a $C_{1-3}$ alkyl group.

$R^3$ is most preferably a hydrogen atom.

$R^4$ is preferably a hydrogen atom, or a $C_{1-6}$ alkyl group optionally substituted with 1 to 2 substituents selected from the group consisting of a fluorine atom and a carboxyl group.

$R^4$ is more preferably a hydrogen atom, or a $C_{1-6}$ alkyl group.

$R^4$ is still more preferably a hydrogen atom, or $C_{1-3}$ alkyl.

$R^4$ is most preferably a hydrogen atom, or a methyl group.

$R^5$ is preferably a hydrogen atom, or a $C_{1-6}$ alkyl group optionally substituted with 1 to 2 substituents selected from the group consisting of a fluorine atom and a carboxyl group.

$R^5$ is more preferably a hydrogen atom, or a $C_{1-6}$ alkyl group.

$R^5$ is still more preferably a hydrogen atom, or $C_{1-3}$ alkyl.

$R^5$ is most preferably a hydrogen atom, or a methyl group.

X is preferably $CH_2$ or an oxygen atom.

X is more preferably $CH_2$.

n is preferably 1 or 2.

n is more preferably 1.

n is more preferably 2.

p is preferably 0, 1 or 2.

p is more preferably 0 or 1.

p is still more preferably 0.

q is preferably 1 or 2.

q is more preferably 1.

r is preferably 0, 1 or 2.

r is more preferably 1 or 2.

r is still more preferably 2.

Among the compounds represented by formula (1), the preferred compounds are the following compounds or pharmaceutically acceptable salts thereof.

Among the compounds represented by formula (1) or formula (1'), the preferred embodiment is the following (A).

(A) A compound or a pharmaceutically acceptable salt thereof wherein

- $R^1$ is a $C_{1-6}$ alkyl group (the alkyl group is optionally substituted with 1 to 3 substituents selected from the group consisting of a halogen atom, a $C_{6-10}$ aryl group, a hydroxy group, a carboxyl group, a sulfinic acid group, a sulfonic acid group, a phosphoric acid group, $C_{1-6}$ alkoxy, $—NR^4R^5$, $—CO_2R^4$, $—CONR^4R^5$, $—SO_2R^4$ and $—SO_2NR^4R^5$),
- $R^2$ and $R^3$ are the same or different, each independently a hydrogen atom, or a $C_{1-6}$ alkyl group (the alkyl group is optionally substituted with 1 to 3 substituents selected from the group consisting of a fluorine atom and $C_{1-6}$ alkoxy),
- $R^4$ and $R^5$ are the same or different, each independently a hydrogen atom, or a $C_{1-6}$ alkyl group optionally substituted with 1 to 2 substituents selected from the group consisting of a fluorine atom and a carboxyl group, wherein $R^3$ and $R^4$, if both are $C_{1-10}$ alkyl groups, together with the nitrogen to which they are attached, may form a 3- to 10-membered nitrogen-containing saturated heterocyclic group,
- X is $CH_2$ or an oxygen atom,
- n is 1 or 2,
- p is 0, 1 or 2,
- q is 1 or 2, and
- r is 0, 1 or 2.

Among the compounds represented by formula (1) or formula (1'), the more preferred embodiment is the following (B).

(B) A compound or a pharmaceutically acceptable salt thereof wherein

- $R^1$ is a $C_{1-6}$ alkyl group (the alkyl group is optionally substituted with 1 to 3 substituents selected from the group consisting of a fluorine atom and $C_{1-6}$ alkoxy),
- $R^2$ and $R^3$ are the same or different, each independently a hydrogen atom, or a $C_{1-6}$ alkyl group optionally substituted with 1 to 3 fluorine atoms,
- X is $CH_2$,
- n is 1 or 2,
- p is 0 or 1,
- q is 1, and
- r is 1 or 2.

Among the compounds represented by formula (1) or formula (1'), another more preferred embodiment is the following (C).

(C) A compound or a pharmaceutically acceptable salt thereof wherein

- $R^1$ is a $C_{1-6}$ alkyl group (the alkyl group is optionally substituted with 1 to 3 substituents selected from the group consisting of a fluorine atom and $C_{1-6}$ alkoxy),
- $R^2$ and $R^3$ are the same or different, each independently a hydrogen atom, or a $C_{1-6}$ alkyl group optionally substituted with 1 to 3 fluorine atoms, X is oxygen atom,
n is 1 or 2,
p is 0,
q is 2, and
r is 1.

Among the compounds represented by formula (1) or formula (1'), the still more preferred embodiment is the following (D).

(D) A compound or a pharmaceutically acceptable salt thereof wherein
$R^1$ is a methyl group, an ethyl group or a propyl group,
$R^2$ and $R^3$ are the same or different, each independently a hydrogen atom, or a $C_{1-3}$ alkyl group,
X is $CH_2$,
n is 1,
p is 0,
q is 1, and
r is 2.

Among the compounds represented by formula (1) or formula (1'), another still more preferred embodiment is the following (E).

(E) A compound or a pharmaceutically acceptable salt thereof wherein
$R^1$ is a methyl group, an ethyl group or a propyl group,
$R^2$ and $R^3$ are the same or different, each independently a hydrogen atom, or a $C_{1-3}$ alkyl group,
X is $CH_2$,
n is 2,
p is 0,
q is 1, and
r is 2.

Among the compounds represented by formula (1) or formula (1'), the most preferred embodiment is the following (F).

(F) A compound or a pharmaceutically acceptable salt thereof wherein
$R^1$ is an ethyl group,
$R^2$ and $R^3$ are hydrogen atoms,
X is $CH_2$,
n is 1,
p is 0,
q is 1, and
r is 2.

The "pharmaceutically acceptable salt" includes acid addition salts and base addition salts. Examples of the acid addition salt include inorganic acid salts such as hydrochloride, hydrobromide, sulfate, hydroiodide, nitrate, phosphate, and the like; and organic acid salts such as citrate, oxalate, phthalate, fumarate, maleate, succinate, malate, acetate, formate, propionate, benzoate, trifluoroacetate, methanesulfonate, benzenesulfonate, p-toluenesulfonate, camphorsulfonate, and the like; and examples of the base addition salt include inorganic base salts such as sodium salt, potassium salt, calcium salt, magnesium salt, barium salt, aluminium salt, and the like, salts with an organic base such as trimethylamine, triethylamine, pyridine, picoline, 2,6-lutidine, ethanolamine, diethanolamine, triethanolamine, tromethamine [tris(hydroxymethyl)methylamine], tert-butylamine, cyclohexylamine, dicyclohexylamine, N,N-dibenzylethylamine, and the like, and further salts with a basic or acidic amino acid such as arginine, lysine, ornithine, aspartic acid, glutamic acid, and the like.

Suitable salts and pharmaceutically acceptable salts of starting compounds and target compounds are conventional nontoxic salts. Examples thereof include acid addition salts such as organic acid salts (e.g., acetate, trifluoroacetate, maleate, fumarate, citrate, tartrate, methanesulfonate, benzenesulfonate, formate or p-toluenesulfonate, etc.) and inorganic acid salts (e.g., hydrochloride, hydrobromide, hydroiodide, sulfate, nitrate or phosphate, etc.), salts with an amino acid (e.g., arginine, aspartic acid or glutamic acid, etc.), metal salts such as alkali metal salts (e.g., sodium salt or potassium salt, etc.) and alkali earth metal salts (e.g., calcium salt or magnesium salt, etc.), ammonium salts, organic base salts (e.g., trimethylamine salt, triethylamine salt, pyridine salt, picoline salt, dicyclohexylamine salt or N,N'-dibenzylethylene diamine salt, etc.), or the like, and those skilled in the art can appropriately select from them.

When it is desired to obtain a salt of the compound of the present disclosure, if the compound of the present disclosure is obtained in the form of a salt, it may be purified as it is, or if it is obtained in free form, it may be dissolved or suspended in a suitable organic solvent, and an acid or a base is added thereto to form a salt by a conventional method.

In addition, the compound and pharmaceutically acceptable salt thereof of the present disclosure may exist in an adduct form with water or any kind of solvent, and these adducts are also encompassed by the present disclosure.

In addition, the present disclosure encompasses the compounds represented by formula (1), formula (1'), formula (1A) or formula (1A') or pharmaceutically acceptable salts thereof. It also encompasses hydrates or solvates thereof such as ethanol solvates thereof. Further, the present disclosure encompasses all tautomers, all existing stereoisomers and all crystal forms of the compounds represented by formula (1), formula (1'), formula (1A) or formula (1A') of the present disclosure.

Some of the compounds represented by formula (1), formula (1'), formula (1A) or formula (1A') of the present disclosure include optical isomers based on an optically-active center, atropisomers based on axial or planar chirality caused by restriction of intramolecular rotation, other stereoisomers, tautomers, geometric isomer, and the like. All possible isomers and mixtures thereof, including these, are encompassed within the scope of the present disclosure.

In particular, optical isomers and atropisomers can be obtained as racemates, or optically-active forms when optically-active starting materials or intermediates are used. If necessary, in an appropriate step of the production method described below, racemates of the corresponding starting materials, intermediates or final product can be physically or chemically resolved into their optical enantiomers by a known separation method, such as a method using an optically active column, a fractional crystallization method, or the like. Specifically, for example, in a diastereomer method, two types of diastereomers are generated from a racemate by reaction using an optical resolving agent. Since these different diastereomers generally have different physical properties, they can be separated by a known method such as fractional crystallization, and the like.

The production method of the compound of the present disclosure will be described below. The compounds represented by formula (1), formula (1'), formula (1A) or formula (1A') or pharmaceutically acceptable salts thereof of the present disclosure can be produced from a known compound, for example, by the following Production Methods A to F, or methods analogous thereto, or by appropriately combining synthesis methods well-known to those skilled in the art.

The compound in the reaction may also be in the form of a salt, and examples of such salt include those similar to salts of the compounds represented by formula (1), formula (1'), formula (1A) or formula (1A'), and the like.

In addition, the compound obtained in each step can be used in a next reaction as a reaction solution or as a composition. It can be isolated from a reaction mixture by a conventional method, and easily purified by a separation means such as recrystallization, distillation, chromatography, and the like.

Each symbol of compounds in the following reactions is as defined above, unless specifically indicated.

Production Method A

The compound represented by formula (1) can be produced, for example, by the following production method.

[Chemical Formula 16]

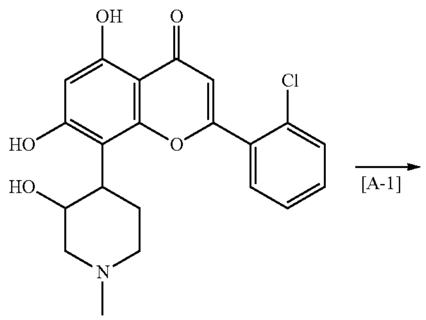

a1

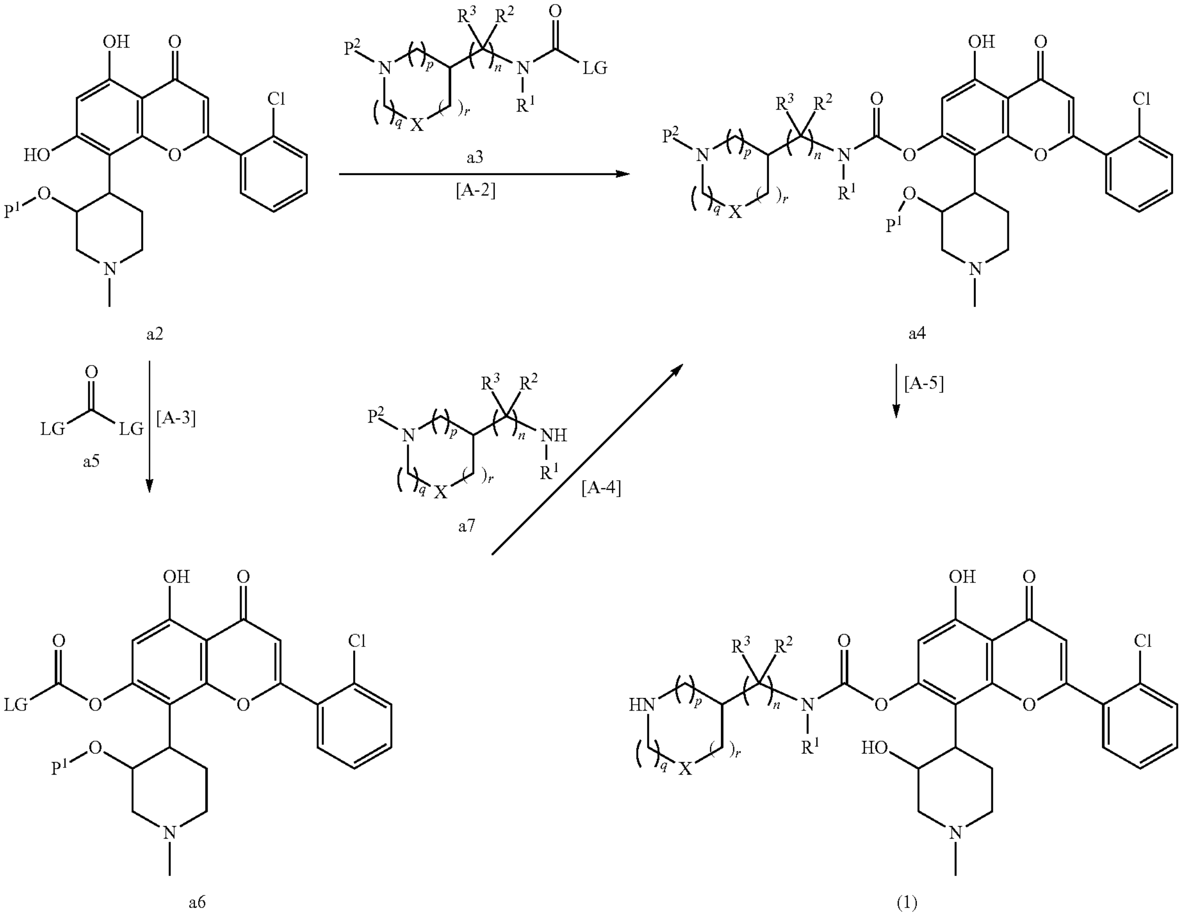

a2 a3 a4 a5 a7 a6 (1)

wherein $R^1$, $R^2$, $R^3$, X, n, p, q and r are as defined in item 1, $P^1$ is an alcohol-protecting group, $P^2$ is an amino-protecting group, and LG is a leaving group.

Examples of the protecting group $P^1$ or $P^2$ include those described as an alcohol-protecting group or an amino-protecting group in Greene's Protective Groups in Organic Synthesis, 5th Edition (Theodora W. Greene, Peter G. M. Wuts, published by John Wiley & Sons, Inc., 2014).

LG is a leaving group, and examples thereof include halogen, an alkoxy group, a sulfonyloxy group or an imidazole group, and the like. Examples of the sulfonyloxy group include a phenylsulfonyloxy group,

[Chemical Formula 17]

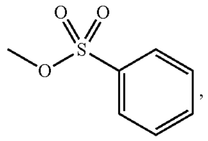

and the like.

[Step A-1]

This step is a step of obtaining compound a2 from compound a1. This step can be performed according to the method described in Greene's Protective Groups in Organic Synthesis, 5th Edition (Theodora W. Greene, Peter G. M. Wuts, published by John Wiley & Sons, Inc., 2014), and the like.

[Step A-2]

This step is a step of obtaining compound a4 by reacting compound a2 with compound a3 obtained by the production method described below in the presence of a base in a suitable solvent. The base used in this step is selected from the bases described below, and the like, and preferred examples include potassium carbonate, cesium carbonate, 4-dimethylaminopyridine, triethylamine and N,N-diisopropylethylamine. The solvent used in this step is selected from the solvents described below, and the like, and preferred examples include methylene chloride, chloroform, tetrahydrofuran (THF), toluene, N,N-dimethylformamide (DMF), N-methyl-2-pyrrolidone and acetonitrile. The reaction time is usually about 0.5 hr to about 48 hr, preferably about 0.5 hr to about 10 hr. The reaction temperature is usually about −20° C. to about 180° C., preferably about 0° C. to about 80° C.

[Step A-3]

This step is a step of obtaining compound a6 by reacting compound a2 with compound a5 in the presence of a base in a suitable solvent. Compound a5 can be commercially available, or can be produced from a known compound by appropriately combining synthetic methods well known to those skilled in the art, and preferred examples includes triphosgene. The base used in this step is selected from the bases described below, and the like, and preferred examples include potassium carbonate, cesium carbonate, 4-dimethylaminopyridine, triethylamine and N,N-diisopropylethylamine. The solvent used in this step is selected from the solvents described below, and the like, and preferred examples include methylene chloride, chloroform, tetrahydrofuran (THF), toluene, N,N-dimethylformamide (DMF), N-methyl-2-pyrrolidone and acetonitrile. The reaction time is usually about 0.5 hr to about 48 hr, preferably about 0.5 hr to about 10 hr. The reaction temperature is usually about −20° C. to about 180° C., preferably about 0° C. to about 80° C.

[Step A-4]

This step is a step of obtaining compound a4 by reacting compound a6 with compound a7 obtained by the production method described below in the presence of a base in a suitable solvent. The base used in this step is selected from the bases described below, and the like, and preferred examples include potassium carbonate, cesium carbonate, 4-dimethylaminopyridine, triethylamine and N,N-diisopropylethylamine. The solvent used in this step is selected from the solvents described below, and the like, and preferred examples include methylene chloride, chloroform, tetrahydrofuran (THF), toluene, N,N-dimethylformamide (DMF), N-methyl-2-pyrrolidone and acetonitrile. The reaction time is usually about 0.5 hr to about 48 hr, preferably about 0.5 hr to about 10 hr. The reaction temperature is usually about −20° C. to about 180° C., preferably about 0° C. to about 80° C.

[Step A-5]

This step is a step of obtaining a compound represented by formula (1) from compound a4. This step can be performed according to the method described in Greene's Protective Groups in Organic Synthesis, 5th Edition (Theodora W. Greene, Peter G. M. Wuts, published by John Wiley & Sons, Inc., 2014), and the like.

Production Method B

The compound represented by formula (1) can be produced, for example, by the following production method.

[Chemical Formula 18]

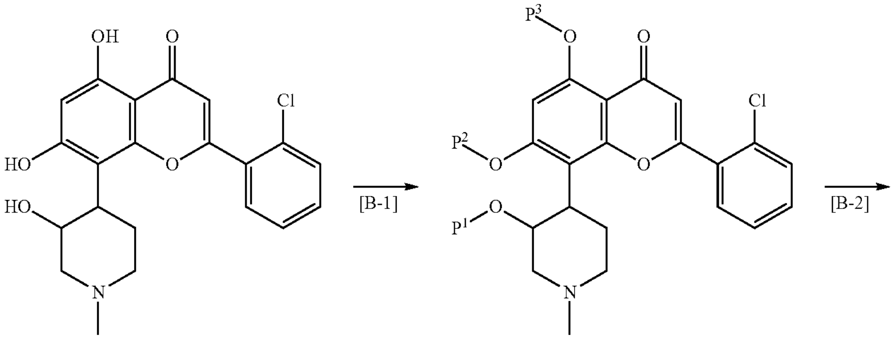

a1 b1

-continued

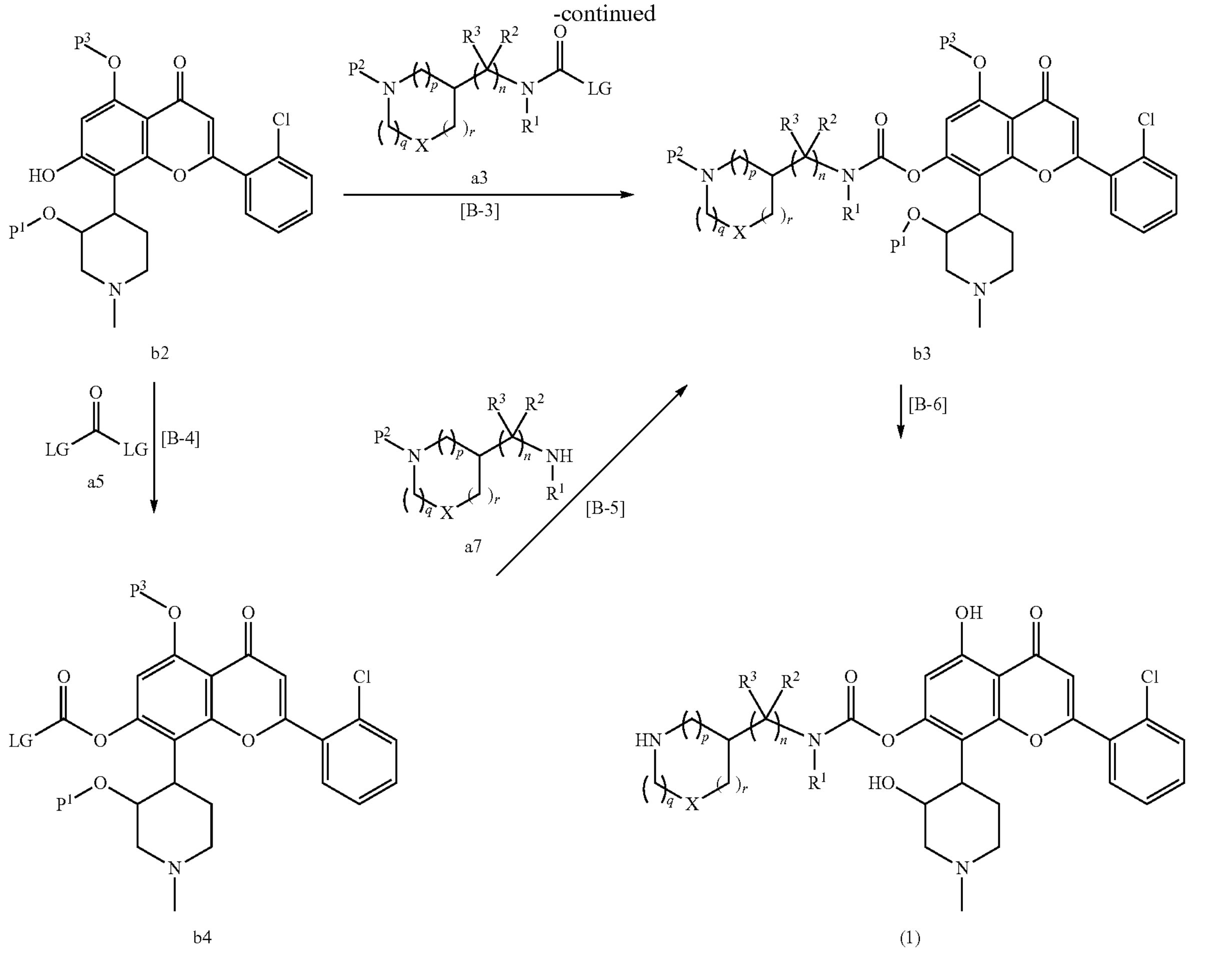

wherein $R^1$, $R^2$, $R^3$, X, n, p, q and r are as defined in item 1, $P^1$ is an alcohol-protecting group, $P^2$ is an amino-protecting group, $P^3$ is a phenol-protecting group, and LG is a leaving group.

Examples of the protecting group $P^1$, $P^2$, or $P^3$ include those described as an alcohol-protecting group, an amino-protecting group or a phenol-protecting group in Greene's Protective Groups in Organic Synthesis, 5th Edition (Theodora W. Greene, Peter G. M. Wuts, published by John Wiley & Sons, Inc., 2014).

LG is a leaving group, and examples thereof include halogen, an alkoxy group, a sulfonyloxy group or an imidazole group, and the like. Examples of the sulfonyloxy group include a phenylsulfonyloxy group,

[Chemical Formula 19]

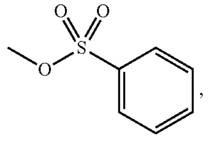
, and the like.

[Step B-1]

This step is a step of obtaining compound b1 from compound a1. This step can be performed according to the method described in Greene's Protective Groups in Organic Synthesis, 5th Edition (Theodora W. Greene, Peter G. M. Wuts, published by John Wiley & Sons, Inc., 2014), and the like.

[Step B-2]

This step is a step of obtaining compound b2 by removing the protecting group $P^3$ of compound b1 in the presence of a base in an alcohol solvent. The base used in this step is selected from the bases described below, and the like, and preferred examples include potassium carbonate, cesium carbonate, 4-dimethylaminopyridine, triethylamine and N,N-diisopropylethylamine. The alcohol solvent used in this step is selected from the solvents described below, and the like, and preferred examples include methanol and ethanol. The reaction time is usually about 0.5 hr to about 48 hr, preferably about 0.5 hr to about 10 hr. The reaction temperature is usually about −20° C. to about 180° C., preferably room temperature to about 100° C. The room temperature is preferably 1 to 30° C.

[Step B-3]

This step is a step of obtaining compound b3 by reacting compound b2 with compound a3 obtained by the production method described below in the presence of a base in a suitable solvent. The base used in this step is selected from the bases described below, and the like, and preferred examples include potassium carbonate, cesium carbonate, 4-dimethylaminopyridine, triethylamine and N,N-diisopropylethylamine. The solvent used in this step is selected from the solvents described below, and the like, and preferred examples include methylene chloride, chloroform, tetrahydrofuran (THF), toluene, N,N-dimethylformamide (DMF), N-methyl-2-pyrrolidone and acetonitrile. The reaction time is usually about 0.5 hr to about 48 hr, preferably about 0.5 hr to about 10 hr. The reaction temperature is usually about −20° C. to about 180° C., preferably about 0° C. to about 80° C.

[Step B-4]

This step is a step of obtaining compound b4 by reacting compound b2 with compound a5 in the presence of a base in a suitable solvent. Compound a5 can be commercially available, or can be produced from a known compound by appropriately combining synthetic methods well known to those skilled in the art, and preferred examples includes triphosgene. The base used in this step is selected from the bases described below, and the like, and preferred examples include potassium carbonate, cesium carbonate, 4-dimethylaminopyridine, triethylamine and N,N-diisopropylethylamine. The solvent used in this step is selected from the solvents described below, and the like, and preferred examples include methylene chloride, chloroform, tetrahydrofuran (THF), toluene, N,N-dimethylformamide (DMF), N-methyl-2-pyrrolidone and acetonitrile. The reaction time is usually about 0.5 hr to about 48 hr, preferably about 0.5 hr to about 10 hr. The reaction temperature is usually about −20° C. to about 180° C., preferably about 0° C. to about 80° C.

[Step B-5]

This step is a step of obtaining compound b3 by reacting compound b4 with compound a7 obtained by the production method described below in the presence of a base in a suitable solvent. The base used in this step is selected from the bases described below, and the like, and preferred examples include potassium carbonate, cesium carbonate, 4-dimethylaminopyridine, triethylamine and N,N-diisopropylethylamine. The solvent used in this step is selected from the solvents described below, and the like, and preferred examples include methylene chloride, chloroform, tetrahydrofuran (THF), toluene, N,N-dimethylformamide (DMF), N-methyl-2-pyrrolidone and acetonitrile. The reaction time is usually about 0.5 hr to about 48 hr, preferably about 0.5 hr to about 10 hr. The reaction temperature is usually about −20° C. to about 180° C., preferably about 0° C. to about 80° C.

[Step B-6]

This step is a step of obtaining the compound of formula (1) from compound b3. This step can be performed according to the method described in Greene's Protective Groups in Organic Synthesis, 5th Edition (Theodora W. Greene, Peter G. M. Wuts, published by John Wiley & Sons, Inc., 2014), and the like.

Production Method C (Production Method of Intermediate)

The above compound represented by a3 can be produced, for example, by the following production method.

[Chemical Formula 20]

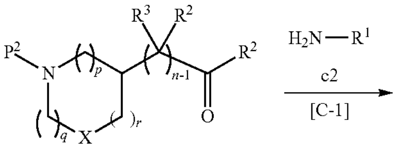

c1

-continued

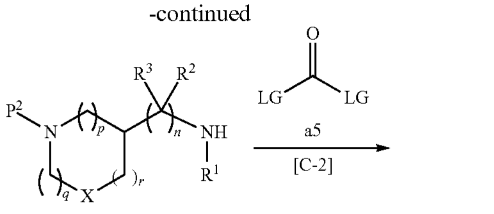

a7

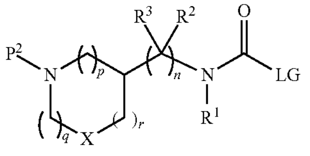

a3 wherein $R^1$, $R^2$, $R^3$, X, n, p, q and r are as defined in item 1, $P^2$ is an amino-protecting group, and LG is a leaving group.

Examples of the protecting group $P^2$ include those described as an amino-protecting group in Greene's Protective Groups in Organic Synthesis, 5th Edition (Theodora W. Greene, Peter G. M. Wuts, published by John Wiley & Sons, Inc., 2014).

LG is a leaving group, and examples thereof include halogen, an alkoxy group, a sulfonyloxy group or an imidazole group, and the like. Examples of the sulfonyloxy group include a phenylsulfonyloxy group,

[Chemical Formula 21]

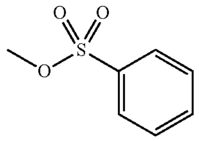, and the like.

[Step C-1]

This step is a step of obtaining compound a7 by reacting compound c1 with compound c2 in the presence of a reducing agent in a suitable acid and solvent. Compounds c1 and c2 can be commercially available, or can be produced from a known compound by appropriately combining synthetic methods well known to those skilled in the art. Examples of the reducing agent used in this step include sodium triacetoxyborohydride, sodium cyanoborohydride and sodium borohydride. Alternatively, the reaction can also be carried out in the presence of a catalyst such as palladium/carbon and palladium hydroxide/carbon under hydrogen atmosphere. Examples of the acid used in this step include acetic acid, trifluoroacetic acid and hydrochloric acid. The solvent used in this step is selected from the solvents described below, and the like, and preferred examples include methanol, ethanol, methylene chloride, chloroform, tetrahydrofuran (THF), ethyl acetate and acetonitrile. The reaction time is usually about 0.5 hr to about 48 hr, preferably about 0.5 hr to about 10 hr. The reaction temperature is usually about −20° C. to about 180° C., preferably about 0° C. to about 80° C.

[Step C-2]

This step is a step of obtaining compound a3 by reacting compound a7 with compound a5 in the presence of a base in a suitable solvent. Compound a5 can be commercially available, or can be produced from a known compound by appropriately combining synthetic methods well known to those skilled in the art, and preferred examples includes triphosgene. The base used in this step is selected from the bases described below, and the like, and preferred examples include potassium carbonate, cesium carbonate, 4-dimethylaminopyridine, triethylamine and N,N-diisopropylethylamine. The solvent used in this step is selected from the solvents described below, and the like, and preferred examples include methylene chloride, chloroform, tetrahydrofuran (THF), toluene, N,N-dimethylformamide (DMF), N-methyl-2-pyrrolidone and acetonitrile. The reaction time is usually about 0.5 hr to about 48 hr, preferably about 0.5 hr to about 10 hr. The reaction temperature is usually about −20° C. to about 180° C., preferably about 0° C. to about 80° C.

Production Method D (Production Method of Intermediate)

The above compound represented by a7 can be produced, for example, by the following production method.

[Chemical Formula 22]

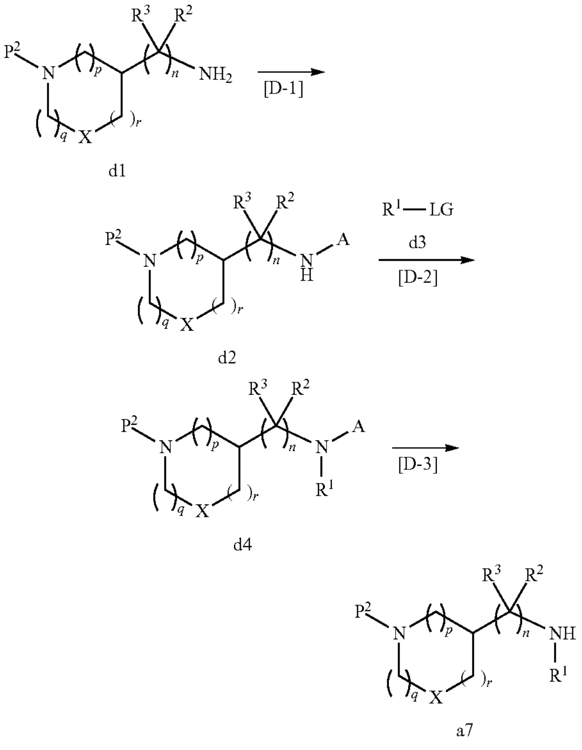

d1 d2 d4 a7 wherein $R^1$, $R^2$, $R^3$, X, n, p, q and r are as defined in item 1, $P^2$ is an amino-protecting group, A is an amino-activating group, and LG is a leaving group.

Examples of the protecting group $P^2$ include those described as an amino-protecting group in Greene's Protective Groups in Organic Synthesis, 5th Edition (Theodora W. Greene, Peter G. M. Wuts, published by John Wiley & Sons, Inc., 2014).

LG is a leaving group, and examples thereof include halogen, an alkoxy group, a sulfonyloxy group or an imidazole group, and the like. Examples of the sulfonyloxy group include a phenylsulfonyloxy group,

[Chemical Formula 23]

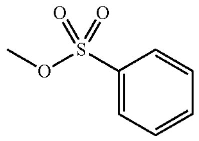

, and the like.

A is an activating group, and examples thereof include a trifluoroacetyl group, an acetyl group, a methanesulfonyl group, a trifluoromethanesulfonyl group, a p-toluenesulfonyl group, a 2-nitrobenzenesulfonyl group, a 4-nitrobenzenesulfonyl group or a 2,4-dinitrobenzenesulfonyl group, and the like.

[Step D-1]

This step is a step of obtaining compound d2 from compound d1. This step can be performed according to the method described in Greene's Protective Groups in Organic Synthesis, 5th Edition (Theodora W. Greene, Peter G. M. Wuts, published by John Wiley & Sons, Inc., 2014), and the like.

[Step D-2]

This step is a step of obtaining compound d4 by reacting compound d2 with compound d3 in the presence of a base in a suitable solvent. Compound d3 can be commercially available, or can be produced from a known compound by appropriately combining synthetic methods well known to those skilled in the art. The base used in this step is selected from the bases described below, and the like, and preferred examples include potassium carbonate, cesium carbonate and sodium hydride. The solvent used in this step is selected from the solvents described below, and the like, and preferred examples include tetrahydrofuran (THF), dioxane, toluene, N,N-dimethylformamide (DMF), N-methyl-2-pyrrolidone and acetonitrile. The reaction time is usually about 0.5 hr to about 48 hr, preferably about 0.5 hr to about 10 hr. The reaction temperature is usually about −20° C. to about 180° C., preferably about 0° C. to about 80° C.

[Step D-3]

This step is a step of obtaining compound a7 from compound d4. This step can be performed according to the method described in Greene's Protective Groups in Organic Synthesis, 5th Edition (Theodora W. Greene, Peter G. M. Wuts, published by John Wiley & Sons, Inc., 2014), and the like.

In each reaction of the production methods described above, in a case other than the case where the use of a protecting group is specifically and explicitly indicated, if any functional group other than the reaction site is modified under the described reaction condition or is unsuitable for performing the described method, a target compound can be obtained by protecting any point other than the reaction site as necessary, and deprotecting after the reaction is finished or a series of reactions are performed.

As a protecting group, a common protecting group such as those described in literature (e.g., Greene's Protective Groups in Organic Synthesis, 5th ed., T. W. Greene, John Wiley & Sons, Inc. (2014), etc.) can be used. Further specifically, examples of the amino-protecting group include benzyloxycarbonyl, tert-butoxycarbonyl, acetyl or benzyl, and the like, and examples of the alcohol-protecting group and phenol-protecting group include trialkylsilyl groups such as trimethylsilyl and tert-butyldimethylsilyl; benzyloxycarbonyl, tert-butoxycarbonyl, acetyl or benzyl, and the like, respectively.

Introduction and removal of the protecting group can be performed by methods commonly used in synthetic organic chemistry (e.g., refer to Greene's Protective Groups in Organic Synthesis, 5th ed., described above) or methods analogous thereto.

The base used in each of the above steps should be selected appropriately depending on the type of reaction and raw material compound, and the like, and examples thereof include basic salts such as sodium carbonate, potassium carbonate, cesium carbonate, sodium acetate, sodium hydride and calcium hydride, aromatic amines such as pyridine, lutidine, 4-dimethylaminopyridine and N,N-dimethylaniline, tertiary amines such as triethylamine, tripropylamine, tributylamine, cyclohexyldimethylamine, N,N-diisopropylethylamine, N-methylpiperidine, N-methylpyrrolidine and N-methylmorpholine, and the like.

The solvent used in each of the above steps should be selected appropriately depending on the type of reaction and raw material compound, and the like, and examples thereof include alcohols such as methanol, ethanol and isopropanol, ketones such as acetone and ethyl methyl ketone, halogenated hydrocarbons such as methylene chloride and chloroform, ethers such as tetrahydrofuran (THF) and dioxane, aromatic hydrocarbons such as toluene and benzene, aliphatic hydrocarbons such as hexane and heptane, esters such as ethyl acetate and propyl acetate, amides such as N,N-dimethylformamide (DMF) and N-methyl-2-pyrrolidone, sulfoxides such as dimethyl sulfoxide (DMSO), and nitriles such as acetonitrile. These solvents can be used alone or in combination of two or more. Furthermore, depending on the type of reaction, organic bases may be used as a solvent.

The compounds of the present disclosure are provided, for example, as anticancer agents, and are indicated for any type of cancer. Specific examples thereof include acute leukemia, chronic lymphocytic leukemia, chronic myelogenous leukemia, polycythemia vera, malignant lymphoma, plasma cell tumor, multiple myeloma, myelodysplastic syndrome, brain tumor, head and neck cancer, esophageal cancer, thyroid cancer, small cell lung cancer, non small cell lung cancer, thymoma/thymic carcinoma, breast cancer, gastric cancer, gallbladder/bile duct cancer, liver cancer, hepatocellular carcinoma, pancreatic cancer, colon cancer, rectal cancer, anal cancer, gastrointestinal stromal tumor, choriocarcinoma, endometrial cancer, cervical cancer, ovarian cancer, bladder cancer, prostate cancer, urothelial cancer, renal cancer, renal cell cancer, testicular tumor, testicular germ cell tumor, ovarian germ cell tumor, Wilms tumor, skin cancer, malignant melanoma, neuroblastoma, osteosarcoma, Ewing sarcoma, and soft tissue sarcoma.

In this specification, "cancer" and "carcinoma" are used interchangeably and have the same meaning, and a concept encompassing carcinomas arising from epithelial cells, sarcomas arising from non-epithelial cells, and blood cancers arising from hematopoietic organs. Blood cancer is a concept encompassing lymphoma and leukemia. The compounds of the present disclosure have an effect to reduce or annihilate carcinoma or to inhibit the growth of carcinoma for the purposes of preventing/or treating cancer. It is noted that in the present disclosure, "prevention" is an action to administer an active ingredient of the present disclosure to a healthy human that does not develop a disease, and a purpose thereof is, for example, to prevent the onset of a disease. "Treatment" is an action to administer an active ingredient of the present disclosure to a person (patient or subject) diagnosed as developing a disease by a medical doctor, and a purpose thereof is, for example, to alleviate the disease and symptoms, to inhibit the growth of carcinoma, or to return it to a state prior to the onset of the disease. In addition, even when the purpose of administration is to prevent a disease or symptoms from deteriorating or carcinoma from growing, if it is administered to a patient or subject, it is an action for therapy.

When the compound of the present disclosure, or the like is administered, the amount of the compound used varies depending on symptoms, age, administration method, and the like. For example, in the case of intravenous injection, an effect is expected by administering to an adult 0.01 mg as the lower limit (preferably 0.1 mg) and 1000 mg as the upper limit (preferably 100 mg) once or in several batches daily depending on the symptoms. Examples of its dosing schedule include single-dose administration, once a day administration for three days in a row, twice a day for one week in a row, and the like. Further, each administration described above can be repeated at intervals of about 1 days to about 60 days.

The compounds of the present disclosure may be administered parenterally or orally, preferably administered parenterally, more preferably administered by intravenous injection. Furthermore, since the compound of the present disclosure has the property of being released in a sustained manner from the formulation after administration and being converted to Alvocidib in the in vivo environment, it is preferably formulated and administered as a pharmaceutically acceptable carrier such as a liposome.

The present disclosure provides a liposome comprising the compound of the present disclosure, or a pharmaceutically acceptable salt thereof.

The liposome encapsulating the compound of the present disclosure comprises at least one "phospholipid".

Examples of "phospholipids" include phosphatidylcholine, phosphatidylglycerol, phosphatidic acid, phosphatidylethanolamine, phosphatidylserine, phosphatidylinositol, sphingomyelin, and the like.

Preferred "phospholipids" are phosphatidylcholine, phosphatidylglycerol, phosphatidylethanolamine and sphingomyelin.

More preferred "phospholipids" are phosphatidylcholine, phosphatidylglycerol and phosphatidylethanolamine.

Still more preferred "phospholipids" are phosphatidylcholine and phosphatidylethanolamine.

Most more preferred "phospholipid" is phosphatidylcholine.

The fatty acid residue in the "phospholipid" is not particularly limited, and examples thereof include saturated or unsaturated fatty acid residues having 14 to 18 carbon atoms, specifically, acyl groups derived from fatty acids such as myristic acid, palmitic acid, stearic acid, oleic acid and linoleic acid. Phospholipids derived from natural products such as egg yolk lecithin and soybean lecithin, as well as hydrogenated egg yolk lecithin and hydrogenated soybean lecithin (also called hydrogenated soybean phospholipid or hydrogenated soybean phosphatidylcholine), in which the unsaturated fatty acid residues are hydrogenated, can also be used.

The amount (mole fraction) of phospholipids in the total liposome membrane components is not particularly limited, and is preferably 30-80%, more preferably 40-70%.

The liposome encapsulating the compound of the present disclosure can contain a sterol. Examples of sterols include cholesterol, β-sitosterol, stigmasterol, campesterol, brassicasterol, ergosterol, and fucosterol, and the like.

Preferred sterol is cholesterol.

The amount (molar fraction) of sterols in the total liposome membrane components is not particularly limited, and is preferably 0 to 60%, more preferably 10 to 50%, still more preferably 30 to 50%.

The liposome encapsulating the compound of the present disclosure can contain a polymer-modified lipid to improve in vivo retention.

Polymer-modified lipid means a lipid modified with a polymer. Polymer-modified lipids are expressed as ""lipid"-"polymer"". The polymer-modified lipid can be a component of the lipid membrane of liposome.

The amount (molar fraction) of polymer-modified lipid in the total liposome membrane components is not particularly limited, and is preferably 0 to 20%, more preferably 1 to 10%, still more preferably 2 to 6%.

A polymer moiety of the polymer-modified lipid is preferably a hydrophilic polymer, more preferably a hydrophilic polymer in which the terminal end of the polymer that is not bound to lipids is alkoxylated. The polymer moiety of the polymer-modified lipid is still more preferably a hydrophilic polymer in which the terminal end of the polymer that is not bound to lipids is methoxylated, ethoxylated or propoxylated. The polymer moiety of the polymer-modified lipid is most preferably a hydrophilic polymer in which the terminal end of the polymer that is not bound to lipids is methoxylated.

The polymer moiety of the polymer-modified lipid is not particularly limited, and specifically includes polyethylene glycol, polypropylene glycol, polyvinyl alcohol, polyvinylpyrrolidone, methoxypolyethylene glycol, methoxypolypropylene glycol, methoxypolyvinyl alcohol, methoxypolyvinylpyrrolidone, ethoxypolyethylene glycol, ethoxypolypropylene glycol, ethoxypolyvinyl alcohol, ethoxypolyvinylpyrrolidone, propoxypolyethylene glycol, propoxypolypropylene glycol, propoxypolyvinyl alcohol, and propoxypolyvinylpyrrolidone. The polymer moiety of the polymer-modified lipid preferably includes polyethylene glycol, methoxypolyethylene glycol, methoxypolypropylene glycol, ethoxypolyethylene glycol, ethoxypolypropylene glycol, propoxypolyethylene glycol, and propoxypolypropylene glycol. The polymer moiety of the polymer-modified lipid more preferably includes polyethylene glycol, methoxypolyethylene glycol, ethoxypolyethylene glycol, ethoxypolypropylene glycol, and propoxypolyethylene glycol. The polymer moiety of the polymer-modified lipid still more preferably includes polyethylene glycol, and methoxypolyethylene glycol. The polymer moiety of the polymer-modified lipid most preferably includes methoxypolyethylene glycol. The molecular weight of the polymer moiety of the polymer-modified lipid is not particularly limited, and, for example, it is 100 to 10000 Daltons, preferably 500 to 8000 Daltons, more preferably 1000 to 7000 Daltons, still more preferably 1500 to 5000 Daltons, most preferably 1500 to 3000 Daltons.

A lipid moiety of the polymer-modified lipid is not particularly limited, and specifically includes phosphatidylethanolamines, and diacylglycerols. The lipid moiety of the polymer-modified lipid preferably includes phosphatidylethanolamines having a saturated or unsaturated fatty acid residue with 14 to 18 carbon atoms, and diacylglycerols having saturated or unsaturated fatty acid residue with 14 to 18 carbon atoms, more preferably includes phosphatidylethanolamines having a saturated fatty acid residue with 14 to 18 carbon atoms, and diacylglycerols having a saturated fatty acid residue with 14 to 18 carbon atoms, still more preferably includes phosphatidylethanolamines having a palmitoyl group or stearoyl group, and diacylglycerols having palmitoyl group or stearoyl group. The lipid moiety of the polymer-modified lipid most preferably includes distearoylphosphatidylethanolamine.

The liposome encapsulating the compound of the present disclosure can contain a pharmaceutically acceptable additive. Additives include inorganic acids, inorganic acid salts, organic acids, organic acid salts, saccharides, buffers, antioxidants, and polymers.

Examples of inorganic acids include phosphoric acid, hydrochloric acid, and sulfuric acid.

Examples of inorganic acid salts include sodium hydrogenphosphate, sodium chloride, ammonium sulfate, and magnesium sulfate.

Examples of organic acids include citric acid, acetic acid, succinic acid, and tartaric acid.

Examples of organic acid salts include sodium citrate, sodium acetate, disodium succinate, and sodium tartrate.

Examples of saccharides include glucose, sucrose, mannitol, sorbitol, and trehalose.

Examples of buffers include L-arginine, L-histidine, trometamol (trishydroxymethylaminomethane, Tris), and salts thereof.

Examples of antioxidants include sodium sulfite, L-cysteine, sodium thioglycolate, sodium thiosulfate, ascorbic acid, and tocopherol.

Examples of polymers include polyvinyl alcohol, polyvinylpyrrolidone, carboxyvinyl polymer, and sodium carboxymethyl cellulose. The polymers are one example of additives used in common injections. The polymer is separate from the polymer in the polymer-modified lipids.

Production Method of Liposome

The liposome encapsulating the compound of the present disclosure can be produced, for example, as follows.

Step 1: Membrane components such as phospholipids and cholesterol are dissolved in an organic solvent such as chloroform, and the organic solvent is evaporated from a flask to form a thin film of the lipid mixture on the inner wall of the flask. As an alternative to the above, membrane components are dissolved in tert-butyl alcohol, and the solution is lyophilized to obtain a lipid mixture as a lyophilized product.

Step 2: An inner aqueous phase solution such as aqueous ammonium sulfate solution, and the like is added to the lipid mixture obtained in Step 1, and the mixture is dispersed to obtain a crude liposome dispersion.

Step 3: The crude liposome dispersion obtained in Step 2 is passed through a filter using an extruder to obtain liposomes of the desired particle size. Alternatively, the crude liposome dispersion obtained in Step 2 is discharged through a nozzle at high pressure using a high-pressure homogenizer to obtain liposomes of the desired particle size.

The particle size of the liposomes is not particularly limited, and is, for example, 10 nm to 200 nm, preferably 30 nm to 150 nm, more preferably 40 nm to 140 nm, still more preferably 50 to 120 nm, most preferably 60 to 100 nm. The particle size of the liposomes is an average value measured by a dynamic light scattering method, and can be measured, for example, using Zetasizer Nano ZS (Malvern Instruments).

Step 4: The outer aqueous phase of the liposome solution obtained in Step 3 is replaced by gel filtration, dialysis, tangential flow filtration, ultracentrifugation, or the like.

Step 5: The liposome solution with the replaced outer aqueous phase obtained in Step 4 is incubated with the compound to be encapsulated to encapsulate the compound in the liposomes.

Step 6: The liposomes encapsulating the compound obtained in Step 5 are subjected to gel filtration, dialysis, tangential flow filtration, or ultracentrifugation, or the like to remove unencapsulated compound.

The state of the compound in the liposome formulation is considered to be "dependent on the additive in the inner aqueous phase of the liposome" regardless of the form of the compound used (free form, salt, hydrate, etc.). For example, if the additive in the inner aqueous phase of the liposome is "ammonium sulfate", the compound is considered to be present in the form of sulfate in the liposome formulation. If the additive in the inner aqueous phase of the liposome is "citric acid", the compound is considered to be present in the form of citrate in the liposome formulation. In addition, the compound may be present in the form of hydrate because of the presence of water in the liposomes.

By combining (1) administering an effective amount of the compound of the present disclosure with (2) one or more selected from the group consisting of (i) administering an effective amount of another anticancer drug, (ii) administering an effective amount of a hormonal therapy agent, and (iii) non-drug therapy, cancer can be more effectively prevented and treated. Examples of non-drug therapy include surgery, radiation therapy, gene therapy, thermotherapy, cryotherapy, laser ablation therapy, and the like, and two or more of these can also be combined.

The compound of the present disclosure can be used in combination with other drugs for purpose of enhancing its effect. Specifically, the compound of the present disclosure can be used in combination with a drug such as a hormonal therapy agent, a chemotherapeutic agent, an immunotherapeutic agent or an agent that inhibits a cell growth factor and its receptor action, and the like. Hereinafter, a drug that may be used in combination with the compound of the present disclosure is abbreviated to a concomitant drug.

The compound of the present disclosure, even when used as a single agent, exhibits excellent anticancer effect, and further the combination use with one or several of the above-described concomitant drugs (polypharmacy) can further enhance its effect or improve the QOL of a patient.

Examples of "hormonal therapy agents" include Fosfestrol, Diethylstilbestrol, Chlorotrianisene, Medroxyprogesterone acetate, Megestrol acetate, Chlormadinone acetate, Cyproterone acetate, Danazol, Dienogest, Asoprisnil, Allylestrenol, Gestrinone, Nomegestrol, Tadenan, Mepartricin, Raloxifene, Ormeloxifene, Levormeloxifene, antiestrogens (e.g., Tamoxifen citrate, Toremifene citrate, and the like), pill preparation, Mepitiostane, Testololactone, aminoglutethimide, LH-RH derivatives (LH-RH agonist (e.g., Goserelin acetate, Buserelin, Leuprorelin, and the like), LH-RH antagonist), Droloxifene, Epitiostanol, ethynyl estradiol sulfonate, aromatase inhibitors (e.g., Fadrozole hydrochloride, Anastrozole, Letrozole, exemestane, vorozole, formestane, and the like), anti-androgens (e.g., Flutamide, Enzalutamide, Apalutamide, Bicalutamide, Nilutamide, and the like), adrenocortical hormone drugs (e.g., Dexamethasone, Prednisolone, Betamethasone, Triamcinolone, and the like), androgen synthesis inhibitors (e.g., Abiraterone, and the like), retinoid, and drugs to delay the metabolism of retinoid (e.g., Liarozole, and the like), and the like.

As "chemotherapeutic agents", for example, alkylating agents, antimetabolites, anticancer antibiotics, plant-derived anticancer agents, molecularly targeted therapeutic agents, immunomodulators, other chemotherapeutic agents, and the like are used. Representative examples are described below.

Examples of "alkylating agents" include Nitrogen mustard, Nitrogen mustard N-oxide hydrochloride, Chlorambucil, Cyclophosphamide, Ifosfamide, Thiotepa, Carboquone, Improsulfan tosylate, Busulfan, Nimustine hydrochloride, Mitobronitol, Melphalan, Dacarbazine, Ranimustine, Estramustine phosphate sodium, Triethylenemelamine, Carmustine, Lomustine, Streptozocin, Pipobroman, Etoglucide, Carboplatin, Cisplatin, miriplatin, Nedaplatin, Oxaliplatin, Altretamine, Ambamustine, Dibrospidium chloride, Fotemustine, Prednimustine, Pumitepa, Ribomustin, Temozolomide, Treosulfan, Trofosfamide, Zinostatin stimalamer, Adozelesin, Cystemustine, Bizelesin, and DDS preparations thereof, and the like.

Examples of "antimetabolites" include Mercaptopurine, 6-Mercaptopurine riboside, Thioinosine, Methotrexate, Pemetrexed, Enocitabine, Cytarabine, Cytarabin ocfosfate, Ancitabine hydrochloride, 5-FU type drugs (e.g., Fluorouracil, Tegafur, UFT, Doxifluridine, Carmofur, Galocitabine, Emitefur, Capecitabine, and the like), Aminopterin, Nelarabine, Leucovorin calcium, tabloid, Butocin, calcium folinate, calcium levofolinate, Cladribine, Emitefur, Fludarabine, Gemcitabine, hydroxycarbamide, Pentostatin, Piritrexim, Idoxuridine, Mitoguazone, Tiazofurin, Ambamustine, Bendamustine, and DDS preparations thereof, and the like.

Examples of "anticancer antibiotics" include Actinomycin D, Actinomycin C, Mitomycin C, Chromomycin A3, Bleomycin hydrochloride, Bleomycin sulfate, Peplomycin sulfate, Daunorubicin hydrochloride, Doxorubicin hydrochloride, Aclarubicin hydrochloride, Pirarubicin hydrochloride, Epirubicin hydrochloride, Neocarzinostatin, Mithramycin, Sarkomycin, Carzinophilin, Mitotane, Zorubicin hydrochloride, Mitoxantrone hydrochloride, Idarubicin hydrochloride, Eribulin, and DDS preparations thereof, and the like.

Examples of "plant-derived anticancer agents" include Etoposide, Etoposide phosphate, Vinblastine sulfate, Vincristine sulfate, Vindesine sulfate, Teniposide, Paclitaxel, Docetaxel, DJ-927, Vinorelbine, Irinotecan, Topotecan, and DDS preparations thereof, and the like.

Examples of "molecularly targeted therapeutic agents" include imatinib, gefitinib, erlotinib, sorafenib, dasatinib, sunitinib, nilotinib, lapatinib, pazopanib, ruxolitinib, crizotinib, vemurafenib, vandetanib, ponatinib, cabozantinib, tofacitinib, regorafenib, bosutinib, axitinib, dabrafenib, trametinib, nintedanib, idelalisib, ceritinib, lenvatinib, palbociclib, alectinib, afatinib, osimertinib, ribociclib, abemaciclib, brigatinib, neratinib, copanlisib, cobimetinib, ibrutinib, acalabrutinib, encorafenib, binimetinib, baricitinib, fostamatinib, lorlatinib, erdafitinib, entrectinib, dacomitinib, sirolimus, everolimus, temsirolimus, olaparib, rucaparib, niraparib, venetoclax, azacitidine, decitabine, vorinostat, panobinostat, romidepsin, bortezomib, carfilzomib, ixazomib, and the like.

Examples of "immunomodulators" include Lenalidomide and Pomalidomide, and the like.

Examples of "other chemotherapeutic agents" include Sobuzoxane, and the like.

Examples of "immunotherapeutic agents (Biological Response Modifier; BRM)" include Picibanil, Krestin, Sizofiran, Lentinan, Ubenimex, interferon, interleukin, macrophage colony stimulating factor, granulocyte-colony stimulating factor, Erythropoietin, Lymphotoxin, BCG vaccine, *Corynebacterium parvum*, Levamisole, polysaccharide K, Procodazole, anti-CTLA4 antibody, anti-PD-1 antibody, anti-PD-L1 antibody, Toll-like Receptors agonists (e.g., TLR7 agonist, TLR8 agonist, TLR9 agonist, and the like).

The cell growth factor in an agent that inhibits a cell growth factor and its receptor action may be any substance as long as it promotes cell growth, and generally includes a factor that is a peptide having a molecular weight of 20,000 or less and exhibits an effect at a low concentration by binding with a receptor. Specific examples thereof include EGF (epidermal growth factor) or substances having substantially the same activity as it (e.g., TGFalpha, and the like), insulin or substances having substantially the same activity as it (e.g., insulin, IGF (insulin-like growth factor)-1, IGF-2, and the like), FGF (fibroblast growth factor) or substances having substantially the same activity as it (e.g., acidic FGF, basic FGF, KGK (keratinocyte growth factor), FGF-10, and the like), and other cell growth factors (e.g., CSF (colony stimulating factor), EPO (erythropoietin), IL-2 (interleukin-2), NGF (nerve growth factor), PDGF (platelet-derived growth factor), TGF-beta (transforming growth factor beta), HGF (hepatocyte growth factor), VEGF (vascular endothelial growth factor), heregulin, angiopoietin, and the like).

The period of administration of the compound of the present disclosure and a concomitant drug is not limited, and these may be administered concurrently or at intervals to a subject to be administered. In addition, a mixture of the compound of the present disclosure and a concomitant drug may be made. The dosage of a concomitant drug can be appropriately selected using clinically used dose as criteria. In addition, the mixing ratio of the compound of the present disclosure and a concomitant drug can be appropriately selected depending on a subject to be administered, an administration route, target disease, symptoms, combinations, and the like. For example, when a subject to be administered is a human, 0.01 to 100 parts by weight of a concomitant drug may be used relative to one part by weight of the compound of the present disclosure. In addition, for purpose of inhibiting its side effect, they can be used in combination with a drug (a concomitant drug) such as an antiemetic agent, a sleep-inducing agent, an anticonvulsant, and the like.

The compounds represented by formula (1), formula (1'), formula (1A) or formula (1A') or pharmaceutically acceptable salts thereof (sometimes referred to as the compound of the present disclosure) are carbamate-type Alvocidib prodrugs, and have "(1) an alkyl group" and "(2) a methyl group or an ethyl group, which is each substituted with a 4- to 9-membered monocyclic saturated heterocyclic group having one secondary amine in the ring (piperidine)" on the nitrogen atom in the carbamate. The compound of the present disclosure is characterized in that the nitrogen atom in the carbamate is not directly substituted with a substituent having a cyclic structure such as a cycloalkyl group or a saturated heterocyclic group.

In one embodiment, the carbamate moiety of the carbamate-type Alvocidib prodrug of the compound of the present disclosure has "(1) an optionally substituted $C_{1-6}$ alkyl group" and "(2) a methyl group or an ethyl group, which is each substituted with a 4- to 9-membered monocyclic saturated heterocyclic group having one secondary amine in the ring" on the nitrogen atom in the carbamate.

In one embodiment, the carbamate moiety of the carbamate-type Alvocidib prodrug of the compound of the present disclosure has "(1) an optionally substituted $C_{1-3}$ alkyl group" and "(2) a methyl group or an ethyl group, which is each substituted with a 5- to 6-membered monocyclic saturated heterocyclic group having one secondary amine in the ring" on the nitrogen atom in the carbamate.

In one embodiment, the carbamate moiety of the carbamate-type Alvocidib prodrug of the compound of the present disclosure has "(1) an optionally substituted methyl group, an ethyl group, or a propyl group" and "(2) a methyl group or an ethyl group, which is each substituted with a piperidinyl group, a pyrrolidinyl group or a morpholinyl group" on the nitrogen atom in the carbamate.

The compound of the present disclosure has excellent stability under acidic conditions, and is rapidly converted to Alvocidib by chemical degradation under neutral conditions without any difference between species. Furthermore, the Alvocidib prodrug of the present disclosure is efficiently encapsulated in liposomes, has excellent storage stability, and exhibits excellent pharmacokinetics. When the Alvocidib prodrug-encapsulated liposome formulation of the present disclosure is administered to tumor-bearing mouse models, it exhibits excellent anti-tumor activity and does not causing weight loss as a side effect, and therefore is useful as a medicine for successfully preventing and/or treating cancer.

That is, the compound of the present disclosure has excellent storage stability, and can be highly efficiently encapsulated in liposomes, and the encapsulated liposomes have excellent blood retention. Since the Alvocidib prodrug is released from the encapsulated liposomes in a sustained release manner and the released prodrug is rapidly converted to Alvocidib by chemical degradation, it is useful as a successful medicine for the prevention and/or treatment of cancer with reduced side effects. The liposomal formulations of the compound of the present disclosure are stable. The compounds of the present disclosure have a marked tumor growth inhibitory effect in vivo.

The compounds represented by formula (1), formula (1'), formula (1A) or formula (1A') of the present disclosure can be converted to the activated form by chemical conversion due to their structural characteristics. Here, chemical conversion means conversion to the activated form in vivo by a pathway other than enzymes. For example, as represented by the following formula:

[Chemical Formula 24]

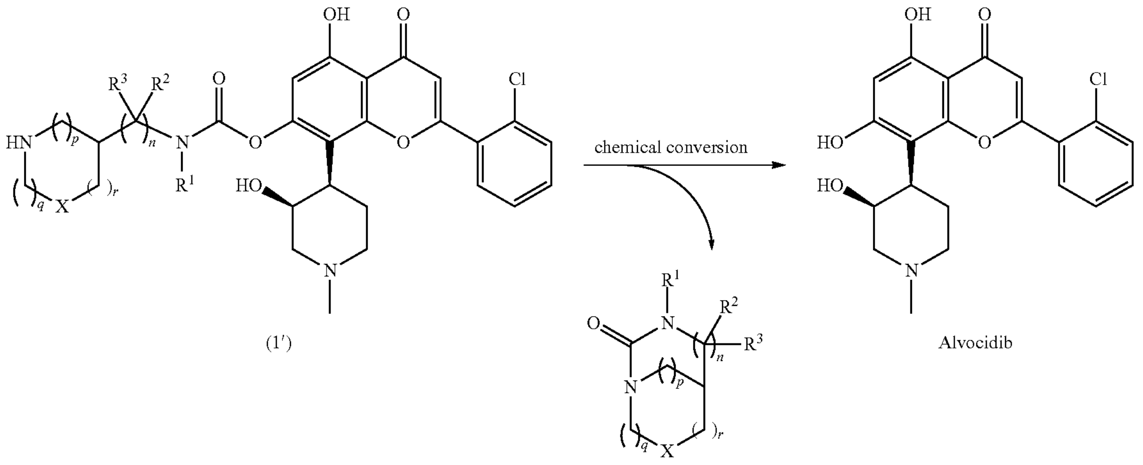

(1')

Alvocidib the compound represented by formula (1') has a cyclic secondary amine structure at the end, and the nitrogen atom of the cyclic secondary amine in the side chain attacks the carbonyl carbon at the root of the carbamate group in vivo, thereby chemically converting it to the active form, Alvocidib.

The present disclosure is explained in more detail below by referring to Reference Examples, Examples and Experimental Examples, but it is not limited thereto. The compounds were identified by elemental analysis, mass spectrum, high-performance liquid chromatography-mass spectrometer; LC-MS, NMR spectrum, high-performance liquid chromatography (HPLC), and the like.

EXAMPLES

The present disclosure is explained in more detail below by referring to Reference Examples, Examples and Experimental Examples, but it is not limited thereto. The compound names given in the following Reference Examples and Examples are not always based on IUPAC nomenclature. Abbreviations may be used to simplify the description, but these abbreviations are as defined above.

The following abbreviations may also be used herein.

The following abbreviations are used in the NMR and MS data in the Reference Examples and Examples.

Me: a methyl group
tert: tertiary
t-Bu: tert-butyl group
CPME: cyclopentyl methyl ether
s: singlet
brs: broad singlet
d: doublet
dd: doublet of doublets
t: triplet
td: triplet of doublets
m: multiplet
J: coupling constant
Hz: Hertz
$CDCl_3$: deuterochloroform
DMSO-$D_6$: deuterodimethyl sulfoxide
hr: hour
min: minute High-Performance Liquid Chromatography-Mass Spectrometer; The measurement conditions for LC-MS are shown below. The observed mass spectrometry value [MS (m/z)] is indicated by $[M+H]^+$ or $[M+2H]^{2+}$, and the retention time is indicated by Rt (min).

Measurement Condition A detection equipment: Waters ACQUITY
column: ACQUITY UPLC BEH 1.7 μm C18 2.1 mm×30 mm
solvent: Solution A: 0.06% formic acid/$H_2O$, Solution B: 0.06%
formic acid/MeCN
gradient condition: 0-1.3 min: linear gradient from B2% to 96%
flow rate: 0.8 mL/min
UV: 220 nm and 254 nm Measurement Condition B detection equipment: Shimadzu LCMS-2020
column: Phenomenex Kinetex 1.7 μm C18 2.1 mm×50 mm
solvent: Solution A: MeCN, Solution B: 0.05% TFA/$H_2O$
gradient condition:
0 min: A/B=10:90
0-1.70 min: A/B=10:90-99:1 (linear gradient)
1.71-1.90 min: A/B=99:1
1.91-3.00 min: A/B=10:90
flow rate: 0.5 mL/min
UV: 220 nm
column temperature: 40° C.

NMR (Nuclear Magnetic Resonance) data used for compound identification was obtained by JNM-ECS400 nuclear magnetic resonance system (400 MHz) manufactured by JEOL.

Symbols used in NMR results mean the following; s is singlet, d is doublet, dd is double of doublets, t is triplet, td is triplet of doublets, m is multiplet, brs is broad singlet, and J is coupling constant.

Reference Example 1 tert-butyl (S)-2-[(2,2,2-trifluoroacetamido)methyl]piperidine-1-carboxylate

[Chemical Formula 25]

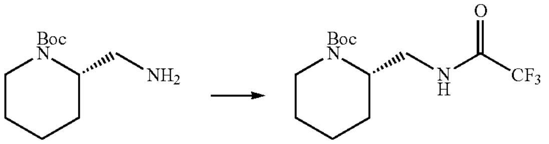

Reference Example 1

To a dichloromethane solution of tert-butyl (S)-2-(aminomethyl)piperidine-1-carboxylate and triethylamine was added trifluoroacetic anhydride, and the mixture was stirred overnight at room temperature. To the reaction solution was added saturated aqueous sodium hydrogencarbonate solution, and the mixture was subjected to extraction with chloroform. The organic layer was dried over anhydrous sodium sulfate and filtered, and the filtrate was concentrated under reduced pressure to give Reference Example 1.

(LC-MS: [M+H]+/Rt(min))=311/0.951 (Measurement Condition A)

Reference Example 2 tert-butyl (S)-2-[(N-ethyl-2,2,2-trifluoroacetamido)methyl]piperidine-1-carboxylate

[Chemical Formula 26]

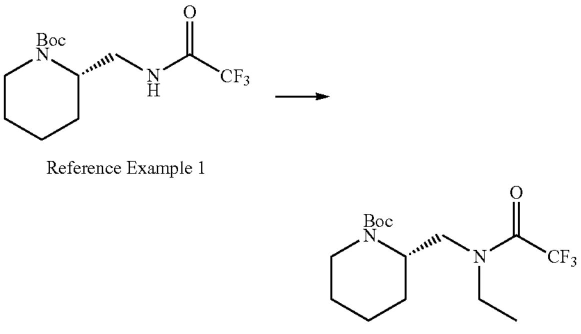

Reference Example 1

Reference Example 2

A solution of Reference Example 1 (3.0 g) in N,N-dimethylformamide (30 mL) was ice-cooled, sodium hydride (0.548 g, >55%, dispersion in paraffin liquid) was added thereto, and the mixture was stirred under ice-cooling for 30 min. To the reaction solution was added iodoethane (1.56 mL), and the mixture was heated to 70° C., and stirred for 3 hr. To the reaction solution was added water, and the mixture was subjected to extraction with diethyl ether. The organic layer was dried over anhydrous sodium sulfate and filtered, and the filtrate was concentrated under reduced pressure, and the residue was purified by silica gel column chromatography (hexane/ethyl acetate) to give Reference Example 2 (1.93 g).

(LC-MS: [M+H]+/Rt(min))=339/1.101 (Measurement Condition A)

Reference Example 3 tert-butyl (S)-2-[(ethylamino)methyl]piperidine-1-carboxylate

[Chemical Formula 27]

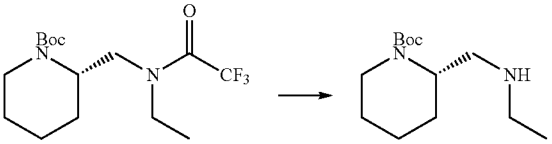

Reference Example 2 Reference Example 3

To a solution of Reference Example 2 (1.93 g) in methanol (20 mL) were added sodium hydroxide (0.228 g) and (water (2 mL), and the mixture was heated with reflux for 5 hr. The reaction solution was concentrated under reduced pressure, to the residue was added water, and the mixture was subjected to extraction with chloroform. The organic layer was dried over anhydrous sodium sulfate and filtered, and the filtrate was concentrated under reduced pressure to give Reference Example 3 (1.27 g). (LC-MS: $[M+H]^+$/Rt (min))=243/0.525 (Measurement Condition A)

Reference Examples 4 to 8 (Compounds Similar to Reference Example 3

The compounds shown in Table 1 were obtained by conducting the reaction and work-up described in Reference Example 1, Reference Example 2 or Reference Example 3 using the corresponding raw material compounds.

TABLE 1

| Reference Example | Chemical Structural Formula | LC-MS $[M+H]^+$/Rt (min) | Measurement Condition |
|---|---|---|---|
| 4 | 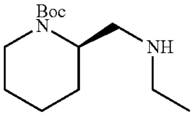 [SMILES: CCNC[C@H]1CCCCN1C(=O)OC(C)(C)C] | 243/ 0.566 | A |
| 5 | 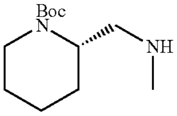 [SMILES: CNC[C@@H]1CCCCN1C(=O)OC(C)(C)C] | 229/ 0.591 | A |
| 6 | 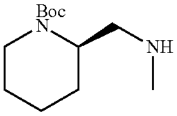 [SMILES: CNC[C@H]1CCCCN1C(=O)OC(C)(C)C] | 229/ 0.596 | A |
| 7 | 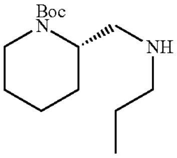 [SMILES: CCCNC[C@@H]1CCCCN1C(=O)OC(C)(C)C] | 257/ 0.749 | A |

TABLE 1-continued

| Reference Example | Chemical Structural Formula | LC-MS $[M + H]^+$/Rt (min) | Measurement Condition |
|---|---|---|---|
| 8 | 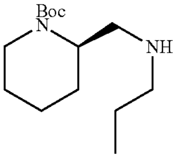 [SMILES: CCCNC[C@H]1CCCCN1C(=O)OC(C)(C)C] | 257/ 0.751 | A |

Reference Example 9 tert-butyl 2-[(ethylamino)methyl]piperidine-1-carboxylate

[Chemical Formula 28]

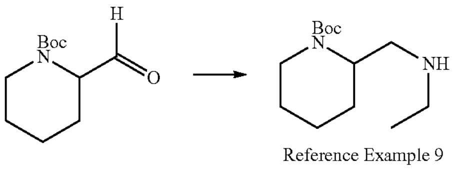

Reference Example 9

To a solution of tert-butyl 2-formylpiperidine-1-carboxylate (10 g) in tetrahydrofuran (100 mL)-methanol (100 mL) were added ethylamine (117 mL, 2 mol/L tetrahydrofuran solution), sodium cyanoborohydride (5.3 g) and acetic acid (26.8 mL) under ice-cooling, and the mixture was stirred at room temperature for 3 hr. To the reaction solution was added saturated aqueous sodium hydrogencarbonate solution, and the mixture was subjected to extraction with chloroform. The organic layer was dried over anhydrous magnesium sulfate and filtered, and the filtrate was concentrated under reduced pressure, and the residue was purified by silica gel column chromatography (chloroform/methanol) to give Reference Example 9 (8.0 g).

(LC-MS: [M+H]+/Rt (min))=243/0.582 (Measurement Condition A)

Reference Examples 10 to 17 (Compounds Similar to Reference Example 9

The compounds shown in Table 2 were obtained by conducting the reaction and work-up described in Reference Example 9 using the corresponding raw material compounds.

TABLE 2

| Reference Example | Chemical Structural Formula | LC-MS $[M + H]^+$/Rt (min) | Measurement Condition |
|---|---|---|---|
| 10 | 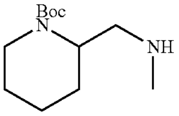 [SMILES: CNCC1CCCCN1C(=O)OC(C)(C)C] | 229/ 0.561 | A |

TABLE 2-continued

| Reference Example | Chemical Structural Formula | LC-MS $[M + H]^+$/Rt (min) | Measurement Condition |
|---|---|---|---|
| 11 | 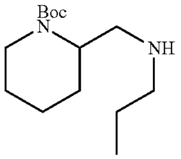 | 257/ 0.677 | A |
| 12 | 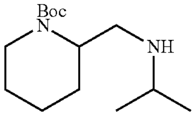 [SMILES: CC(C)NCC1CCCCN1C(=O)OC(C)(C)C] | 257/ 0.561 | A |
| 13 | 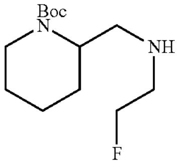 [SMILES: CC(C)(C)OC(=O)N1CCCCC1CNCCF] | 261/ 0.553 | A |
| 14 | 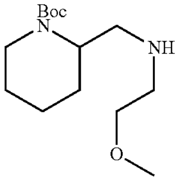 [SMILES: COCCNCC1CCCCN1C(=O)OC(C)(C)C] | 273/ 0.525 | A |
| 15 | 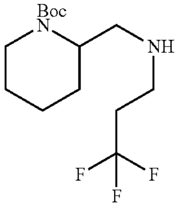 [SMILES: CC(C)(C)OC(=O)N1CCCCC1CNCCC(F)(F)F] | 311/ 0.584 | A |
| 16 | 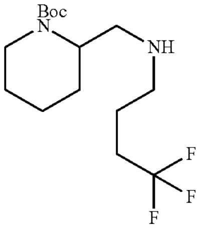 [SMILES: CC(C)(C)OC(=O)N1CCCCC1CNCCCC(F)(F)F] | 325/ 0.610 | A |
| 17 | 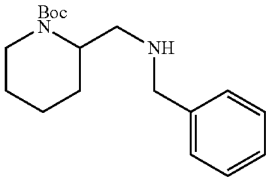 [SMILES: CC(C)(C)OC(=O)N1CCCCC1CNCc1ccccc1] | 305/ 0.698 | A |

Reference Example 18

(3S,4R)-4-{5-[(tert-butoxycarbonyl)oxy]-2-(2-chlorophenyl)-7-hydroxy-4-oxo-4H-1-benzopyran-8-yl}-1-methylpiperidin-3-yl tert-butyl carbonate

[Chemical Formula 29]

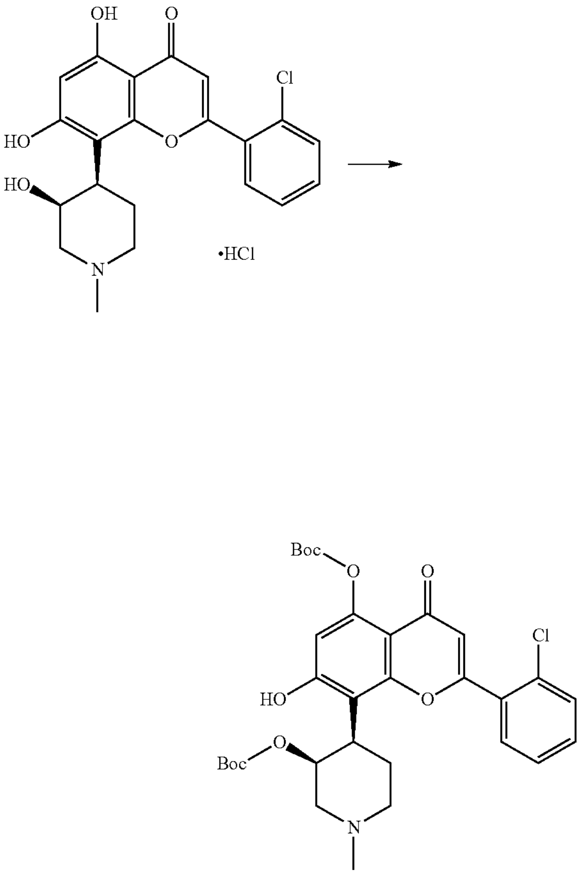

Reference Example 18

Reference Example 18

An acetonitrile solution (150 mL) of 2-(2-chlorophenyl)-5,7-dihydroxy-8-[(3S,4R)-3-hydroxy-1-methylpiperidin-4-yl]-4H-chromen-4-one hydrochloride (10.0 g), di-tert-butyl dicarbonate (19.92 g), N,N-diisopropylethylamine (17.93 mL) and N,N-dimethylaminopyridine (279 mg) was stirred overnight at room temperature. To the reaction solution were added methanol (150 mL) and potassium carbonate (9.46 g), and the mixture was stirred under heating with reflux for 2 hr. To the reaction solution was added water, and the mixture was subjected to extraction with ethyl acetate. The organic layer was dried over anhydrous sodium sulfate, and concentrated, and the residue was purified by silica gel column chromatography (chloroform/methanol) to give Reference Example 18 (15.0 g).

(LC-MS: [M+H]+/Rt(min))=602/0.851 (Measurement Condition A)

Reference Example 19 tert-butyl (2S)-2-({[({5-[(tert-butoxycarbonyl)oxy]-8-{(3S,4R)-3-[(tert-butoxycarbonyl)oxy]-1-methylpiperidin-4-yl}-2-(2-chlorophenyl)-4-oxo-4H-1-benzopyran-7-yl}oxy)carbonyl](ethyl)amino}methyl)piperidine-1-carboxylate

[Chemical Formula 30]

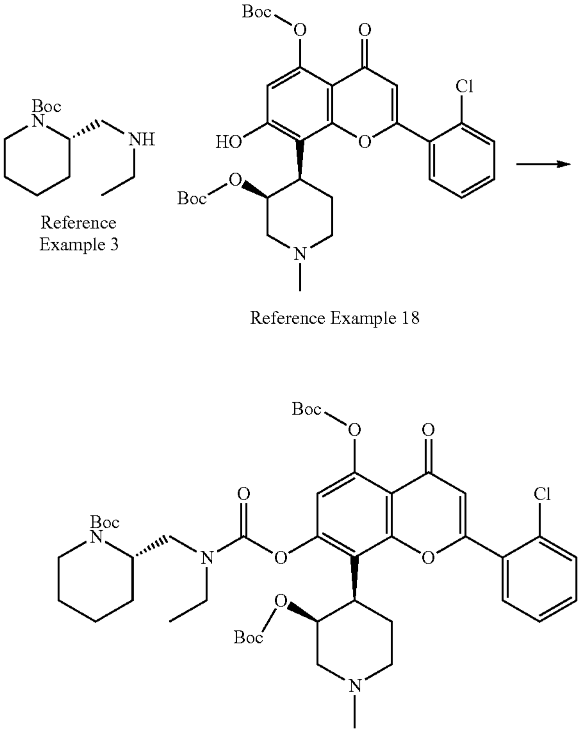

Reference Example 19

To a solution of Reference Example 3 (0.805 g) and N,N-diisopropylethylamine (1.16 mL) in dichloromethane (5 mL) was added triphosgene (0.394 g) under ice-cooling, and the mixture was stirred at room temperature for 1 hr, and the reaction solution was concentrated under reduced pressure. The residue was dissolved in dichloromethane (5 mL), Reference Example 18 (1.0 g), N,N-diisopropylethylamine (1.16 mL) and N,N-dimethylaminopyridine (0.020 g) were added thereto, and the mixture was stirred overnight at room temperature. The reaction solution was concentrated under reduced pressure, and the residue was purified by silica gel column chromatography (chloroform/methanol) to give Reference Example 19 (1.52 g). (LC-MS: [M+H]+/Rt(min)) =870/1.056 (Measurement Condition A)

Reference Examples 20 to 24 (Compounds Similar to Reference Example 19

The compounds shown in Table 3 were obtained by conducting the reaction and work-up described in Reference Example 19 using the corresponding raw material compounds.

TABLE 3
| Reference Example | Chemical Structural Formula | LC-MS [M + H]$^+$/Rt (min) | Measurement Condition |
|---|---|---|---|
| 20 | 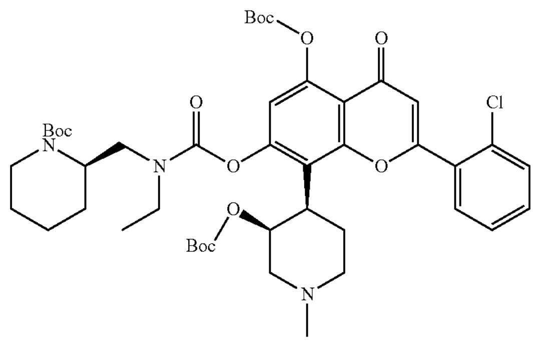 [SMILES: CCN(C[C@H]1CCCCN1C(=O)OC(C)(C)C)C(=O)Oc1cc(OC(=O)OC(C)(C)C)c2c(=O)cc(-c3ccccc3Cl)oc2c1[C@H]1CCN(C)C[C@H]1OC(=O)OC(C)(C)C] | 870/ 1.064 | A |
| 21 | 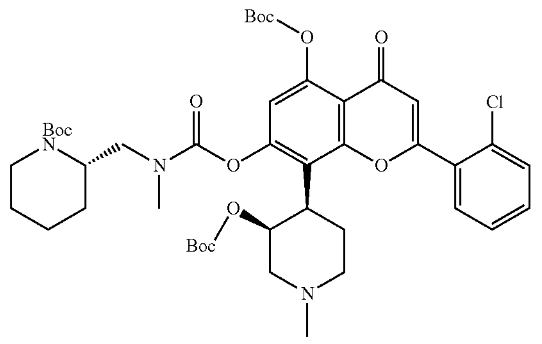 [SMILES: CN1CC[C@H](c2c(OC(=O)N(C)C[C@@H]3CCCCN3C(=O)OC(C)(C)C)cc(OC(=O)OC(C)(C)C)c3c(=O)cc(-c4ccccc4Cl)oc23)[C@H](OC(=O)OC(C)(C)C)C1] | 856/ 1.053 | A |
| 22 | 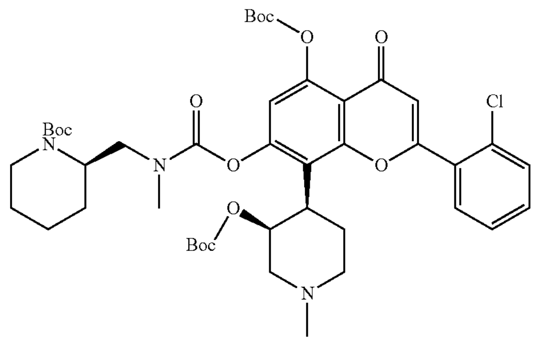 [SMILES: CN1CC[C@H](c2c(OC(=O)N(C)C[C@H]3CCCCN3C(=O)OC(C)(C)C)cc(OC(=O)OC(C)(C)C)c3c(=O)cc(-c4ccccc4Cl)oc23)[C@H](OC(=O)OC(C)(C)C)C1] | 856/ 1.025 | A |

TABLE 3-continued

| Reference Example | Chemical Structural Formula | LC-MS [M + H]+/Rt (min) | Measurement Condition |
|---|---|---|---|
| 23 | 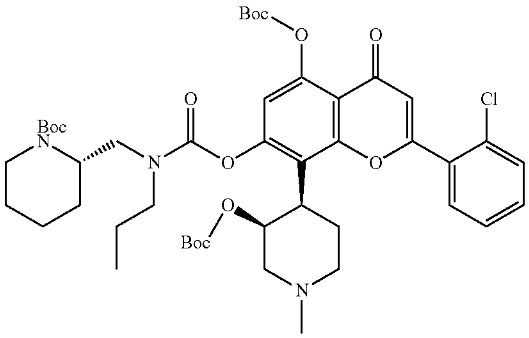 [SMILES: CCCN(C[C@@H]1CCCCN1C(=O)OC(C)(C)C)C(=O)Oc1cc(OC(=O)OC(C)(C)C)c2c(=O)cc(-c3ccccc3Cl)oc2c1[C@H]1CCN(C)C[C@H]1OC(=O)OC(C)(C)C] | 884/ 1.301 | A |
| 24 | 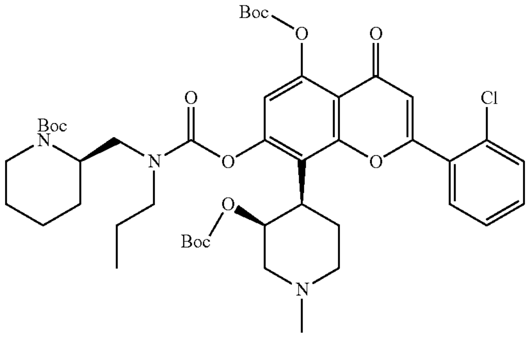 [SMILES: CCCN(C[C@H]1CCCCN1C(=O)OC(C)(C)C)C(=O)Oc1cc(OC(=O)OC(C)(C)C)c2c(=O)cc(-c3ccccc3Cl)oc2c1[C@H]1CCN(C)C[C@H]1OC(=O)OC(C)(C)C] | 884/ 1.236 | A |

Reference Example 25 tert-butyl 2-({[({5-[(tert-butoxycarbonyl)oxy]-8-{(3S,4R)-3-[(tert-butoxycarbonyl)oxy]-1-methylpiperidin-4-yl}-2-(2-chlorophenyl)-4-oxo-4H-1-benzopyran-7-yl}oxy)carbonyl](ethyl)amino}methyl) piperidine-1-carboxylate

[Chemical Formula 31]

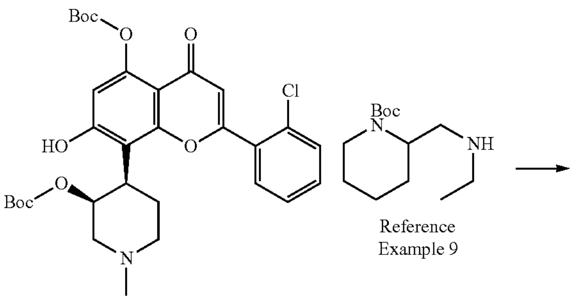

Reference Example 18

-continued

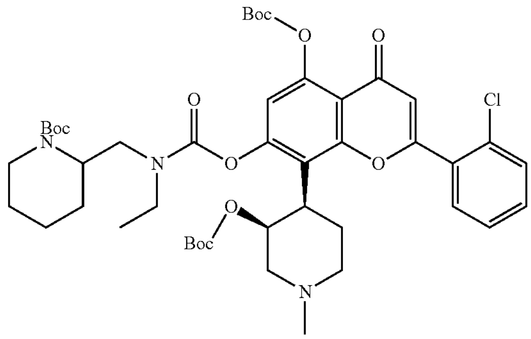

Reference Example 25

To a solution of Reference Example 18 (1.8 g) and triethylamine (2.084 mL) in dichloromethane (20 mL) was added triphosgene (0.293 g), and the mixture was stirred at room temperature for 1 hr. Then, Reference Example 9 (1.449 g) and N,N-dimethylaminopyridine (0.037 g) were added thereto, and the mixture was stirred at room temperature for 4 hr. The reaction solution was concentrated under reduced pressure, and the residue was purified by silica gel column chromatography (chloroform/methanol) to give Reference Example 25 (0.908 g). (LC-MS: [M+H]+/Rt(min))=870/1.352 (Measurement Condition A)

Reference Examples 26 to 33 (Compounds Similar to Reference Example 25
The compounds shown in Table 4 were obtained by conducting the reaction and work-up described in Reference Example 25 using the corresponding raw material compounds.
TABLE 4
| Reference Example | Chemical Structural Formula | LC-MS $[M + H]^+$/Rt (min) | Measurement Condition |
|---|---|---|---|
| 26 | 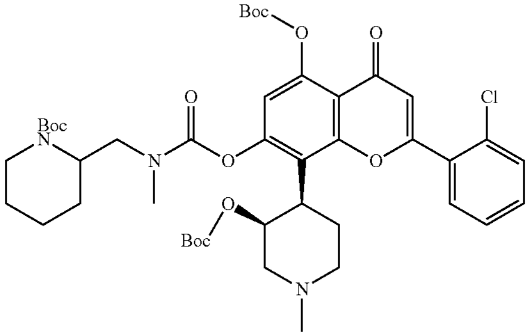 [SMILES: CN1CC[C@H](c2c(OC(=O)N(C)CC3CCCCN3C(=O)OC(C)(C)C)cc(OC(=O)OC(C)(C)C)c3c(=O)cc(-c4ccccc4Cl)oc23)[C@H](OC(=O)OC(C)(C)C)C1] | 856/ 1.319 | A |
| 27 | 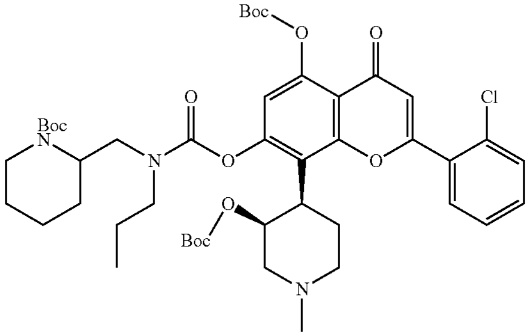 [SMILES: CCCN(CC1CCCCN1C(=O)OC(C)(C)C)C(=O)Oc1cc(OC(=O)OC(C)(C)C)c2c(=O)cc(-c3ccccc3Cl)oc2c1[C@H]1CCN(C)C[C@H]1OC(=O)OC(C)(C)C] | 884/ 2.150 | B |
| 28 | 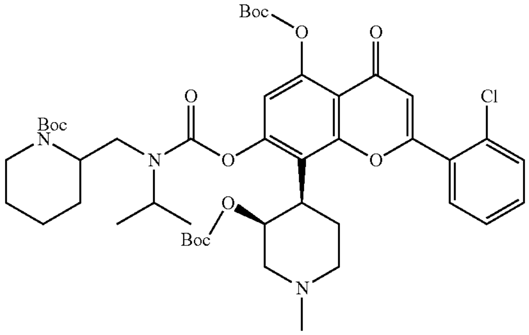 [SMILES: CC(C)N(CC1CCCCN1C(=O)OC(C)(C)C)C(=O)Oc1cc(OC(=O)OC(C)(C)C)c2c(=O)cc(-c3ccccc3Cl)oc2c1[C@H]1CCN(C)C[C@H]1OC(=O)OC(C)(C)C] | 884/ 1.492 | A |
| 29 | 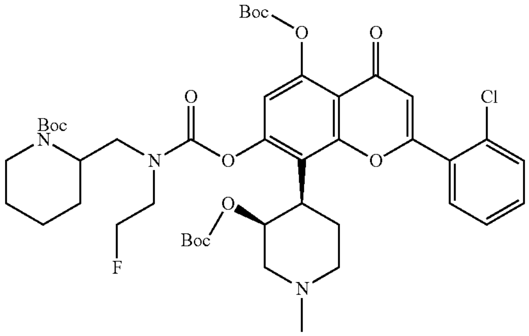 [SMILES: CN1CC[C@H](c2c(OC(=O)N(CCF)CC3CCCCN3C(=O)OC(C)(C)C)cc(OC(=O)OC(C)(C)C)c3c(=O)cc(-c4ccccc4Cl)oc23)[C@H](OC(=O)OC(C)(C)C)C1] | 888/ 1.492 | A |

TABLE 4-continued
| Reference Example | Chemical Structural Formula | LC-MS [M + H]$^+$/Rt (min) | Measurement Condition |
|---|---|---|---|
| 30 | 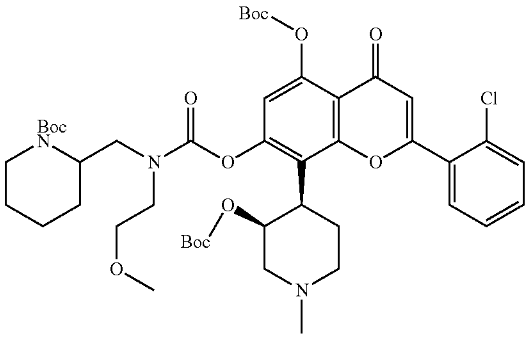 [SMILES: COCCN(CC1CCCCN1C(=O)OC(C)(C)C)C(=O)Oc1cc(OC(=O)OC(C)(C)C)c2c(=O)cc(-c3ccccc3Cl)oc2c1[C@H]1CCN(C)C[C@H]1OC(=O)OC(C)(C)C] | 900/ 2.033 | B |
| 31 | 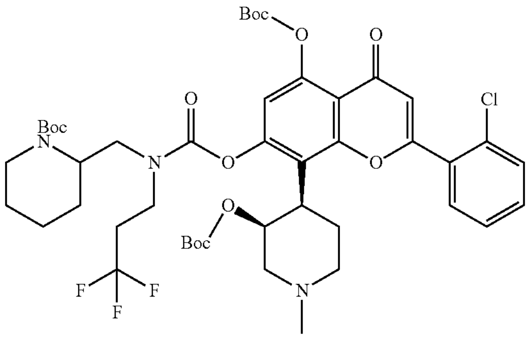 [SMILES: CN1CC[C@H](c2c(OC(=O)N(CCC(F)(F)F)CC3CCCCN3C(=O)OC(C)(C)C)cc(OC(=O)OC(C)(C)C)c3c(=O)cc(-c4ccccc4Cl)oc23)[C@H](OC(=O)OC(C)(C)C)C1] | 938/ 1.465 | A |
| 32 | 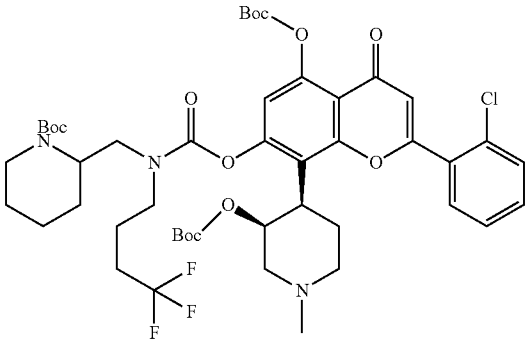 [SMILES: CN1CC[C@H](c2c(OC(=O)N(CCCC(F)(F)F)CC3CCCCN3C(=O)OC(C)(C)C)cc(OC(=O)OC(C)(C)C)c3c(=O)cc(-c4ccccc4Cl)oc23)[C@H](OC(=O)OC(C)(C)C)C1] | 952/ 2.250 | B |
| 33 | 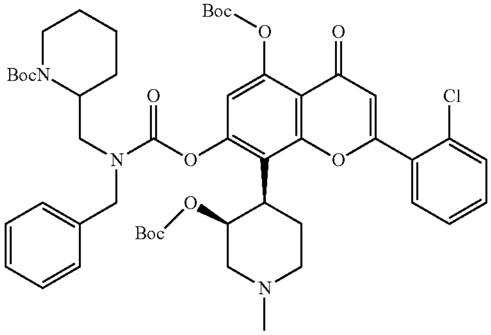 [SMILES: CN1CC[C@H](c2c(OC(=O)N(Cc3ccccc3)CC3CCCCN3C(=O)OC(C)(C)C)cc(OC(=O)OC(C)(C)C)c3c(=O)cc(-c4ccccc4Cl)oc23)[C@H](OC(=O)OC(C)(C)C)C1] | 932/ 1.436 | A |

Example 1

2-(2-chlorophenyl)-5-hydroxy-8-[(3S,4R)-3-hydroxy-1-methylpiperidin-4-yl]-4-oxo-4H-1-benzopyran-7-yl ethyl{[(2S)-piperidin-2-yl]methyl}carbamate ditrifluoroacetate

[Chemical Formula 32]

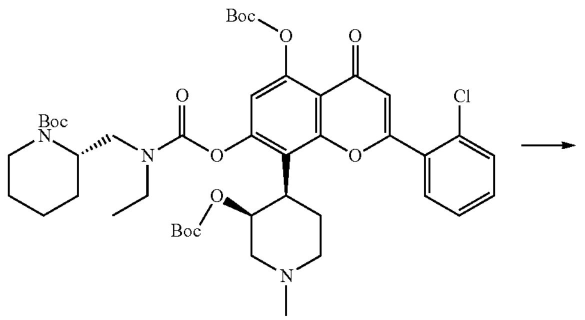

Reference Example 19

-continued

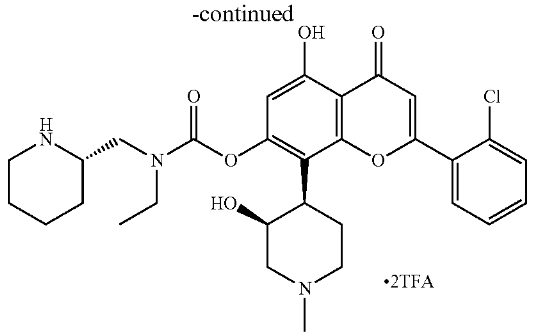

Example 1

To Reference Example 19 (1.52 g) was added 4 mol/L hydrochloric acid/CPME solution (21.8 mL), and the mixture was stirred at room temperature for 3 hr. The reaction solution was concentrated under reduced pressure, and the residue was purified by silica gel column chromatography (ODS column, water/acetonitrile/0.05% trifluoroacetic acid) to give Example 1 (0.775 g).

$^1$H-NMR ($DMSO-D_6$) δ:12.96-12.83 (1H, m), 9.37 (1H, brs), 9.00-8.70 (1H, m), 8.52 (1H, brs), 7.89-7.82 (1H, m), 7.72 (1H, d, J=7.9 Hz), 7.65 (1H, td, J=7.6, 1.2 Hz), 7.59 (1H, t, J=7.6 Hz), 7.04-6.88 (1H, m), 6.80-6.74 (1H, m), 5.63 (1H, brs), 4.01 (1H, s), 3.91-2.83 (13H, m), 2.77-2.69 (3H, m), 1.97-1.69 (4H, m), 1.67-1.33 (3H, m), 1.28-1.07 (3H, m). (LC-MS: $[M+2H]^{2+}$/Rt(min))=286/0.599 (Measurement Condition A)

Examples 2 to 6 (Compounds Similar to Example 1

The compounds shown in Table 5 were obtained by conducting the reaction and work-up described in Example 1 using the corresponding raw material compounds.

TABLE 5

| Ex. | Chemical Structural Formula | $^1$H-NMR ($DMSO-D_6$) δ | LC-MS $[M + 2H]^{2+}$/ Rt (min) | Measurement Condition |
|---|---|---|---|---|
| 2 | 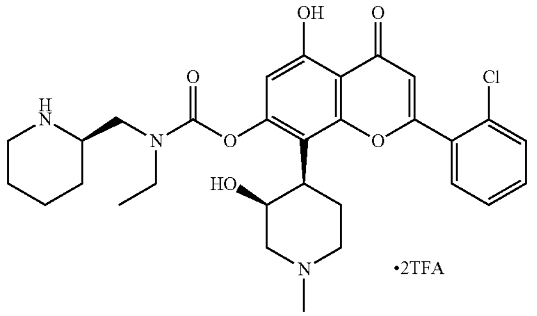 [SMILES: CCN(C[C@H]1CCCCN1)C(=O)Oc1cc(O)c2c(=O)cc(-c3ccccc3Cl)oc2c1[C@H]1CCN(C)C[C@H]1O] | 12.93-12.84 (1H, m), 9.34 (1H, brs), 8.88-8.66 (1H, m), 8.62-8.43 (1H, m), 7.85 (1H, d, J = 7.3 Hz), 7.72 (1H, d, J = 7.9 Hz), 7.66 (1H, t, J = 7.9 Hz), 7.59 (1H, t, J = 7.6 Hz), 6.98-6.74 (2H, m), 5.73-5.47 (1H, m), 4.04-3.94 (1H, m), 3.86-2.80 (13H, m), 2.78-2.69 (3H, m), 1.93-1.69 (4H, m), 1.64-1.30 (3H, m), 1.27-1.07 (3H, m). | 286/ 0.781 | A |

TABLE 5-continued
| Ex. | Chemical Structural Formula | $^1$H-NMR (DMSO-$D_6$) δ | LC-MS $[M + 2H]^{2+}$/ Rt (min) | Measurement Condition |
|---|---|---|---|---|
| 3 | 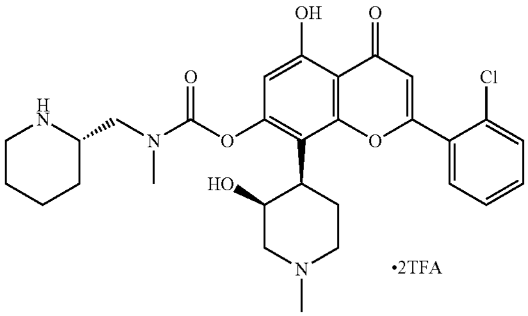 [SMILES: CN1CC[C@H](c2c(OC(=O)N(C)C[C@@H]3CCCCN3)cc(O)c3c(=O)cc(-c4ccccc4Cl)oc23)[C@H](O)C1] •2TFA | 12.88 (1H, s), 9.34 (1H, brs), 8.95-8.65 (1H, m), 8.58-8.40 (1H, m), 7.89-7.81 (1H, m), 7.72 (1H, d, J = 7.9 Hz), 7.66 (1H, td, J = 7.6, 1.8 Hz), 7.61-7.56 (1H, m), 7.00-6.74 (2H, m), 5.60 (1H, s), 4.01 (1H, s), 3.90-3.63 (1H, m), 3.53-2.85 (13H, m), 2.78-2.68 (3H, m), 1.96-1.69 (4H, m), 1.68-1.31 (3H, m). | 279/ 0.542 | A |
| 4 | 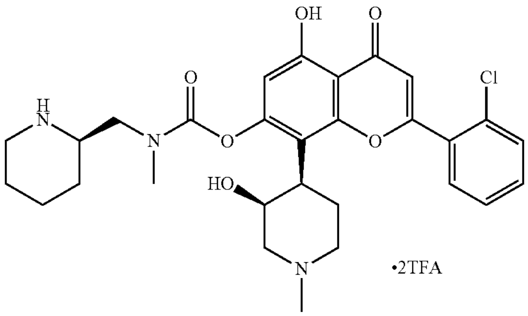 [SMILES: CN1CC[C@H](c2c(OC(=O)N(C)C[C@H]3CCCCN3)cc(O)c3c(=O)cc(-c4ccccc4Cl)oc23)[C@H](O)C1] •2TFA | 12.89-12.83 (1H, m), 9.33 (1H, brs), 8.91-8.65 (1H, m), 8.62-8.39 (1H, m), 7.89-7.80 (1H, m), 7.74-7.69 (1H, m), 7.66 (1H, td, J = 7.6, 1.8 Hz), 7.61-7.56 (1H, m), 6.97-6.75 (2H, m), 5.66-5.52 (1H, m), 4.08-3.94 (1H, m), 3.72-2.87 (14H, m), 2.78-2.68 (3H, m), 1.92-1.70 (4H, m), 1.66-1.32 (3H, m). | 279/ 0.504 | A |
| 5 | 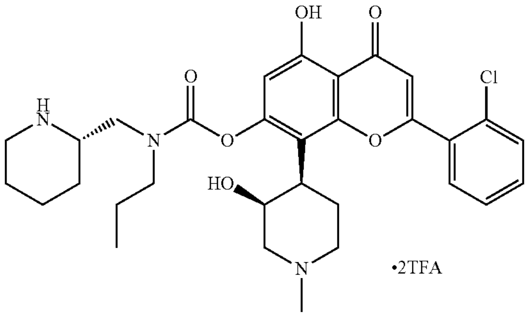 [SMILES: CCCN(C[C@@H]1CCCCN1)C(=O)Oc1cc(O)c2c(=O)cc(-c3ccccc3Cl)oc2c1[C@H]1CCN(C)C[C@H]1O] •2TFA | 12.95-12.85 (1H, m), 9.34 (1H, brs), 8.93-8.61 (1H, m), 8.55-8.39 (1H, m), 7.88-7.82 (1H, m), 7.74-7.69 (1H, m), 7.66 (1H, td, J = 7.6, 1.8 Hz), 7.58 (1H, t, J = 7.3 Hz), 7.01-6.74 (2H, m), 5.75-5.49 (1H, m), 3.99 (1H, s), 3.93-3.57 (1H, m), 3.47-2.83 (12H, m), 2.78-2.67 (3H, m), 1.98-1.67 (4H, m), 1.66-1.32 (5H, m), 0.96-0.77 (3H, m). | 293/ 0.773 | A |
| 6 | 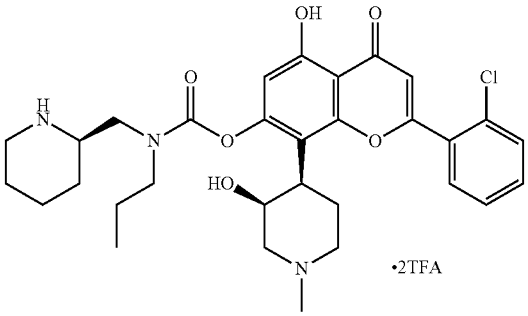 [SMILES: CCCN(C[C@H]1CCCCN1)C(=O)Oc1cc(O)c2c(=O)cc(-c3ccccc3Cl)oc2c1[C@H]1CCN(C)C[C@H]1O] •2TFA | 12.93-12.84 (1H, m), 9.34 (1H, brs), 8.84-8.68 (1H, m), 8.64-8.43 (1H, m), 7.85 (1H, dd, J = 7.9, 1.8 Hz), 7.72 (1H, dd, J = 7.9, 1.2 Hz), 7.68-7.63 (1H, m), 7.61-7.56 (1H, m), 6.92-6.76 (2H, m), 5.74-5.49 (1H, m), 4.03-3.96 (1H, m), 3.89-2.82 (13H, m), 2.78-2.68 (3H, m), 1.92-1.72 (4H, m), 1.70-1.29 (5H, m), 0.95-0.82 (3H, m). | 293/ 0.760 | A |

Example 7

2-(2-chlorophenyl)-5-hydroxy-8-[(3S,4R)-3-hydroxy-1-methylpiperidin-4-yl]-4-oxo-4H-1-benzopyran-7-yl ethyl[(piperidin-2-yl)methyl]carbamate dihydrochloride

[Chemical Formula 33]

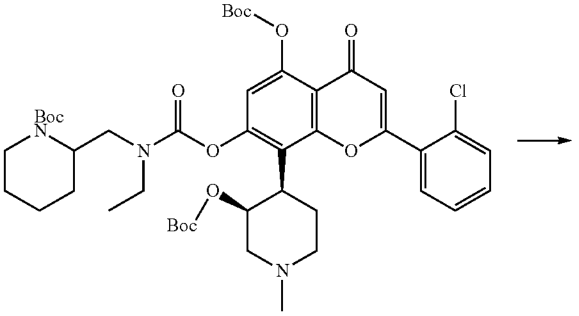

Reference Example 25

-continued

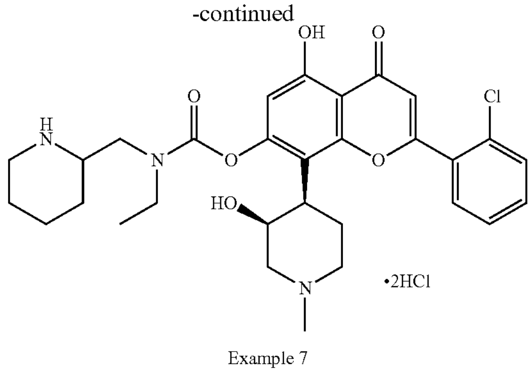

Example 7

To Reference Example 25 (0.908 g) was added 4 mol/L hydrochloric acid/CPME solution (26.1 mL), and the mixture was stirred at room temperature for 2 hr. The reaction solution was concentrated under reduced pressure, and the residue was washed with diisopropyl ether to give Example 7 (0.705 g).

$^1$H-NMR (DMSO-$D_6$) δ:12.99-12.78 (1H, m), 9.74-8.72 (3H, m), 7.93-7.86 (1H, m), 7.74-7.69 (1H, m), 7.67-7.57 (2H, m), 6.91-6.74 (2H, m), 5.68-5.55 (1H, m), 4.02-3.95 (1H, m), 3.64-2.78 (13H, m), 2.76-2.68 (3H, m), 1.93-1.36 (7H, m), 1.28-1.08 (3H, m). (LC-MS: [M+2H]2+/Rt(min))=286/0.652 (Measurement Condition A)

Examples 8 to 15 (Compounds Similar to Example 7

The compounds shown in Table 6 were obtained by conducting the reaction and work-up described in Example 7 using the corresponding raw material compounds.

TABLE 6

| Ex. | Chemical Structural Formula | $^1$H-NMR (DMSO-$D_6$) δ | LC-MS $[M + 2H]^{2+}$/ Rt (min) | Measurement Condition |
|---|---|---|---|---|
| 8 | 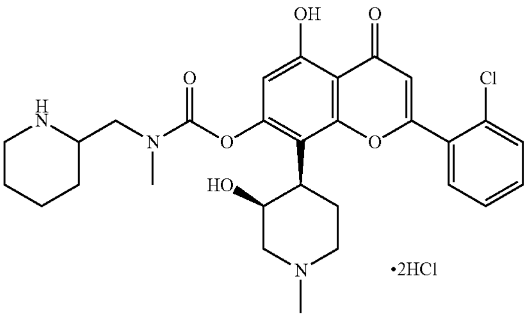 [SMILES: CN1CC[C@H](c2c(OC(=O)N(C)CC3CCCCN3)cc(O)c3c(=O)cc(-c4ccccc4Cl)oc23)[C@H](O)C1] | 12.90-12.82 (1H, m), 9.74-8.67 (3H, m), 7.93-7.85 (1H, m), 7.74-7.68 (1H, m), 7.67-7.58 (2H, m), 6.94-6.74 (2H, m), 5.67-5.50 (1H, m), 4.08-3.95 (1H, m), 3.72-2.78 (14H, m), 2.75-2.67 (3H, m), 1.92-1.56 (5H, m), 1.53-1.31 (2H, m). | 279/ 0.533 | A |

TABLE 6-continued
| Ex. | Chemical Structural Formula | $^1$H-NMR (DMSO-$D_6$) δ | LC-MS [M + 2H]$^{2+}$/ Rt (min) | Measurement Condition |
|---|---|---|---|---|
| 9 | 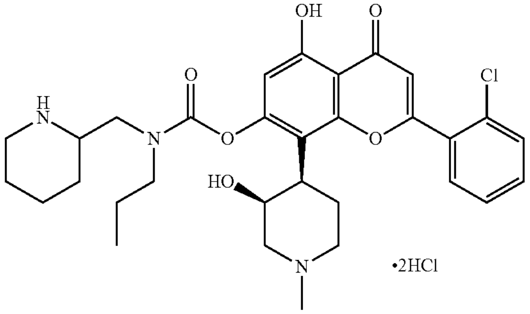 •2HCl | 12.94-12.83 (1H, m), 9.66-8.65 (3H, m), 7.93-7.84 (1H, m), 7.71 (1H, d, J = 7.9 Hz), 7.69-7.56 (2H, m), 6.91-6.75 (2H, m), 5.70-5.55 (1H, m), 4.04-3.94 (1H, m), 3.65-2.78 (13H, m), 2.76-2.67 (3H, m), 1.92-1.32 (9H, m), 0.96-0.83 (3H, m). | 293/ 0.739 | A |
| 10 | 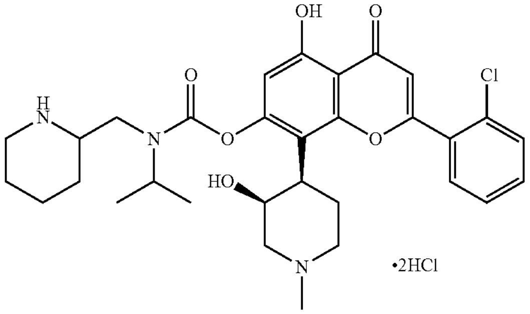 •2HCl | 12.94-12.81 (1H, m), 9.67-8.42 (3H, m), 7.88 (1H, d, J = 6.7 Hz), 7.71 (1H, d, J = 7.3 Hz), 7.69-7.56 (1H, m), 6.99-6.75 (2H, m), 5.72-5.54 (1H, m), 4.32-3.76 (2H, m), 3.58-2.78 (11H, m), 2.78-2.68 (3H, m), 1.99-1.55 (5H, m), 1.55-1.38 (2H, m), 1.38-1.13 (6H, m). | 293/ 0.733 | A |
| 11 | 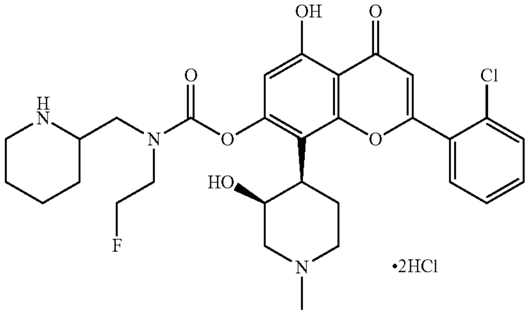 [SMILES: CCCN(CC1CCCCN1)C(=O)Oc1cc(O)c2c(=O)cc(-c3ccccc3Cl)oc2c1[C@H]1CCN(C)C[C@H]1O] •2HCl | 12.94-12.84 (1H, m), 9.65-8.55 (3H, m), 7.93-7.85 (1H, m), 7.71 (1H, d, J = 7.9 Hz), 7.69-7.56 (2H, m), 6.96-6.75 (2H, m), 5.69-5.55 (1H, m), 4.85-4.52 (2H, m), 4.10-2.78 (14H, m), 2.77-2.68 (3H, m), 1.92-1.09 (7H, m). | 295/ 0.785 | A |
| 12 | 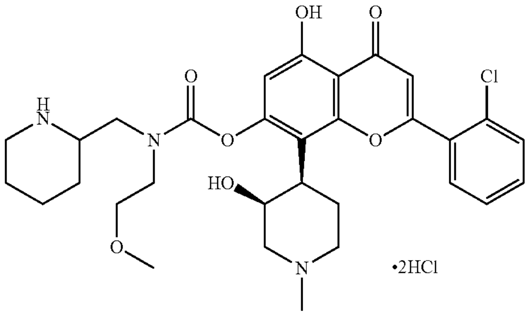 [SMILES: COCCN(CC1CCCCN1)C(=O)Oc1cc(O)c2c(=O)cc(-c3ccccc3Cl)oc2c1[C@H]1CCN(C)C[C@H]1O] •2HCl | 12.93-12.85 (1H, m), 9.74-8.42 (3H, m), 7.95-7.84 (1H, m), 7.75-7.69 (1H, m), 7.68-7.57 (2H, m), 6.93-6.74 (2H, m), 5.70-5.54 (1H, m), 4.09-2.78 (19H, m), 2.77-2.68 (3H, m), 1.91-1.09 (7H, m). | 301/ 0.874 | A |

TABLE 6-continued
| Ex. | Chemical Structural Formula | $^1$H-NMR (DMSO-$D_6$) δ | LC-MS [M + 2H]$^{2+}$/ Rt (min) | Measurement Condition |
|---|---|---|---|---|
| 13 | 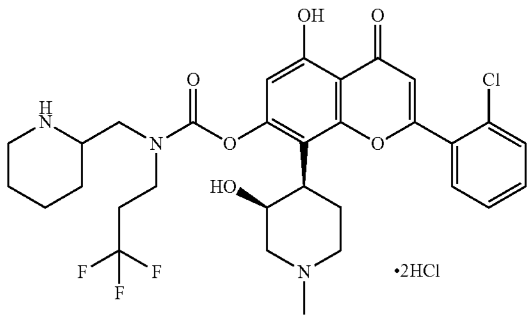 [SMILES: CN1CC[C@H](c2c(OC(=O)N(CCC(F)(F)F)CC3CCCCN3)cc(O)c3c(=O)cc(-c4ccccc4Cl)oc23)[C@H](O)C1] | 12.95-12.82 (1H, m), 9.99-8.58 (3H, m), 7.97-7.83 (1H, m), 7.71 (1H, d, J = 7.9 Hz), 7.69-7.56 (2H, m), 6.96-6.74 (2H, m), 5.66-5.52 (1H, m), 4.07-2.63 (19H, m), 1.94-1.32 (6H, m), 1.28-1.10 (1H, m). | 320/ 0.760 | A |
| 14 | 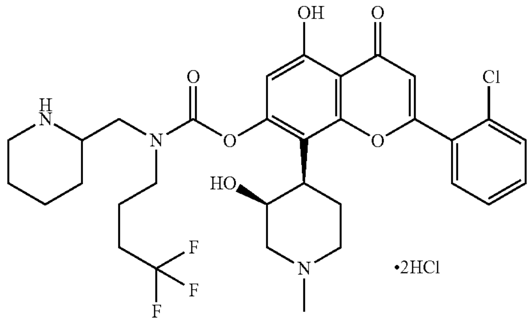 [SMILES: CN1CC[C@H](c2c(OC(=O)N(CCCC(F)(F)F)CC3CCCCN3)cc(O)c3c(=O)cc(-c4ccccc4Cl)oc23)[C@H](O)C1] | 12.99-12.83 (1H, m), 9.69-8.41 (3H, m), 7.94-7.86 (1H, m), 7.75-7.66 (1H, m), 7.66-7.48 (2H, m), 6.95-6.75 (2H, m), 5.69-5.53 (1H, m), 4.10-3.77 (2H, m), 3.70-2.80 (14H, m), 2.76-2.67 (3H, m), 2.40-1.06 (9H, m). | 327/ 0.832 | A |
| 15 | 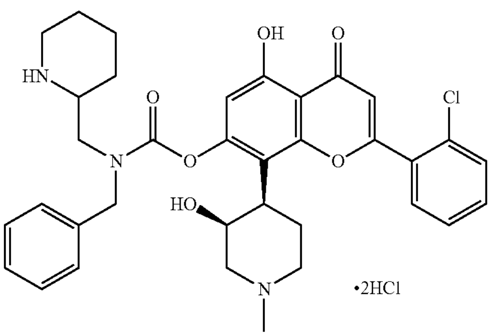 [SMILES: CN1CC[C@H](c2c(OC(=O)N(Cc3ccccc3)CC3CCCCN3)cc(O)c3c(=O)cc(-c4ccccc4Cl)oc23)[C@H](O)C1] | 12.98-12.87 (1H, m), 9.57-8.66 (3H, m), 7.86 (1H, d, J = 7.3 Hz), 7.76-7.54 (3H, m), 7.50-7.28 (5H, m), 6.92-6.72 (2H, m), 5.70-5.47 (1H, m), 4.92-4.37 (2H, m), 4.04-3.90 (1H, m), 3.79-3.06 (8H, m), 3.02-2.80 (3H, m), 2.76-2.59 (3H, m), 1.89-1.56 (5H, m), 1.54-1.34 (2H, m). | 317/ 1.074 | A |

Examples 16 to 22

The compounds shown in Table 7 were obtained by conducting the reaction and work-up described in Reference Example 1, Reference Example 2, Reference Example 3, Reference Example 9, Reference Example 19, Reference Example 25, Example 1 and Example 7 using the corresponding raw material compounds.

TABLE 7

| Ex. | Chemical Structural Formula | $^1$H-NMR (DMSO-$D_6$) δ | LC-MS $[M + 2H]^{2+}$/ Rt (min) | Measurement Condition |
|---|---|---|---|---|
| 16 | 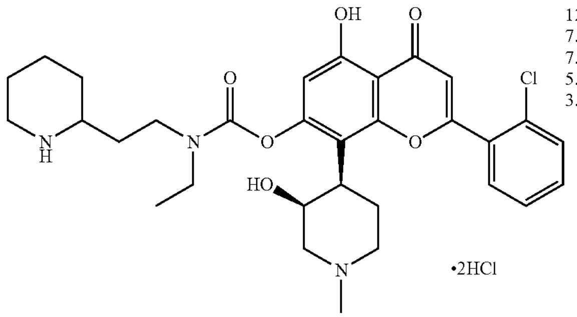 | 12.91-12.81 (1H, m), 9.69-8.62 (3H, m), 7.91-7.82 (1H, m), 7.74-7.69 (1H, m), 7.68-7.57 (2H, m), 6.79-6.62 (2H, m), 5.65-5.49 (1H, m), 4.07-3.97 (1H, m), 3.83-2.62 (16H, m), 2.19-1.10 (12H, m). | 293/ 0.866 | A |
| 17 | 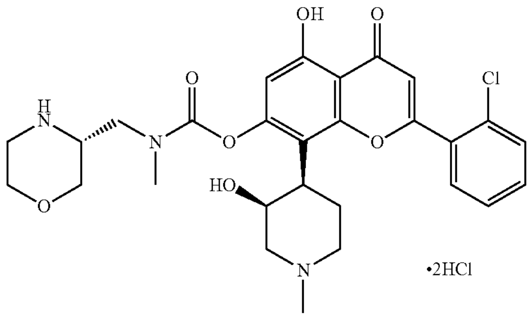 [SMILES: CN1CC[C@H](c2c(OC(=O)N(C)C[C@@H]3COCCN3)cc(O)c3c(=O)cc(-c4ccccc4Cl)oc23)[C@H](O)C1] | 12.86 (1H, s), 10.10-8.39 (3H, m), 7.89 (1H, dd, J = 7.3, 1.8 Hz), 7.73-7.69 (1H, m), 7.69-7.56 (2H, m), 6.97-6.74 (2H, m), 5.68-5.53 (1H, m), 4.14-2.81 (19H, m), 2.77-2.63 (3H, m), 1.94-1.77 (1H, m). | 280/ 0.621 | A |
| 18 | 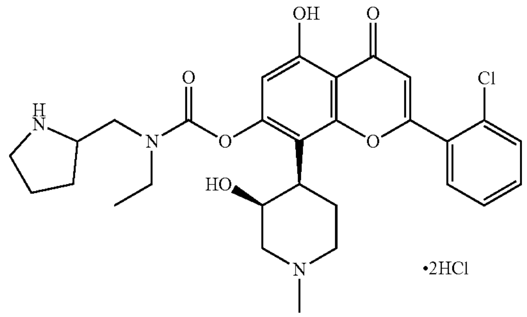 [SMILES: CCN(CC1CCCN1)C(=O)Oc1cc(O)c2c(=O)cc(-c3ccccc3Cl)oc2c1[C@H]1CCN(C)C[C@H]1O] | 12.94-12.81 (1H, m), 10.15-8.51 (3H, m), 7.88 (1H, d, J = 7.3 Hz), 7.71 (1H, dd, J = 7.9, 1.2 Hz), 7.69-7.57 (2H, m), 6.88-6.75 (2H, m), 5.71-5.51 (1H, m), 4.00 (1H, s), 3.78-2.87 (13H, m), 2.78-2.67 (3H, m), 2.16-1.51 (5H, m), 1.28-1.09 (3H, m). | 279/ 0.527 | A |
| 19 | 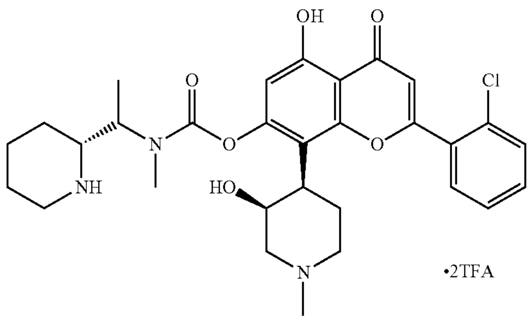 [SMILES: CC([C@H]1CCCCN1)N(C)C(=O)Oc1cc(O)c2c(=O)cc(-c3ccccc3Cl)oc2c1[C@H]1CCN(C)C[C@H]1O] | 12.93-12.81 (1H, m), 9.33 (1H, brs), 8.70-8.43 (2H, m), 7.88-7.79 (1H, m), 7.75-7.69 (1H, m), 7.69-7.63 (1H, m), 7.62-7.56 (1H, m), 6.94-6.74 (2H, m), 5.71-5.47 (1H, m), 4.20-3.96 (2H, m), 3.47-2.82 (11H, m), 2.78-2.68 (3H, m), 2.00-1.08 (13H, m). | 286/ 0.694 | A |

TABLE 7-continued
| Ex. | Chemical Structural Formula | $^1$H-NMR (DMSO-$D_6$) δ | LC-MS $[M + 2H]^{2+}$/ Rt (min) | Measurement Condition |
|---|---|---|---|---|
| 20 | 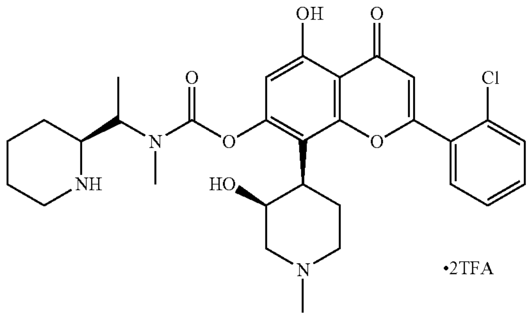 [SMILES: CC([C@@H]1CCCCN1)N(C)C(=O)Oc1cc(O)c2c(=O)cc(-c3ccccc3Cl)oc2c1[C@H]1CCN(C)C[C@H]1O] •2TFA | 12.93-12.82 (1H, m), 9.38-9.23 (1H, m), 8.63-8.32 (2H, m), 7.88-7.79 (1H, m), 7.74-7.51 (3H, m), 6.96-6.84 (2H, m), 5.67-5.47 (1H, m), 4.41-3.99 (2H, m), 3.63-2.86 (11H, m), 2.79-2.68 (3H, m), 2.02-1.03 (13H, m). | 286/ 0.638 | A |
| 21 | 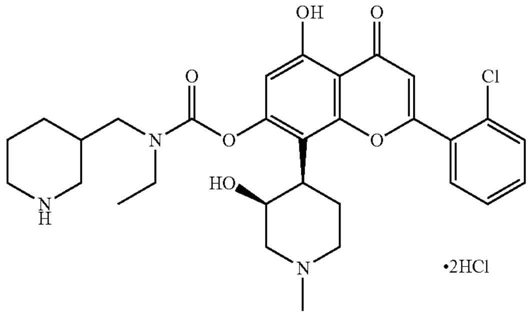 [SMILES: CCN(CC1CCCNC1)C(=O)Oc1cc(O)c2c(=O)cc(-c3ccccc3Cl)oc2c1[C@H]1CCN(C)C[C@H]1O] •2HCl | 12.90-12.86 (1H, m), 9.59 (1H, brs), 9.28-8.88 (2H, m), 7.87 (1H, d, J = 7.3 Hz), 7.71 (1H, dd, J = 7.9, 1.2 Hz), 7.68-7.58 (2H, m), 6.79-6.64 (2H, m), 5.65-5.56 (1H, m), 4.00 (1H, s), 3.61-2.91 (13H, m), 2.82-2.55 (4H, m), 2.30-2.13 (1H, m), 1.91-1.62 (3H, m), 1.32-1.10 (5H, m). | 286/ 0.796 | A |
| 22 | 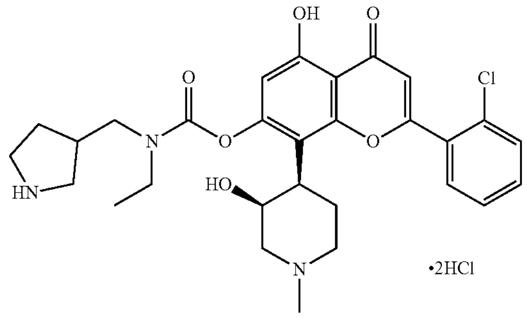 [SMILES: CCN(CC1CCNC1)C(=O)Oc1cc(O)c2c(=O)cc(-c3ccccc3Cl)oc2c1[C@H]1CCN(C)C[C@H]1O] •2HCl | 12.87 (1H, s), 9.67-8.91 (3H, m), 7.87 (1H, dd, J = 7.6, 1.5 Hz), 7.71 (1H, dd, J = 7.9, 1.8 Hz), 7.69-7.58 (2H, m), 6.84-6.53 (2H, m), 5.61 (1H, s), 3.99 (1H, s), 3.81-2.57 (17H, m), 2.15-1.50 (4H, m), 1.29-1.08 (3H, m). | 279/ 0.871 | A |

Experimental Examples

The test results for representative compounds of the present disclosure are shown below, and the chemical characteristics, pharmacokinetics and drug efficacy of the compounds are explained, but the present disclosure is not limited to these experimental examples.

Description of Compounds of Comparative Examples

In the following Experimental Examples, comparative tests were conducted with compounds described in Patent Documents 1 to 3. The compounds used as comparative examples are as follows.

TABLE 8

| Comparative Example | Chemical Structural Formula | Patent Document |
|---|---|---|
| Comparative Example 1 | 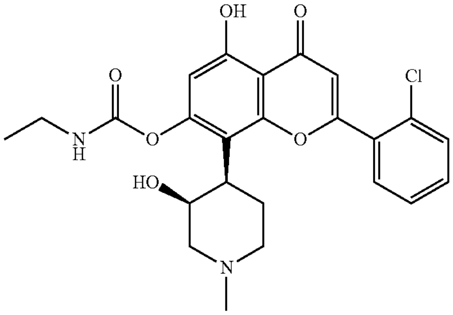 [SMILES: CCNC(=O)Oc1cc(O)c2c(=O)cc(-c3ccccc3Cl)oc2c1[C@H]1CCN(C)C[C@H]1O] | Patent Document 2 Compound 8 |
| Comparative Example 2 | 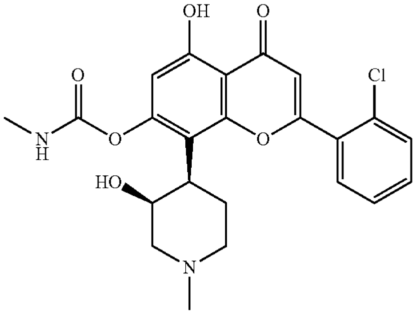 [SMILES: CNC(=O)Oc1cc(O)c2c(=O)cc(-c3ccccc3Cl)oc2c1[C@H]1CCN(C)C[C@H]1O] | Patent Document 2 Compound 9 |
| Comparative Example 3 | 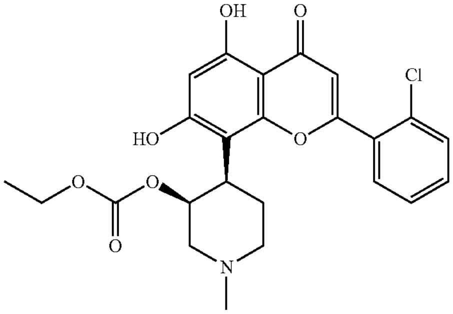 [SMILES: CCOC(=O)O[C@@H]1CN(C)CC[C@@H]1c1c(O)cc(O)c2c(=O)cc(-c3ccccc3Cl)oc12] | Patent Document 2 Compound 10 |
| Comparative Example 4 | 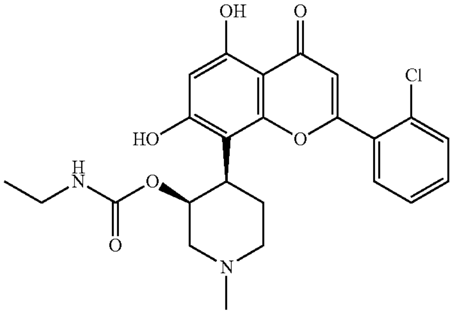 [SMILES: CCNC(=O)O[C@@H]1CN(C)CC[C@@H]1c1c(O)cc(O)c2c(=O)cc(-c3ccccc3Cl)oc12] | Patent Document 2 Compound 12 |

TABLE 8-continued
| Comparative Example | Chemical Structural Formula | Patent Document |
|---|---|---|
| Comparative Example 5 | 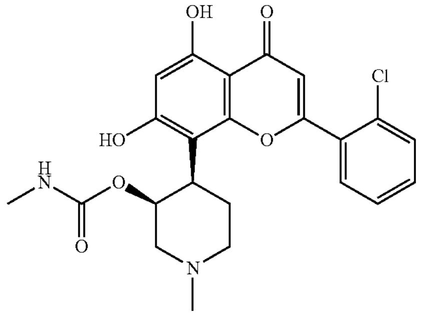 [SMILES: CNC(=O)O[C@@H]1CN(C)CC[C@@H]1c1c(O)cc(O)c2c(=O)cc(-c3ccccc3Cl)oc12] | Patent Document 2 Compound 13 |
| Comparative Example 6 | 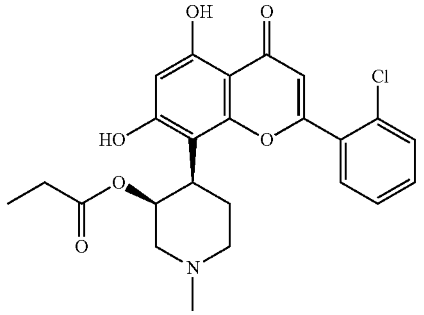 [SMILES: CCC(=O)O[C@@H]1CN(C)CC[C@@H]1c1c(O)cc(O)c2c(=O)cc(-c3ccccc3Cl)oc12] | Patent Document 2 Compound 16 |
| Comparative Example 7 | 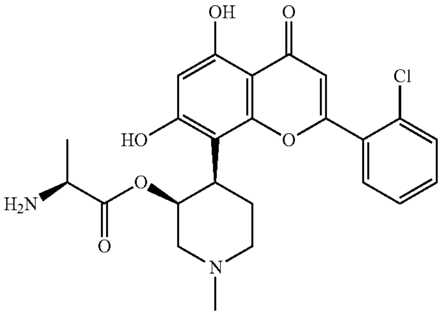 [SMILES: C[C@H](N)C(=O)O[C@@H]1CN(C)CC[C@@H]1c1c(O)cc(O)c2c(=O)cc(-c3ccccc3Cl)oc12] | Patent Document 2 Compound 27 |
| Comparative Example 8 | 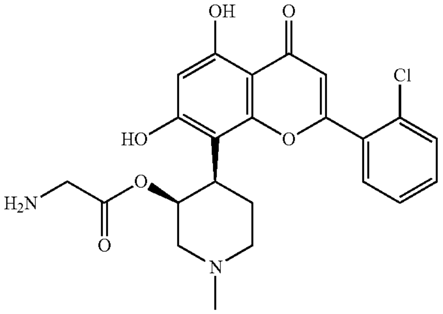 [SMILES: CN1CC[C@H](c2c(O)cc(O)c3c(=O)cc(-c4ccccc4Cl)oc23)[C@H](OC(=O)CN)C1] | Patent Document 2 Compound 28 |
| Comparative Example 9 | 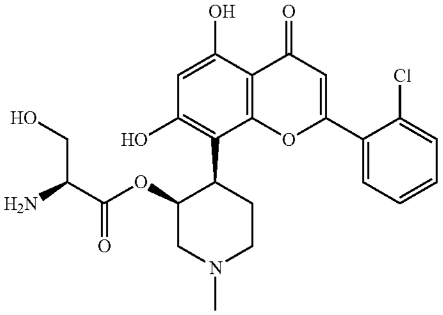 [SMILES: CN1CC[C@H](c2c(O)cc(O)c3c(=O)cc(-c4ccccc4Cl)oc23)[C@H](OC(=O)[C@@H](N)CO)C1] | Patent Document 2 Compound 29 |

TABLE 8-continued
| Comparative Example | Chemical Structural Formula | Patent Document |
| --- | --- | --- |
| Comparative Example 10 | 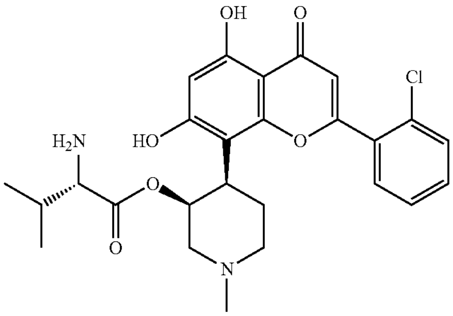 [SMILES: CC(C)[C@H](N)C(=O)O[C@@H]1CN(C)CC[C@@H]1c1c(O)cc(O)c2c(=O)cc(-c3ccccc3Cl)oc12] | Patent Document 2 Compound 30 |
| Comparative Example 11 | 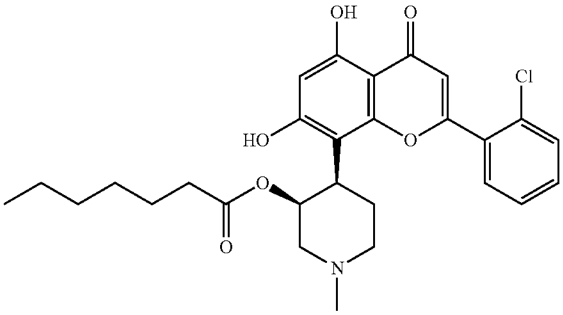 [SMILES: CCCCCCC(=O)O[C@@H]1CN(C)CC[C@@H]1c1c(O)cc(O)c2c(=O)cc(-c3ccccc3Cl)oc12] | Patent Document 2 Compound 31 |
| Comparative Example 12 | 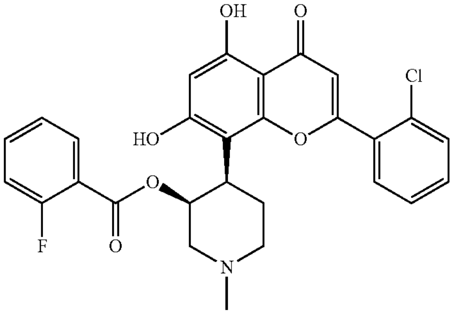 [SMILES: CN1CC[C@H](c2c(O)cc(O)c3c(=O)cc(-c4ccccc4Cl)oc23)[C@H](OC(=O)c2ccccc2F)C1] | Patent Document 2 Compound 34 |
| Comparative Example 13 | 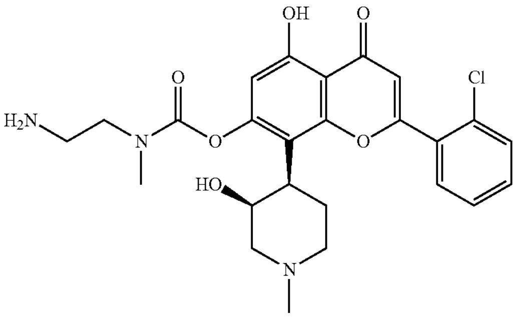 [SMILES: CN1CC[C@H](c2c(OC(=O)N(C)CCN)cc(O)c3c(=O)cc(-c4ccccc4Cl)oc23)[C@H](O)C1] | Patent Document 3 Example 8 |

TABLE 8-continued

| Comparative Example | Chemical Structural Formula | Patent Document |
|---|---|---|
| Comparative Example 14 | 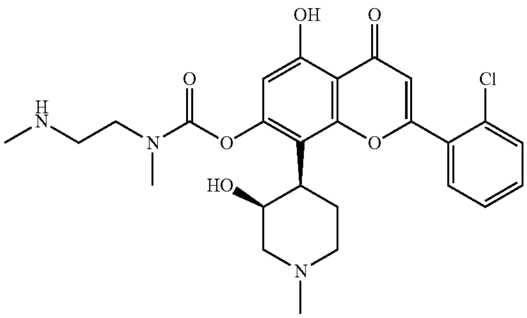 [SMILES: CNCCN(C)C(=O)Oc1cc(O)c2c(=O)cc(-c3ccccc3Cl)oc2c1[C@H]1CCN(C)C[C@H]1O] | Patent Document 3 Example 10 |

Experimental Example 1. Evaluation of Conversion Rate to Active Form in Buffer Solution For Examples 1 to 16 and Comparative Examples 1 to 14, the attrition rate of the test compound and the conversion rate of the test compound to Alvocidib in a buffer solution were calculated by the following method.

Examples 1 to 16 and Comparative Examples 1 to 14 were each left in buffer solutions adjusted to pH 5.0, 5.5, 6.0, 6.5, 7.0 and 7.4, respectively, at a concentration of 25 umol/L at 37° C. After 0, 0.5, 1, 2 and 3 hours, the residual rates of the compounds of Examples 1 to 22 and Comparative Examples 3 to 14 and the production rate of Alvocidib were determined by HPLC.

The buffer solutions used at each pH are as follows.

pH 5.0: 50 mM citrate buffer solution (pH 5.0)
pH 5.5: 50 mM citrate buffer solution (pH 5.5)
pH 6.0: 50 mM phosphate buffer solution (pH 6.0)
pH 6.5: 50 mM phosphate buffer solution (pH 6.5)
pH 7.0: 50 mM phosphate buffer solution (pH 7.0)
pH 7.4: 50 mM phosphate buffer solution (pH 7.4)

The measurement conditions for HPLC are as follows.

<HPLC Conditions> column: Acquity UPLC BEH C18, 1.7 um, 50×2.1 mm
column temperature: 40° C.
mobile phase:
A: water containing 0.1% trifluoroacetic acid
B: acetonitrile
A/B (min): 95/5(0)→0/100(3.5)→0/100(4)→95/5(4.01)→95/5(5), or
A/B (min): 80/20(0)→70/30(3)→0/100(3.5)→0/100(4)→80/20 (4.01)→80/20(5), or
A/B (min): 80/20(0)→75/25(3)→0/100(3.5)→0/100(4)→80/20 (4.01)→80/20(5), or
A/B (min): 95/5(0)→50/50(3)→0/100(3.5)→0/100(4)→95/5(4.01)→95/5(5)
flow rate: 0.8 mL/min
detection: ultraviolet visible detector, measurement wavelength 254 nm
injection: 2 to 5 μL The test results of Experimental Example 1 are shown in Table 9 to Table 68. It was confirmed that the compounds of Example 1, Example 2, Example 3, Example 4, Example 5, Example 6, Example 7, Example 8, Example 9, Example 10, Example 11, Example 12, Example 13, Example 14, Example 15 and Example 16 were stable at pH 5 and showed a high residual rate even after 2 or 3 hours, whereas they were rapidly converted to Alvocidib at pH 7.4. In particular, it was confirmed that the compounds of Examples 1, 5, 9 and 10 were converted to Alvocidib with higher efficiency.

On the other hand, it was confirmed that the compounds of Comparative Example 1, Comparative Example 2, Comparative Example 7, Comparative Example 8, Comparative Example 9, Comparative Example 13 and Comparative Example 14 were unstable even at pH 5, and the production rate of Alvocidib increased over time within 3 hours. In particular, it was confirmed that the compounds of Comparative Example 1, Comparative Example 2 and Comparative Example 14 were unstable at pH 5 and mostly converted to Alvocidib within 3 hours. It was also confirmed that the compounds of Comparative Example 3, Comparative Example 4, Comparative Example 5, Comparative Example 6, Comparative Example 10, Comparative Example 11 and Comparative Example 12 were slowly converted to Alvocidib even at pH 7.4 and hardly converted to Alvocidib even after 3 hours.

From the above, it is shown that the compound of the present disclosure has the characteristics of being stable under acidic conditions while being rapidly degraded under neutral conditions, and therefore, it has exceptional effects as a pharmaceutical formulation, that is, it can be stored stably and can be rapidly degraded and converted to Alvocidib in the blood.

TABLE 9

(Residual rate (%) of Example 1)

| Time (hr) | 0 | 0.5 | 1 | 2 | 3 |
|---|---|---|---|---|---|
| pH5.0 | 98.7 | 98.4 | 98.1 | 97.4 | 96.9 |
| pH5.5 | 98.8 | 97.3 | 97.1 | 95.3 | 93.8 |
| pH6.0 | 99.2 | 95.5 | 92.5 | 86.8 | 81.8 |
| pH6.5 | 98.4 | 90.2 | 82.0 | 68.4 | 57.7 |
| pH7.0 | 98.9 | 75.0 | 57.8 | 33.5 | 21.0 |
| pH7.4 | 98.5 | 53.8 | 29.3 | 11.3 | 6.9 |

TABLE 10

(Production rate (%) of Alvocidib from Example 1)

| Time (hr) | 0 | 0.5 | 1 | 2 | 3 |
|---|---|---|---|---|---|
| pH5.0 | 0.0 | 0.4 | 0.7 | 1.3 | 1.8 |
| pH5.5 | 0.0 | 1.0 | 1.8 | 3.5 | 5.1 |
| pH6.0 | 0.0 | 3.3 | 6.3 | 12.0 | 17.0 |
| pH6.5 | 0.0 | 8.7 | 16.4 | 30.1 | 40.7 |
| pH7.0 | 0.0 | 23.2 | 41.1 | 65.3 | 77.1 |
| pH7.4 | 0.4 | 44.9 | 69.3 | 87.6 | 91.4 |

TABLE 11

(Residual rate (%) of Example 2)

| Time (hr) | 0 | 0.5 | 1 | 2 | 3 |
|---|---|---|---|---|---|
| pH5.0 | 95.5 | 95.4 | 95.1 | 94.7 | 94.1 |
| pH5.5 | 95.8 | 95.1 | 94.3 | 92.5 | 90.4 |
| pH6.0 | 95.5 | 93.0 | 89.6 | 81.0 | 74.5 |
| pH6.5 | 95.9 | 87.4 | 75.4 | 57.4 | 45.1 |
| pH7.0 | 95.4 | 66.7 | 44.8 | 19.9 | 9.8 |
| pH7.4 | 95.4 | 41.7 | 17.1 | 3.5 | 1.5 |

TABLE 12

(Production rate (%) of Alvocidib from Example 2)

| Time (hr) | 0 | 0.5 | 1 | 2 | 3 |
|---|---|---|---|---|---|
| pH5.0 | 0.0 | 0.3 | 0.5 | 1.1 | 1.6 |
| pH5.5 | 0.0 | 0.8 | 1.7 | 3.2 | 5.3 |
| pH6.0 | 0.0 | 2.9 | 5.7 | 11.1 | 15.7 |
| pH6.5 | 0.0 | 7.9 | 15.1 | 27.2 | 36.1 |
| pH7.0 | 0.0 | 21.0 | 38.0 | 53.4 | 60.8 |
| pH7.4 | 0.2 | 38.7 | 56.4 | 66.0 | 67.6 |

TABLE 13

(Residual rate (%) of Example 3)

| Time (hr) | 0 | 0.5 | 1 | 2 | 3 |
|---|---|---|---|---|---|
| pH5.0 | 99.8 | 99.1 | 98.7 | 97.8 | 96.9 |
| pH5.5 | 99.7 | 98.2 | 97.3 | 95.3 | 93.5 |
| pH6.0 | 99.7 | 95.5 | 92.2 | 85.3 | 79.4 |
| pH6.5 | 99.7 | 88.9 | 80.9 | 65.3 | 53.9 |
| pH7.0 | 99.4 | 72.2 | 55.3 | 20.2 | 8.0 |
| pH7.4 | 99.1 | 49.4 | 17.0 | 0.0 | 0.0 |

TABLE 14

(Production rate (%) of Alvocidib from Example 3)

| Time (hr) | 0 | 0.5 | 1 | 2 | 3 |
|---|---|---|---|---|---|
| pH5.0 | 0.2 | 0.9 | 1.3 | 2.2 | 3.1 |
| pH5.5 | 0.3 | 1.8 | 2.7 | 4.7 | 6.5 |
| pH6.0 | 0.3 | 4.5 | 7.6 | 14.1 | 19.8 |
| pH6.5 | 0.3 | 10.6 | 18.3 | 33.5 | 44.6 |
| pH7.0 | 0.6 | 26.8 | 43.2 | 65.2 | 74.5 |
| pH7.4 | 0.9 | 49.0 | 67.8 | 80.4 | 82.5 |

TABLE 15

(Residual rate (%) of Example 4)

| Time (hr) | 0 | 0.5 | 1 | 2 | 3 |
|---|---|---|---|---|---|
| pH5.0 | 99.3 | 98.5 | 98.0 | 96.8 | 95.6 |
| pH5.5 | 99.2 | 97.1 | 95.5 | 91.4 | 87.9 |
| pH6.0 | 99.3 | 91.9 | 85.6 | 72.4 | 61.7 |
| pH6.5 | 99.3 | 79.5 | 65.1 | 39.7 | 24.9 |
| pH7.0 | 98.8 | 51.3 | 27.7 | 0.0 | 0.0 |
| pH7.4 | 98.4 | 21.5 | 0.0 | 0.0 | 0.0 |

TABLE 16

(Production rate (%) of Alvocidib from Example 4)

| Time (hr) | 0 | 0.5 | 1 | 2 | 3 |
|---|---|---|---|---|---|
| pH5.0 | 0.5 | 0.8 | 1.1 | 1.7 | 2.3 |
| pH5.5 | 0.4 | 1.5 | 2.2 | 4.0 | 5.5 |
| pH6.0 | 0.4 | 3.7 | 6.4 | 12.0 | 16.6 |
| pH6.5 | 0.5 | 9.0 | 15.1 | 26.1 | 32.7 |
| pH7.0 | 0.6 | 21.3 | 31.6 | 41.1 | 43.3 |
| pH7.4 | 0.8 | 34.8 | 42.0 | 44.6 | 44.6 |

TABLE 17

(Residual rate (%) of Example 5)

| Time (hr) | 0 | 0.5 | 1 | 2 | 3 |
|---|---|---|---|---|---|
| pH5.0 | 98.7 | 98.3 | 97.8 | 96.7 | 95.8 |
| pH5.5 | 98.3 | 97.2 | 96.4 | 94.5 | 92.7 |
| pH6.0 | 98.7 | 95.2 | 92.2 | 85.7 | 79.8 |
| pH6.5 | 98.4 | 88.9 | 80.9 | 65.5 | 52.6 |
| PH7.0 | 98.4 | 72.7 | 55.0 | 28.7 | 15.0 |
| pH7.4 | 98.7 | 49.4 | 25.9 | 5.9 | 1.5 |

TABLE 18

(Production rate (%) of Alvocidib from Example 5)

| Time (hr) | 0 | 0.5 | 1 | 2 | 3 |
|---|---|---|---|---|---|
| pH5.0 | 0.0 | 0.6 | 1.1 | 2.3 | 3.4 |
| pH5.5 | 0.0 | 1.2 | 2.1 | 3.9 | 5.7 |
| pH6.0 | 0.0 | 3.6 | 6.6 | 12.8 | 18.6 |
| pH6.5 | 0.0 | 9.5 | 17.1 | 32.1 | 44.2 |
| pH7.0 | 0.0 | 25.0 | 41.9 | 66.7 | 79.9 |
| pH7.4 | 0.0 | 47.5 | 69.8 | 88.9 | 93.2 |

TABLE 19

(Residual rate (%) of Example 6)

| Time (hr) | 0 | 0.5 | 1 | 2 | 3 |
|---|---|---|---|---|---|
| pH5.0 | 99.3 | 99.1 | 98.7 | 97.8 | 96.8 |
| pH5.5 | 99.5 | 98.1 | 97.0 | 94.2 | 91.9 |
| pH6.0 | 99.4 | 94.8 | 90.7 | 82.5 | 75.2 |
| pH6.5 | 99.4 | 86.6 | 75.3 | 56.9 | 42.3 |
| pH7.0 | 99.3 | 63.7 | 40.4 | 16.1 | 6.8 |
| pH7.4 | 99.1 | 36.3 | 12.7 | 2.7 | 0.7 |

TABLE 20

| (Production rate (%) of Alvocidib from Example 6) | | | | | |
|---|---|---|---|---|---|
| Time (hr) | 0 | 0.5 | 1 | 2 | 3 |
| pH5.0 | 0.5 | 0.9 | 1.3 | 2.0 | 2.6 |
| pH5.5 | 0.5 | 1.6 | 2.5 | 4.3 | 6.2 |
| pH6.0 | 0.6 | 4.0 | 7.1 | 13.2 | 18.6 |
| pH6.5 | 0.6 | 10.1 | 18.6 | 31.9 | 42.8 |
| pH7.0 | 0.7 | 27.0 | 44.4 | 62.8 | 69.8 |
| pH7.4 | 0.9 | 47.8 | 65.7 | 73.6 | 75.3 |

TABLE 21

| (Residual rate (%) of Example 7) | | | | | |
|---|---|---|---|---|---|
| Time (hr) | 0 | 0.5 | 1 | 2 | 3 |
| pH5.0 | 100.0 | 100.0 | 100.0 | 98.5 | 97.7 |
| pH5.5 | 100.0 | 98.8 | 98.0 | 96.2 | 94.9 |
| pH6.0 | 98.9 | 96.0 | 94.6 | 87.5 | 83.4 |
| pH6.5 | 96.7 | 87.6 | 84.0 | 73.2 | 64.8 |
| pH7.0 | 89.1 | 72.7 | 62.0 | 47.1 | 29.5 |
| pH7.4 | 81.0 | 49.8 | 39.2 | 31.0 | 19.0 |

TABLE 22

| (Production rate (%) of Alvocidib from Example 7) | | | | | |
|---|---|---|---|---|---|
| Time (hr) | 0 | 0.5 | 1 | 2 | 3 |
| pH5.0 | 0.0 | 0.0 | 0.0 | 1.5 | 2.3 |
| pH5.5 | 0.0 | 1.2 | 2.0 | 3.8 | 5.1 |
| pH6.0 | 1.1 | 4.0 | 5.4 | 12.5 | 16.6 |
| pH6.5 | 3.3 | 12.4 | 16.0 | 26.8 | 35.2 |
| pH7.0 | 10.9 | 27.3 | 38.0 | 52.9 | 70.5 |
| pH7.4 | 19.0 | 50.2 | 60.8 | 69.0 | 81.0 |

TABLE 23

| (Residual rate (%) of Example 8) | | | | | |
|---|---|---|---|---|---|
| Time (hr) | 0 | 0.5 | 1 | 2 | 3 |
| pH5.0 | 95.4 | 95.1 | 95.0 | 94.7 | — |
| pH5.5 | 95.9 | 95.0 | 94.3 | 93.4 | — |
| pH6.0 | 95.7 | 92.1 | 89.4 | 86.5 | — |
| pH6.5 | 95.0 | 85.3 | 77.7 | 71.2 | — |
| pH7.0 | 92.5 | 69.3 | 56.7 | 49.0 | — |
| pH7.4 | 86.7 | 51.4 | 41.7 | 38.4 | — |

TABLE 24

| (Production rate (%) of Alvocidib from Example 8) | | | | | |
|---|---|---|---|---|---|
| Time (hr) | 0 | 0.5 | 1 | 2 | 3 |
| pH5.0 | 0.7 | 1.2 | 1.6 | 2.0 | — |
| pH5.5 | 0.5 | 1.6 | 2.5 | 3.5 | — |
| pH6.0 | 0.8 | 4.4 | 7.3 | 10.3 | — |
| pH6.5 | 1.5 | 11.2 | 18.9 | 25.6 | — |
| pH7.0 | 4.0 | 27.3 | 40.0 | 48.2 | — |
| pH7.4 | 9.7 | 45.1 | 55.2 | 58.2 | — |

TABLE 25

| (Residual rate (%) of Example 9) | | | | | |
|---|---|---|---|---|---|
| Time (hr) | 0 | 0.5 | 1 | 2 | 3 |
| pH5.0 | 96.2 | 95.9 | 95.6 | 94.9 | 94.0 |
| pH5.5 | 96.2 | 95.2 | 94.4 | 92.5 | 90.5 |
| pH6.0 | 96.2 | 92.9 | 89.5 | 83.0 | 76.6 |
| pH6.5 | 95.9 | 86.4 | 77.3 | 61.9 | 48.4 |
| pH7.0 | 95.4 | 73.1 | 55.1 | 31.0 | 16.7 |
| pH7.4 | 94.3 | 48.7 | 23.7 | 5.6 | 1.1 |

TABLE 26

| (Production rate (%) of Alvocidib from Example 9) | | | | | |
|---|---|---|---|---|---|
| Time (hr) | 0 | 0.5 | 1 | 2 | 3 |
| pH5.0 | 1.4 | 1.7 | 2.1 | 2.8 | 3.6 |
| pH5.5 | 1.4 | 2.4 | 3.4 | 5.2 | 7.2 |
| pH6.0 | 1.5 | 4.9 | 8.2 | 14.4 | 20.8 |
| pH6.5 | 1.7 | 11.2 | 20.2 | 35.4 | 49.0 |
| pH7.0 | 2.2 | 24.1 | 42.0 | 66.1 | 81.0 |
| pH7.4 | 3.4 | 48.7 | 73.6 | 92.4 | 96.7 |

TABLE 27

| (Residual rate (%) of Example 10) | | | | | |
|---|---|---|---|---|---|
| Time (hr) | 0 | 0.5 | 1 | 2 | 3 |
| pH5.0 | 90.6 | 90.4 | 90.8 | 90.1 | 89.5 |
| pH5.5 | 90.7 | 90.4 | 89.5 | 87.9 | 86.3 |
| pH6.0 | 90.7 | 88.2 | 85.2 | 79.4 | 74.1 |
| pH6.5 | 91.3 | 82.4 | 73.9 | 59.6 | 47.1 |
| pH7.0 | 90.7 | 70.0 | 52.8 | 29.6 | 0.8 |
| pH7.4 | 89.9 | 46.5 | 22.6 | 0.9 | 0.8 |

TABLE 28

| (Production rate (%) of Alvocidib from Example 10) | | | | | |
|---|---|---|---|---|---|
| Time (hr) | 0 | 0.5 | 1 | 2 | 3 |
| pH5.0 | 1.6 | 2.1 | 2.5 | 3.1 | 3.9 |
| pH5.5 | 1.6 | 2.7 | 3.6 | 5.4 | 7.2 |
| pH6.0 | 1.7 | 4.9 | 8.1 | 14.1 | 19.8 |
| pH6.5 | 1.9 | 10.8 | 19.4 | 34.6 | 46.2 |
| pH7.0 | 2.2 | 22.8 | 40.0 | 63.6 | 76.4 |
| pH7.4 | 3.1 | 46.1 | 71.5 | 87.2 | 91.6 |

TABLE 29

| (Residual rate (%) of Example 11) | | | | | |
|---|---|---|---|---|---|
| Time (hr) | 0 | 0.5 | 1 | 2 | 3 |
| pH5.0 | 83.2 | 82.7 | 81.3 | 80.5 | 79.1 |
| pH5.5 | 83.6 | 81.8 | 79.2 | 75.0 | 70.2 |
| pH6.0 | 83.7 | 76.0 | 66.6 | 49.8 | 44.8 |
| pH6.5 | 81.4 | 60.4 | 35.6 | 23.7 | 21.4 |
| pH7.0 | 80.0 | 30.1 | 22.0 | 17.1 | 12.4 |
| pH7.4 | 79.7 | 16.2 | 16.7 | 16.2 | 15.9 |

TABLE 30

(Production rate (%) of Alvocidib from Example 11)

| Time (hr) | 0 | 0.5 | 1 | 2 | 3 |
|---|---|---|---|---|---|
| pH5.0 | 0.2 | 0.9 | 1.8 | 3.3 | 4.8 |
| pH5.5 | 0.2 | 2.5 | 4.8 | 9.4 | 14.0 |
| pH6.0 | 0.3 | 8.5 | 16.9 | 32.6 | 39.4 |
| pH6.5 | 0.8 | 23.6 | 46.5 | 60.2 | 62.7 |
| pH7.0 | 2.1 | 53.4 | 62.1 | 67.0 | 71.6 |
| pH7.4 | 4.6 | 68.3 | 67.0 | 67.9 | 67.3 |

TABLE 31

(Residual rate (%) of Example 12)

| Time (hr) | 0 | 0.5 | 1 | 2 | 3 |
|---|---|---|---|---|---|
| pH5.0 | 80.7 | 80.3 | 79.6 | 79.6 | 77.3 |
| pH5.5 | 80.6 | 79.9 | 77.5 | 73.8 | 71.2 |
| pH6.0 | 80.8 | 75.4 | 70.3 | 56.2 | 54.0 |
| pH6.5 | 80.4 | 63.8 | 39.4 | 26.2 | 13.4 |
| pH7.0 | 80.2 | 35.8 | 15.4 | 0.0 | 0.0 |
| pH7.4 | 77.3 | 10.8 | 0.0 | 0.0 | 0.0 |

TABLE 32

(Production rate (%) of Alvocidib from Example 12)

| Time (hr) | 0 | 0.5 | 1 | 2 | 3 |
|---|---|---|---|---|---|
| pH5.0 | 0.5 | 1.1 | 1.5 | 2.3 | 3.9 |
| pH5.5 | 0.5 | 1.9 | 3.8 | 6.9 | 9.8 |
| pH6.0 | 0.6 | 6.2 | 11.0 | 22.5 | 26.9 |
| pH6.5 | 1.0 | 16.6 | 31.8 | 40.5 | 52.2 |
| pH7.0 | 1.7 | 33.8 | 51.2 | 60.2 | 62.7 |
| pH7.4 | 3.9 | 51.0 | 65.9 | 67.3 | 63.6 |

TABLE 33

(Residual rate (%) of Example 13)

| Time (hr) | 0 | 0.5 | 1 | 2 | 3 |
|---|---|---|---|---|---|
| pH5.0 | 82.1 | 81.7 | 80.3 | 78.0 | 76.1 |
| pH5.5 | 82.7 | 79.2 | 74.6 | 67.1 | 61.8 |
| pH6.0 | 81.3 | 69.8 | 56.6 | 40.2 | 28.3 |
| pH6.5 | 81.4 | 47.7 | 22.2 | 9.9 | 2.8 |
| pH7.0 | 78.3 | 18.7 | 2.7 | 0.4 | 0.0 |
| pH7.4 | 68.5 | 2.2 | 0.2 | 0.0 | 0.0 |

TABLE 34

(Production rate (%) of Alvocidib from Example 13)

| Time (hr) | 0 | 0.5 | 1 | 2 | 3 |
|---|---|---|---|---|---|
| pH5.0 | 2.1 | 3.9 | 4.9 | 6.3 | 8.0 |
| pH5.5 | 2.5 | 5.5 | 8.6 | 13.9 | 17.7 |
| pH6.0 | 3.3 | 11.6 | 21.6 | 33.3 | 42.5 |
| pH6.5 | 3.7 | 27.5 | 47.7 | 56.7 | 65.5 |
| pH7.0 | 5.4 | 49.3 | 65.9 | 65.1 | 69.9 |
| pH7.4 | 9.2 | 65.8 | 65.5 | 68.6 | 66.1 |

TABLE 35

(Residual rate (%) of Example 14)

| Time (hr) | 0 | 0.5 | 1 | 2 | 3 |
|---|---|---|---|---|---|
| pH5.0 | 56.6 | 54.6 | 53.0 | 51.0 | 52.7 |
| pH5.5 | 57.5 | 55.8 | 54.3 | 48.6 | 47.7 |
| pH6.0 | 55.8 | 49.7 | 44.8 | 31.8 | 24.5 |
| pH6.5 | 52.2 | 35.2 | 22.9 | 14.0 | 5.1 |
| pH7.0 | 53.4 | 16.3 | 8.4 | 1.1 | 0.4 |
| pH7.4 | 45.8 | 4.6 | 0.7 | 0.2 | 0.3 |

TABLE 36-1

(Production rate (%) of Alvocidib from Example 14)

| Time (hr) | 0 | 0.5 | 1 | 2 | 3 |
|---|---|---|---|---|---|
| pH5.0 | 29.2 | 29.9 | 31.7 | 33.1 | 33.4 |
| pH5.5 | 29.0 | 30.9 | 32.7 | 35.4 | 37.9 |
| pH6.0 | 29.1 | 34.4 | 39.1 | 50.2 | 55.9 |
| pH6.5 | 31.6 | 45.8 | 57.1 | 63.0 | 72.6 |
| pH7.0 | 30.7 | 62.0 | 68.0 | 75.5 | 75.2 |
| pH7.4 | 35.9 | 71.6 | 76.6 | 75.6 | 75.7 |

Example 14, tested in Experimental Example 1, was obtained as a mixture with 28.2% Alvocidib. In order to clarify the Alvocidib amount produced dependent on pH in Table 36-1, Table 36-2 was prepared by subtracting the said 28.2% from the total.

TABLE 36-2

| Time (hr) | 0 | 0.5 | 1 | 2 | 3 |
|---|---|---|---|---|---|
| pH5.0 | 1.0 | 1.7 | 3.5 | 4.9 | 5.2 |
| pH5.5 | 0.8 | 2.7 | 4.5 | 7.2 | 9.7 |
| pH6.0 | 0.9 | 6.2 | 10.9 | 22.0 | 27.7 |
| pH6.5 | 3.4 | 17.6 | 28.9 | 34.8 | 44.4 |
| pH7.0 | 2.5 | 33.8 | 39.8 | 47.3 | 47.0 |
| PH7.4 | 7.7 | 43.4 | 48.4 | 47.4 | 47.5 |

TABLE 37

(Residual rate (%) of Example 15)

| Time (hr) | 0 | 0.5 | 1 | 2 | 3 |
|---|---|---|---|---|---|
| pH5.0 | 95.6 | 95.2 | 94.7 | 93.5 | 92.5 |
| pH5.5 | 95.6 | 94.2 | 92.7 | 89.5 | 87.8 |
| pH6.0 | 95.5 | 91.0 | 84.7 | 62.8 | 56.7 |
| pH6.5 | 94.8 | 82.2 | 56.3 | 32.9 | 24.3 |
| pH7.0 | 94.1 | 38.5 | 7.1 | 3.8 | 3.9 |
| PH7.4 | 92.2 | 21.1 | 8.0 | 3.1 | 2.9 |

TABLE 38

(Production rate (%) of Alvocidib from Example 15)

| Time (hr) | 0 | 0.5 | 1 | 2 | 3 |
|---|---|---|---|---|---|
| pH5.0 | 1.4 | 1.9 | 2.6 | 3.8 | 4.6 |
| pH5.5 | 1.4 | 2.8 | 4.5 | 7.8 | 9.5 |
| pH6.0 | 1.5 | 6.2 | 12.4 | 22.3 | 25.7 |
| pH6.5 | 1.9 | 15.1 | 26.1 | 44.6 | 52.4 |
| pH7.0 | 2.8 | 40.7 | 56.9 | 69.8 | 69.9 |
| pH7.4 | 4.8 | 54.7 | 67.3 | 75.2 | 77.2 |

TABLE 39

| (Residual rate (%) of Example 16) | | | | | |
|---|---|---|---|---|---|
| Time (hr) | 0 | 0.5 | 1 | 2 | 3 |
| pH5.0 | 84.3 | 84.9 | 86.4 | 86.1 | 86.1 |
| pH5.5 | 84.9 | 85.8 | 86.3 | 85.7 | 86.6 |
| pH6.0 | 85.3 | 84.3 | 71.7 | 63.0 | 55.6 |
| pH6.5 | 86.0 | 67.6 | 61.4 | 37.4 | 34.9 |
| pH7.0 | 86.2 | 54.8 | 35.7 | 16.9 | 7.7 |
| pH7.4 | 85.3 | 23.2 | 5.9 | 2.2 | 0.0 |

TABLE 40

| (Production rate (%) of Alvocidib from Example 16) | | | | | |
|---|---|---|---|---|---|
| Time (hr) | 0 | 0.5 | 1 | 2 | 3 |
| pH5.0 | 0.0 | 0.0 | 0.0 | 0.0 | 0.0 |
| pH5.5 | 0.0 | 0.0 | 0.0 | 0.0 | 0.0 |
| pH6.0 | 0.0 | 0.0 | 12.8 | 21.6 | 29.3 |
| pH6.5 | 0.0 | 16.4 | 25.3 | 47.1 | 51.5 |
| PH7.0 | 0.0 | 30.5 | 50.2 | 68.6 | 78.2 |
| pH7.4 | 0.9 | 59.0 | 77.8 | 82.1 | 85.8 |

TABLE 41

| (Residual rate (%) of Comparative Example 1) | | | | | |
|---|---|---|---|---|---|
| Time (hr) | 0 | 0.5 | 1 | 2 | 3 |
| pH5.0 | 91.6 | 62.1 | 41.5 | 17.9 | 8.2 |
| pH5.5 | 91.2 | 25.3 | 7.3 | 1.1 | 0.7 |
| pH6.0 | 89.9 | 3.7 | 1.5 | 1.3 | 1.0 |
| pH6.5 | 87.1 | 1.3 | 1.0 | 1.1 | 0.8 |
| pH7.0 | 77.8 | 1.0 | 0.9 | 1.0 | 0.9 |
| pH7.4 | 59.8 | 0.9 | 1.1 | 1.0 | 0.7 |

TABLE 42

| (Production rate (%) of Alvocidib from Comparative Example 1) | | | | | |
|---|---|---|---|---|---|
| Time (hr) | 0 | 0.5 | 1 | 2 | 3 |
| pH5.0 | 8.4 | 37.9 | 58.5 | 82.1 | 91.8 |
| pH5.5 | 8.8 | 74.7 | 92.7 | 98.9 | 99.3 |
| pH6.0 | 10.1 | 96.3 | 98.3 | 98.5 | 99.0 |
| pH6.5 | 12.9 | 98.7 | 99.0 | 98.9 | 99.2 |
| pH7.0 | 22.2 | 99.0 | 99.1 | 98.8 | 99.1 |
| pH7.4 | 40.2 | 99.1 | 98.9 | 99.1 | 99.3 |

TABLE 43

| (Residual rate (%) of Comparative Example 2) | | | | | |
|---|---|---|---|---|---|
| Time (hr) | 0 | 0.5 | 1 | 2 | 3 |
| pH5.0 | 96.6 | 66.9 | 45.1 | 19.3 | 8.5 |
| pH5.5 | 96.4 | 28.0 | 7.5 | 0.6 | 0.0 |
| pH6.0 | 95.1 | 2.5 | 0.0 | 0.0 | 0.0 |
| pH6.5 | 91.5 | 0.0 | 0.0 | 0.0 | 0.0 |
| pH7.0 | 81.8 | 0.0 | 0.0 | 0.0 | 0.0 |
| pH7.4 | 63.9 | 0.0 | 0.0 | 0.0 | 0.0 |

TABLE 44

| (Production rate (%) of Alvocidib from Comparative Example 2) | | | | | |
|---|---|---|---|---|---|
| Time (hr) | 0 | 0.5 | 1 | 2 | 3 |
| pH5.0 | 2.0 | 31.8 | 53.2 | 79.0 | 90.0 |
| pH5.5 | 2.4 | 70.5 | 90.8 | 97.6 | 98.6 |
| pH6.0 | 3.3 | 95.7 | 98.2 | 98.3 | 98.6 |
| pH6.5 | 7.1 | 98.3 | 98.3 | 98.5 | 98.2 |
| pH7.0 | 17.0 | 98.6 | 98.3 | 98.3 | 98.3 |
| pH7.4 | 34.5 | 98.4 | 98.2 | 98.5 | 98.5 |

TABLE 45

| (Residual rate (%) of Comparative Example 3) | | | | | |
|---|---|---|---|---|---|
| Time (hr) | 0 | 0.5 | 1 | 2 | 3 |
| pH5.0 | 90.6 | 90.6 | 90.7 | 90.2 | 90.6 |
| pH5.5 | 90.9 | 90.9 | 90.6 | 89.9 | 90.7 |
| pH6.0 | 91.0 | 90.8 | 90.9 | 90.0 | 90.9 |
| pH6.5 | 90.8 | 90.9 | 90.8 | 89.9 | 90.8 |
| pH7.0 | 91.0 | 91.0 | 90.9 | 89.8 | 90.8 |
| pH7.4 | 91.0 | 91.0 | 91.0 | 90.1 | 90.8 |

TABLE 46

| (Production rate (%) of Alvocidib from Comparative Example 3) | | | | | |
|---|---|---|---|---|---|
| Time (hr) | 0 | 0.5 | 1 | 2 | 3 |
| pH5.0 | 1.2 | 1.2 | 1.2 | 1.3 | 1.2 |
| pH5.5 | 1.1 | 1.1 | 1.2 | 1.2 | 1.1 |
| pH6.0 | 1.1 | 1.2 | 1.1 | 1.2 | 1.2 |
| pH6.5 | 1.1 | 1.1 | 1.2 | 1.3 | 1.2 |
| pH7.0 | 1.1 | 1.2 | 1.2 | 1.4 | 1.3 |
| PH7.4 | 1.1 | 1.2 | 1.2 | 1.4 | 1.3 |

TABLE 47

| (Residual rate (%) of Comparative Example 4) | | | | | |
|---|---|---|---|---|---|
| Time (hr) | 0 | 0.5 | 1 | 2 | 3 |
| pH5.0 | 97.7 | 97.8 | 97.8 | 97.7 | 97.7 |
| pH5.5 | 97.8 | 97.6 | 97.7 | 97.8 | 97.6 |
| pH6.0 | 97.8 | 97.7 | 97.7 | 97.7 | 97.7 |
| pH6.5 | 97.7 | 97.6 | 97.7 | 97.8 | 97.7 |
| pH7.0 | 97.7 | 97.7 | 97.6 | 97.6 | 97.7 |
| pH7.4 | 97.7 | 97.6 | 97.7 | 97.7 | 97.8 |

TABLE 48

| (Production rate (%) of Alvocidib from Comparative Example 4) | | | | | |
|---|---|---|---|---|---|
| Time (hr) | 0 | 0.5 | 1 | 2 | 3 |
| pH5.0 | 1.7 | 1.8 | 1.7 | 1.8 | 1.8 |
| pH5.5 | 1.8 | 1.8 | 1.8 | 1.8 | 1.8 |
| pH6.0 | 1.8 | 1.8 | 1.7 | 1.8 | 1.8 |
| pH6.5 | 1.8 | 1.8 | 1.8 | 1.8 | 1.8 |
| pH7.0 | 1.8 | 1.8 | 1.8 | 1.8 | 1.8 |
| pH7.4 | 1.8 | 1.8 | 1.7 | 1.8 | 1.8 |

TABLE 49

| (Residual rate (%) of Comparative Example 5) | | | | | |
|---|---|---|---|---|---|
| Time (hr) | 0 | 0.5 | 1 | 2 | 3 |
| pH5.0 | 93.9 | 93.5 | 93.4 | 93.9 | 93.9 |
| pH5.5 | 93.9 | 93.8 | 93.8 | 94.0 | 93.6 |
| pH6.0 | 93.5 | 94.0 | 93.5 | 93.9 | 94.0 |
| pH6.5 | 93.5 | 93.9 | 93.6 | 93.5 | 93.5 |
| pH7.0 | 93.9 | 93.4 | 93.8 | 93.9 | 93.3 |
| pH7.4 | 93.3 | 93.9 | 93.9 | 93.4 | 93.4 |

TABLE 50

| (Production rate (%) of Alvocidib from Comparative Example 5) | | | | | |
|---|---|---|---|---|---|
| Time (hr) | 0 | 0.5 | 1 | 2 | 3 |
| pH5.0 | 0.0 | 0.0 | 0.0 | 0.0 | 0.0 |
| pH5.5 | 0.0 | 0.0 | 0.0 | 0.0 | 0.0 |
| pH6.0 | 0.0 | 0.0 | 0.0 | 0.0 | 0.0 |
| pH6.5 | 0.0 | 0.0 | 0.0 | 0.0 | 0.0 |
| pH7.0 | 0.0 | 0.0 | 0.0 | 0.0 | 0.0 |
| pH7.4 | 0.0 | 0.0 | 0.0 | 0.0 | 0.0 |

TABLE 51

| (Residual rate (%) of Comparative Example 6) | | | | | |
|---|---|---|---|---|---|
| Time (hr) | 0 | 0.5 | 1 | 2 | 3 |
| pH5.0 | — | — | — | — | — |
| pH5.5 | — | — | — | — | — |
| pH6.0 | — | — | — | — | — |
| pH6.5 | — | — | — | — | — |
| pH7.0 | — | — | — | — | — |
| pH7.4 | 93.7 | 93.6 | 95.1 | 94.9 | — |

TABLE 52

| (Production rate (%) of Alvocidib from Comparative Example 6) | | | | | |
|---|---|---|---|---|---|
| Time (hr) | O | 0.5 | 1 | 2 | 3 |
| pH5.0 | — | — | — | — | — |
| pH5.5 | — | — | — | — | — |
| pH6.0 | — | — | — | — | — |
| pH6.5 | — | — | — | — | — |
| pH7.0 | — | — | — | — | — |
| pH7.4 | 4.3 | 4.4 | 4.5 | 4.7 | — |

TABLE 53

| (Residual rate (%) of Comparative Example 7) | | | | | |
|---|---|---|---|---|---|
| Time (hr) | 0 | 0.5 | 1 | 2 | 3 |
| pH5.0 | 96.8 | 93.9 | 90.1 | 83.8 | 77.6 |
| pH5.5 | 97.0 | 91.9 | 85.4 | 75.9 | 66.6 |
| pH6.0 | 96.4 | 73.9 | 51.7 | 28.9 | 15.2 |
| pH6.5 | 96.0 | 65.3 | 38.8 | 16.8 | 6.6 |
| pH7.0 | 95.9 | 62.6 | 35.5 | 14.2 | 5.1 |
| pH7.4 | 95.3 | 63.0 | 36.3 | 15.3 | 5.6 |

TABLE 54

| (Production rate (%) of Alvocidib from Comparative Example 7) | | | | | |
|---|---|---|---|---|---|
| Time (hr) | 0 | 0.5 | 1 | 2 | 3 |
| pH5.0 | 2.8 | 5.7 | 9.7 | 15.7 | 21.9 |
| pH5.5 | 2.7 | 7.9 | 14.3 | 23.8 | 33.1 |
| pH6.0 | 3.4 | 26.1 | 48.3 | 70.9 | 84.8 |
| pH6.5 | 3.9 | 34.7 | 61.2 | 83.2 | 93.4 |
| pH7.0 | 4.1 | 37.3 | 64.3 | 85.8 | 94.9 |
| pH7.4 | 4.2 | 36.7 | 63.5 | 84.7 | 94.4 |

TABLE 55

| (Residual rate (%) of Comparative Example 8) | | | | | |
|---|---|---|---|---|---|
| Time (hr) | 0 | 0.5 | 1 | 2 | 3 |
| pH5.0 | 83.4 | 81.9 | 80.4 | 78.1 | 73.9 |
| pH5.5 | 83.4 | 80.7 | 78.3 | 73.5 | 67.6 |
| pH6.0 | 83.5 | 72.6 | 63.5 | 36.7 | 34.5 |
| pH6.5 | 83.3 | 66.7 | 53.9 | 45.2 | 20.4 |
| pH7.0 | 83.1 | 64.4 | 50.5 | 32.1 | 16.4 |
| pH7.4 | 83.1 | 65.6 | 52.4 | 32.7 | 18.5 |

TABLE 56

| (Production rate (%) of Alvocidib from Comparative Example 8) | | | | | |
|---|---|---|---|---|---|
| Time (hr) | 0 | 0.5 | 1 | 2 | 3 |
| pH5.0 | 16.1 | 17.7 | 19.2 | 21.6 | 25.7 |
| pH5.5 | 16.1 | 18.8 | 21.4 | 26.2 | 32.0 |
| pH6.0 | 16.3 | 27.2 | 36.3 | 62.9 | 65.4 |
| pH6.5 | 16.5 | 33.1 | 45.9 | 54.4 | 79.4 |
| pH7.0 | 16.6 | 35.4 | 49.3 | 67.6 | 83.5 |
| pH7.4 | 16.7 | 34.2 | 47.4 | 67.0 | 81.4 |

TABLE 57

| (Residual rate (%) of Comparative Example 9) | | | | | |
|---|---|---|---|---|---|
| Time (hr) | 0 | 0.5 | 1 | 2 | 3 |
| pH5.0 | 85.7 | 84.0 | 82.6 | 79.4 | 77.0 |
| pH5.5 | 86.0 | 83.3 | 81.1 | 78.4 | 74.2 |
| pH6.0 | 86.0 | 76.5 | 69.2 | 53.9 | 44.3 |
| pH6.5 | 86.0 | 74.7 | 66.2 | 49.4 | 39.1 |
| pH7.0 | 85.9 | 75.8 | 68.1 | 52.8 | 42.9 |
| pH7.4 | 85.3 | 76.2 | 70.3 | 56.0 | 46.7 |

TABLE 58

| (Production rate (%) of Alvocidib from Comparative Example 9) | | | | | |
|---|---|---|---|---|---|
| Time (hr) | 0 | 0.5 | 1 | 2 | 3 |
| pH5.0 | 5.0 | 7.1 | 8.7 | 12.8 | 15.6 |
| pH5.5 | 4.9 | 8.5 | 11.3 | 17.7 | 22.4 |
| pH6.0 | 5.0 | 17.1 | 26.0 | 43.4 | 54.0 |
| pH6.5 | 5.1 | 20.9 | 31.1 | 49.6 | 60.2 |
| pH7.0 | 5.3 | 21.7 | 30.7 | 47.2 | 57.1 |
| pH7.4 | 5.6 | 22.1 | 29.7 | 44.0 | 53.3 |

TABLE 59

| (Residual rate (%) of Comparative Example 10) | | | | | |
|---|---|---|---|---|---|
| Time (hr) | 0 | 0.5 | 1 | 2 | 3 |
| pH5.0 | 93.4 | 93.2 | 92.7 | 91.4 | 91.2 |
| pH5.5 | 93.2 | 92.7 | 91.7 | 89.9 | 88.7 |
| pH6.0 | 93.1 | 90.7 | 88.6 | 83.1 | 79.7 |
| pH6.5 | 93.2 | 90.9 | 87.4 | 81.1 | 76.6 |
| pH7.0 | 93.2 | 92.3 | 88.2 | 81.5 | 75.7 |
| pH7.4 | 93.2 | 92.2 | 89.3 | 82.9 | 78.4 |

TABLE 60

| (Production rate (%) of Alvocidib from Comparative Example 10) | | | | | |
|---|---|---|---|---|---|
| Time (hr) | 0 | 0.5 | 1 | 2 | 3 |
| pH5.0 | 2.0 | 2.3 | 2.7 | 3.7 | 4.2 |
| pH5.5 | 2.0 | 2.7 | 3.7 | 5.5 | 6.8 |
| pH6.0 | 2.1 | 4.4 | 7.2 | 12.8 | 16.3 |
| pH6.5 | 2.3 | 5.1 | 8.8 | 15.6 | 20.2 |
| pH7.0 | 2.1 | 5.2 | 8.5 | 15.5 | 19.5 |
| pH7.4 | 2.1 | 4.6 | 7.5 | 13.3 | 17.1 |

TABLE 61

| (Residual rate (%) of Comparative Example 11) | | | | | |
|---|---|---|---|---|---|
| Time (hr) | 0 | 0.5 | 1 | 2 | 3 |
| pH5.0 | — | — | — | — | — |
| pH5.5 | — | — | — | — | — |
| pH6.0 | — | — | — | — | — |
| pH6.5 | — | — | — | — | — |
| pH7.0 | — | — | — | — | — |
| pH7.4 | 92.9 | 92.3 | 91.8 | 91.3 | — |

TABLE 62

| (Production rate (%) of Alvocidib from Comparative Example 11) | | | | | |
|---|---|---|---|---|---|
| Time (hr) | 0 | 0.5 | 1 | 2 | 3 |
| pH5.0 | — | — | — | — | — |
| pH5.5 | — | — | — | — | — |
| pH6.0 | — | — | — | — | — |
| pH6.5 | — | — | — | — | — |
| pH7.0 | — | — | — | — | — |
| pH7.4 | 1.0 | 1.2 | 1.3 | 1.5 | — |

TABLE 63

| (Residual rate (%) of Comparative Example 12) | | | | | |
|---|---|---|---|---|---|
| Time (hr) | 0 | 0.5 | 1 | 2 | 3 |
| pH5.0 | — | — | — | — | — |
| pH5.5 | — | — | — | — | — |
| pH6.0 | — | — | — | — | — |
| pH6.5 | — | — | — | — | — |
| pH7.0 | — | — | — | — | — |
| pH7.4 | 98.0 | 97.5 | 97.6 | 97.6 | — |

TABLE 64

| (Production rate (%) of Alvocidib from Comparative Example 12) | | | | | |
|---|---|---|---|---|---|
| Time (hr) | 0 | 0.5 | 1 | 2 | 3 |
| pH5.0 | — | — | — | — | — |
| pH5.5 | — | — | — | — | — |
| pH6.0 | — | — | — | — | — |
| pH6.5 | — | — | — | — | — |
| pH7.0 | — | — | — | — | — |
| pH7.4 | 1.4 | 1.5 | 1.6 | 1.8 | — |

TABLE 65

| (Residual rate (%) of Comparative Example 13) | | | | | |
|---|---|---|---|---|---|
| Time (hr) | 0 | 0.5 | 1 | 2 | 3 |
| pH5.0 | 99.8 | 96.0 | 94.0 | 90.8 | 86.5 |
| pH5.5 | 98.3 | 91.3 | 85.5 | 73.9 | 64.7 |
| pH6.0 | 98.7 | 72.9 | 56.3 | 30.4 | 16.8 |
| pH6.5 | 99.5 | 42.2 | 20.0 | 3.8 | 0.9 |
| pH7.0 | 97.8 | 9.3 | 1.3 | 0.0 | 0.0 |
| PH7.4 | 97.2 | 0.8 | 0.0 | 0.0 | 0.0 |

TABLE 66

| (Production rate (%) of Alvocidib from Comparative Example 13) | | | | | |
|---|---|---|---|---|---|
| Time (hr) | 0 | 0.5 | 1 | 2 | 3 |
| pH5.0 | 0.0 | 2.2 | 4.1 | 8.3 | 12.3 |
| pH5.5 | 0.0 | 6.5 | 11.9 | 22.6 | 32.2 |
| pH6.0 | 0.0 | 23.8 | 40.3 | 63.0 | 75.5 |
| pH6.5 | 0.2 | 51.7 | 73.5 | 87.1 | 90.0 |
| pH7.0 | 0.5 | 82.2 | 89.7 | 91.0 | 91.0 |
| PH7.4 | 1.3 | 90.5 | 91.2 | 91.4 | 92.1 |

TABLE 67

| (Residual rate (%) of Comparative Example 14) | | | | | |
|---|---|---|---|---|---|
| Time (hr) | 0 | 0.5 | 1 | 2 | 3 |
| pH5.0 | 97.3 | 80.3 | 66.8 | 45.6 | 30.7 |
| pH5.5 | 97.2 | 53.8 | 30.3 | 8.7 | 2.9 |
| pH6.0 | 96.7 | 9.0 | 1.2 | 0.0 | 0.0 |
| pH6.5 | 95.4 | 0.0 | 0.0 | 0.0 | 0.0 |
| pH7.0 | 91.7 | 0.0 | 0.0 | 0.0 | 0.0 |
| pH7.4 | 84.4 | 0.0 | 0.0 | 0.0 | 0.0 |

TABLE 68

| (Production rate (%) of Alvocidib from Comparative Example 14) | | | | | |
|---|---|---|---|---|---|
| Time (hr) | 0 | 0.5 | 1 | 2 | 3 |
| pH5.0 | 1.2 | 17.9 | 31.1 | 53.7 | 68.5 |
| pH5.5 | 1.4 | 44.2 | 67.2 | 88.5 | 93.9 |
| pH6.0 | 1.9 | 88.1 | 95.7 | 97.0 | 97.1 |
| pH6.5 | 3.2 | 97.0 | 96.7 | 98.2 | 97.6 |
| pH7.0 | 6.9 | 96.8 | 96.8 | 96.7 | 96.7 |
| pH7.4 | 14.2 | 97.3 | 97.2 | 97.2 | 97.2 |

Experimental Example 2. Stability Evaluation of Solution Formulation

For Example 1, Example 2, Example 5, Example 6, Comparative Example 13 and Comparative Example 14, the attrition rate of the test compound and the conversion rate of the test compound to Alvocidib in a solution formulation were calculated by the following method.

Example 1, Example 2, Example 5, Example 6, Comparative Example 13 and Comparative Example 14 were each added to buffer solutions adjusted to pH 3.0, 4.0 and 5.0, respectively, at a concentration of 0.1 mg/mL, and left at 5° C. After 0, 1, 2 and 4 weeks, the residual rates of the compounds of Example 1, Example 2, Example 3, Example 4, Comparative Example 13 and Comparative Example 14 and the production rate of Alvocidib were determined by HPLC.

The buffer solutions used at each pH are as follows.

pH 3.0: 5 mM tartrate buffer solution/10% sucrose solution (pH 3.0)

pH 4.0: 5 mM tartrate buffer solution/10% sucrose solution (pH 4.0)

pH 5.0: 5 mM tartrate buffer solution/10% sucrose solution (pH 5.0)

The measurement conditions for HPLC are as follows.

<HPLC Conditions> column: Acquity UPLC BEH C18, 1.7 um, 50×2.1 mm column temperature: 40° C.

mobile phase:

A: water containing 0.1% trifluoroacetic acid

B: acetonitrile

A/B (min):

80/20(0)→75/25(3)→0/100(3.5)→0/100(4)→80/20 (4.01)→80/20(5)

flow rate: 0.8 mL/min detection: ultraviolet visible detector, measurement wavelength 254 nm injection: 3 μL The test results of Experimental Example 2 are shown in Table 69 to Table 80. The compounds of Example 1, Example 2, Example 5 and Example 6 were stable at pH 3 and pH 4, and the conversion to Alvocidib hardly progressed even after 4 weeks. Although the compounds were gradually converted to Alvocidib at pH 5, the production rate of Alvocidib was 5% or less.

On the other hand, the compound of Comparative Example 13 was stable at pH 3, but was gradually converted to Alvocidib at pH 4, and about 40% was converted to Alvocidib at pH5 after 4 weeks. It was confirmed that the compound of Comparative Example 14 was gradually converted to Alvocidib at pH 3, and almost completely converted to Alvocidib after 4 weeks at pH 5.

From the above, it is shown that the compound of the present disclosure has the characteristics of being stable under storage conditions of 5° C. and pH 3 to pH 5, and therefore, it has an exceptional effect as a solution formulation, that is, it can be stably stored.

TABLE 69

(Residual rate (%) of Example 1)

| Time (week) | 0 | 1 | 2 | 4 |
|---|---|---|---|---|
| pH3.0 | 99.2 | 99.2 | 99.0 | 99.0 |
| pH4.0 | 99.5 | 99.3 | 99.1 | 99.1 |
| pH5.0 | 99.4 | 98.5 | 97.6 | 96.5 |

TABLE 70

(Production rate (%) of Alvocidib from Example 1)

| Time (week) | 0 | 1 | 2 | 4 |
|---|---|---|---|---|
| pH3.0 | 0.0 | 0.0 | 0.1 | 0.1 |
| pH4.0 | 0.0 | 0.1 | 0.2 | 0.4 |
| pH5.0 | 0.1 | 1.2 | 1.9 | 3.2 |

TABLE 71

(Residual rate (%) of Example 2)

| Time (week) | 0 | 1 | 2 | 4 |
|---|---|---|---|---|
| pH3.0 | 96.5 | 96.5 | 96.4 | 96.5 |
| pH4.0 | 96.4 | 96.5 | 96.4 | 96.4 |
| pH5.0 | 96.4 | 95.5 | 94.5 | 93.0 |

TABLE 72

(Production rate (%) of Alvocidib from Example 2)

| Time (week) | 0 | 1 | 2 | 4 |
|---|---|---|---|---|
| pH3.0 | 0.0 | 0.0 | 0.0 | 0.1 |
| pH4.0 | 0.0 | 0.1 | 0.2 | 0.3 |
| pH5.0 | 0.1 | 1.1 | 1.9 | 3.1 |

TABLE 73

(Residual rate (%) of Example 5)

| Time (week) | 0 | 1 | 2 | 4 |
|---|---|---|---|---|
| pH3.0 | 98.2 | 98.2 | 98.1 | 98.1 |
| pH4.0 | 98.2 | 98.2 | 98.1 | 98.1 |
| pH5.0 | 98.1 | 97.2 | 96.6 | 95.0 |

TABLE 74

(Production rate (%) of Alvocidib from Example 5)

| Time (week) | 0 | 1 | 2 | 4 |
|---|---|---|---|---|
| pH3.0 | 0.2 | 0.2 | 0.3 | 0.3 |
| pH4.0 | 0.2 | 0.3 | 0.4 | 0.5 |
| pH5.0 | 0.4 | 1.2 | 2.1 | 3.7 |

TABLE 75

(Residual rate (%) of Example 6)

| Time (week) | 0 | 1 | 2 | 4 |
|---|---|---|---|---|
| pH3.0 | 98.8 | 98.8 | 98.8 | 98.8 |
| pH4.0 | 98.8 | 98.7 | 98.5 | 98.2 |
| pH5.0 | 98.7 | 97.0 | 95.3 | 91.8 |

TABLE 76

| (Production rate (%) of Alvocidib from Example 6) | | | | |
|---|---|---|---|---|
| Time (week) | 0 | 1 | 2 | 4 |
| pH3.0 | 0.5 | 0.5 | 0.6 | 0.6 |
| pH4.0 | 0.5 | 0.7 | 0.8 | 0.9 |
| pH5.0 | 0.7 | 1.6 | 2.6 | 4.6 |

TABLE 77

| (Residual rate (%) of Comparative Example 13) | | | | |
|---|---|---|---|---|
| Time (week) | 0 | 1 | 2 | 4 |
| pH3.0 | 99.6 | 99.3 | 99.5 | 99.1 |
| pH4.0 | 99.4 | 98.1 | 97.4 | 94.4 |
| pH5.0 | 98.1 | 84.3 | 71.7 | 55.9 |

TABLE 78

| (Production rate (%) of Alvocidib from Comparative Example 13) | | | | |
|---|---|---|---|---|
| Time (week) | 0 | 1 | 2 | 4 |
| pH3.0 | 0.1 | 0.2 | 0.3 | 0.6 |
| pH4.0 | 0.2 | 1.2 | 2.2 | 4.8 |
| pH5.0 | 1.4 | 13.7 | 25.3 | 39.4 |

TABLE 79

| (Residual rate (%) of Comparative Example 14) | | | | |
|---|---|---|---|---|
| Time (week) | 0 | 1 | 2 | 4 |
| pH3.0 | 98.5 | 97.1 | 95.8 | 93.6 |
| pH4.0 | 97.5 | 86.7 | 78.3 | 63.0 |
| pH5.0 | 86.4 | 25.7 | 8.1 | 1.1 |

TABLE 80

| (Production rate (%) of Alvocidib from Comparative Example 14) | | | | |
|---|---|---|---|---|
| Time (week) | 0 | 1 | 2 | 4 |
| pH3.0 | 1.3 | 2.7 | 3.9 | 6.1 |
| pH4.0 | 2.2 | 12.8 | 21.1 | 36.2 |
| pH5.0 | 13.2 | 72.5 | 90.1 | 97.1 |

Experimental Example 3. Evaluation of Conversion Rate to Active Form in Human Plasma and BALB/c Mouse Plasma For Example 1, Example 2, Example 3, Example 4, Example 5, Example 6, Comparative Example 3, Comparative Example 4, Comparative Example 6, Comparative Example 7, Comparative Example 8, Comparative Example 9, Comparative Example 10 and Comparative Example 12, the attrition rate of the test compound and the conversion rate of the test compound to Alvocidib in human plasma and BALB/c mouse plasma were calculated by the following method.

The test compound was added to human plasma or BALB/c mouse plasma at a concentration of 0.2 μmol/L, and incubated at 37° C. The peak areas of the test compound and Alvocidib in the sample were determined by LC-MS/MS after 0, 30 and 60 minutes for Example 1, Example 2, Example 3, Example 4, Example 5 and Example 6, and after 0, 60 and 120 minutes for Comparative Example 3, Comparative Example 4, Comparative Example 6, Comparative Example 7, Comparative Example 8, Comparative Example 9, Comparative Example 10 and Comparative Example 12, and the attrition rate of the test compound and the conversion rate of the test compound to Alvocidib were calculated by the following formula.

Attrition rate of test compound (%):(peak area of test compound in sample/peak area of test compound in sample after 0 minute)×100

Conversion rate to Alvocidib (%):(peak area of Alvocidib in sample/peak area of Alvocidib in reaction solution containing 0.2 μmol/L Alvocidib)×100

The measurement conditions for LC-MS/MS are as follows.

HPLC: Prominence system (Shimadzu Corporation)

MS/MS:

Example 1, Example 2, Example 3, Example 4, Example 5, Example 6, Comparative Example 8 (mouse), Comparative Example 10 (mouse) and Comparative Example 12 (mouse)

QTRAP5500 (SCIEX)

Comparative Example 6, Comparative Example 7, Comparative Example 8 (human), Comparative Example 9, Comparative Example 10 (human) and Comparative Example 12 (human)

4000 QTRAP (SCIEX)

column:

other than Example 3 and Example 4

Cadenza CD-C18, 3 μm, 50×2 mm (Imtakt Corporation)

Example 3 and Example 4

Kinetex C8, 2.6 μm, 50×2.1 mm (Phenomenex)

column temperature: 40° C.

mobile phase:

A: water containing 0.1% formic acid

B: acetonitrile containing 0.1% formic acid

A/B (min):

Example 1, Example 2, Example 5, Example 6, Comparative Example 8 (mouse), Comparative Example 10 (mouse) and Comparative Example 12 (mouse)

90/10(0)→40/60(5.0)→10/90(5.1)→10/90(6.5)→90/10(6.6)→90/10(8.0)

Example 3 and Example 4

86/14(0)→86/14(3.5)→10/90(5.5)→10/90(6.5)→86/14(6.6)→86/14(9.5)

Comparative Example 6, Comparative Example 7, Comparative Example 8 (human), Comparative Example 9, Comparative Example 10 (human) and Comparative Example 12 (human)

90/10(0)→10/90(2.5)→10/90(3.5)→90/10(3.6)→90/10(5.0)

flow rate: 0.4 mL/min detection: ESI (positive mode)

injection: 1 to 5 μL

The test results of Experimental Example 3 are shown in Table 81. It was confirmed that the conversion of the compounds of Example 1, Example 2, Example 3, Example 4, Example 5 and Example 6 to Alvocidib proceeded rapidly under both human plasma and BALB/c mouse plasma conditions, with small differences between species.

On the other hand, that the compounds of Comparative Example 3, Comparative Example 4, Comparative Example 6, Comparative Example 7, Comparative Example 8, Comparative Example 9, Comparative Example 10 and Comparative Example 12 were hardly converted to Alvocidib in human plasma even after 120 minutes, and remained unchanged. It was confirmed that the compounds of Comparative Example 6 and Comparative Example 7 were efficiently converted to Alvocidib in BALB/c mouse plasma, but showed a low conversion rate in human plasma, with large differences between species.

From the above, it is shown that the compound of the present disclosure has exceptional effects as a prodrug, that is, it is rapidly degraded and converted to Alvocidib in human and BALB/c mouse plasma without difference between species.

TABLE 81

| | | Human plasma | | Mouse plasma | |
|---|---|---|---|---|---|
| Compound Name | Time (min) | Residual rate (%) of test compound | Production rate (%) of Alvocidib | Residual rate (%) of test compound | Production rate (%) of Alvocidib |
| Example 1 | 0 | 100 | 0 | 100 | 0 |
| | 30 | 6 | 83 | 24 | 58 |
| | 60 | 0 | 85 | 3 | 79 |
| Example 2 | 0 | 100 | 1 | 100 | 0 |
| | 30 | 4 | 85 | 25 | 74 |
| | 60 | 2 | 87 | 4 | 87 |
| Example 3 | 0 | 100 | 0 | 100 | 0 |
| | 30 | 3 | 105 | 8 | 90 |
| | 60 | 0 | 104 | 0 | 108 |
| Example 4 | 0 | 100 | 1 | 100 | 0 |
| | 30 | 4 | 78 | 5 | 75 |
| | 60 | 4 | 83 | 3 | 86 |
| Example 5 | 0 | 100 | 2 | 100 | 2 |
| | 30 | 1 | 90 | 36 | 61 |
| | 60 | 0 | 92 | 8 | 90 |
| Example 6 | 0 | 100 | 1 | 100 | 0 |
| | 30 | 3 | 88 | 26 | 70 |
| | 60 | 2 | 92 | 2 | 89 |
| Comparative Example 3 | 0 | 100 | 1 | 100 | 1 |
| | 60 | 78 | 1 | 90 | 7 |
| | 120 | 101 | 2 | 78 | 13 |
| Comparative Example 4 | 0 | 100 | 2 | 100 | 2 |
| | 60 | 101 | 3 | 94 | 3 |
| | 120 | 134 | 3 | 92 | 3 |
| Comparative Example 6 | 0 | 100 | 5 | 100 | 6 |
| | 60 | 89 | 12 | 48 | 48 |
| | 120 | 89 | 15 | 33 | 66 |
| Comparative Example 7 | 0 | 100 | 6 | 100 | 1 |
| | 60 | 77 | 26 | 25 | 64 |
| | 120 | 65 | 32 | 10 | 79 |
| Comparative Example 8 | 0 | 100 | 4 | 100 | 19 |
| | 60 | 87 | 12 | 14 | 94 |
| | 120 | 94 | 16 | 4 | 107 |
| Comparative Example 9 | 0 | 100 | 3 | 100 | 3 |
| | 60 | 85 | 18 | 70 | 33 |
| | 120 | 80 | 25 | 54 | 43 |
| Comparative Example 10 | 0 | 100 | 0 | 100 | 1 |
| | 60 | 104 | 2 | 84 | 5 |
| | 120 | 105 | 3 | 89 | 6 |
| Comparative Example 12 | 0 | 100 | 0 | 100 | 2 |
| | 60 | 74 | 23 | 85 | 19 |
| | 120 | 58 | 32 | 76 | 27 |

Experimental Example 4. Liposome Encapsulation Test

For Example 1, Example 2, Example 3, Example 4, Example 5, Example 6, Example 7, Example 8, Example 9, Example 10, Example 11, Example 12, Example 13, Example 14, Example 15, Example 16, Example 17 and Alvocidib, an encapsulation test in liposomes was performed using a remote loading method.

<Liposome Encapsulation Test of Example 1, Example 2, Example 5, Example 6, Example 9, Example 10, Example 11, Example 12, Example 13, Example 14, Example 15, and Example 16>

Hydrogenated soybean phosphatidylcholine (COATSOME NC-21E, manufactured by NOF CORPORATION, 7.77 g), cholesterol (manufactured by Sigma, 2.78 g) and distearoylphosphatidylethanolamine-methoxypolyethylene glycol 2000 (SUNBRIGHT DSPE-020CN, manufactured by NOF CORPORATION, 2.47 g) were dissolved in tert-butyl alcohol (720 mL) warmed to 65° C. The solution was placed in an eggplant flask and frozen in a dry ice-acetone bath, and then the tert-butyl alcohol was removed by evaporation under reduced pressure to give a lipid mixture.

To the above lipid mixture was added a 250 mM ammonium sulfate solution (240 mL), and the mixture was warmed to 65° C., and dispersed by a homogenizer (ULTRA-TURRAX, manufactured by IKA) to give a crude liposome dispersion. Then, the crude liposome dispersion was dispersed by a high pressure homogenizer (Nano-Mizer NM2, manufactured by YOSHIDA KIKAI CO., LTD.) at a pressure of 100 MPa to give liposomes with an average particle size (Z-average) of about 80 nm. The liposome outer solution was replaced with 10 mM L-histidine/10% sucrose solution (pH 6.5) using a dialysis cassette (Slide-A-Lyzer G2 Dialysis Cassettes 20K MWCO, manufactured by Thermo Scientific) to give an empty liposome solution. The solution was filtered through a 0.22 μm membrane filter, and a 10 mM L-histidine/10% sucrose solution (pH 6.5) was added thereto to adjust the total lipid concentration to 50 mM (50 μmol/mL). The lipid concentration was determined by quantitatively analyzing cholesterol using HPLC and calculating the total lipid concentration from the lipid mixing ratio. The amount for the above adjustment was increased or decreased as appropriate.

The compound (10 mg) was weighed, and the empty liposome solution (1 mL) with a total lipid concentration of 50 mM was added thereto. The solution was adjusted to pH 5 to 6 with 1 mol/L hydrochloric acid or 1 mol/L aqueous sodium hydroxide solution as necessary, warmed in a 65° C. water bath for 2 to 3 minutes, and ice-cooled. The mixture was centrifuged at 15,000×g for 5 minutes to precipitate and remove insoluble substances.

The liposome solution (100 μL) after removing insoluble substances was taken on an ultrafiltration filter (Amicon Ultra, 100K, 0.5 mL, manufactured by Merck) and centrifuged at 4° C., 15,000×g for 10 minutes. The compound concentrations in the liposome solution after removing insoluble substances and in the filtrate after ultrafiltration were determined by HPLC, and the encapsulation rate, encapsulation efficiency, and encapsulated compound content per 50 μmol of lipid were calculated by the following formula.

Encapsulation rate (%) = (compound concentration in liposome solution − compound concentration in filtrate) × 100/compound concentration in liposome solution Encapsulation efficiency (%) = (compound concentration in liposome solution − compound concentration in filtrate) × 100/compound concentration upon introduction -continued Encapsulated compound content (mg) per 50 μmol of lipid = compound concentration in liposome solution × encapsulation rate (%)/100

The measurement conditions for HPLC are as follows.

HPLC Conditions column: Acquity UPLC BEH C18, 1.7 um, 50×2.1 mm column temperature: 40° C.

mobile phase:

A: water containing 0.1% trifluoroacetic acid

B: acetonitrile

A/B (min): 95/5(0)→0/100(3.5)→0/100(4)→95/5(4.01)→95/5(5), or

A/B (min): 80/20(0)→70/30(3)→0/100(3.5)→0/100(4)→80/20(4.01)→80/20(5), or

A/B (min): 80/20(0)→75/25(3)→0/100(3.5)→0/100(4)→80/20(4.01)→80/20(5), or

A/B (min): 95/5(0)→70/30(7)→0/100(8)→0/100(8.5)→95/5(8.51)→95/5(10)

flow rate: 0.8 mL/min detection: ultraviolet visible detector, measurement wavelength 254 nm injection: 2 to 5 μL <Liposome Encapsulation Test of Example 3 and Example 4>

An empty liposome solution with a total lipid concentration of 75 mM was prepared by the same procedure as for the above example compound group. Each compound was weighed, and the empty liposome solution with a total lipid concentration of 75 mM was added thereto such that the compound concentration became 15 mg/mL. The solution was adjusted to pH 5 to 6 with 1 mol/L hydrochloric acid or 1 mol/L aqueous sodium hydroxide solution, warmed in a 65° C. water bath for 3 minutes, and ice-cooled. Hereafter, the encapsulation rate and encapsulation efficiency were calculated by the same procedure as for the above example compound group. The encapsulated compound content per 50 μmol of lipid was calculated by the following formula.

Encapsulated compound content (mg) per 50 μmol of lipid = compound concentration in liposome solution × encapsulation rate (%) × 50/75/100

<Liposome Encapsulation Test of Example 7, Example 8 and Example 17>

Hydrogenated soybean phosphatidylcholine (COATSOME NC-21E, manufactured by NOF CORPORATION, 1.727 g), cholesterol (manufactured by Sigma, 0.619 g) and distearoylphosphatidylethanolamine-methoxypolyethylene glycol 2000 (SUNBRIGHT DSPE-020CN, manufactured by NOF CORPORATION, 0.550 g) were dissolved in tert-butyl alcohol (130 mL) warmed to 60° C. The solution was placed in a glass bottle and frozen in a dry ice-acetone bath, and then the tert-butyl alcohol was removed by evaporation under reduced pressure to give a lipid mixture.

To the above lipid mixture was added a 250 mM ammonium sulfate solution (80 mL), and the mixture was warmed to 65° C., and dispersed by ultrasonic irradiation to give a crude liposome dispersion. Then, the crude liposome dispersion was dispersed by a high pressure homogenizer (Nano-Mizer NM2, manufactured by YOSHIDA KIKAI CO., LTD.) at a pressure of 100 MPa to give liposomes with an average particle size (Z-average) of about 80 nm. The liposome outer solution was replaced with 10 mM phosphate buffer solution/10% sucrose solution (pH 6.5) using a dialysis cassette (Slide-A-Lyzer G2 Dialysis Cassettes 20K MWCO, manufactured by Thermo Scientific) to give an empty liposome solution. The solution was filtered through a 0.22 μm membrane filter, and 10 mM phosphate buffer solution/10% sucrose solution (pH 6.5) was added thereto to adjust the total lipid concentration to 50 mM (50 μmol/mL). The amount for the above adjustment was increased or decreased as appropriate.

The lipid concentration was determined by adding 10% Triton X-100 to the liposome solution and heating the solution at 65° C. for 10 minutes to disrupt the liposomes, followed by quantitative analysis of the hydrogenated soybean phosphatidylcholine with a phospholipid assay kit (lab assay phospholipid, manufactured by FUJIFILM Wako Pure Chemical Corporation) and calculation of the total lipid concentration from the lipid mixture ratio.

The compound (10 mg) was weighed, and the above empty liposome solution (1 mL) with a total lipid concentration of 50 mM was added thereto. The solution was adjusted to pH 3 to 6 with 1 mol/L hydrochloric acid or 1 mol/L aqueous sodium hydroxide solution as necessary, warmed in a 65° C. water bath for 10 to 30 minutes, and ice-cooled. Hereafter, the encapsulation rate, encapsulation efficiency and encapsulated compound content per 50 μmol of lipid were calculated by the same procedure as for the above example compound group.

<Liposome Encapsulation Test of Alvocidib Hydrochloride>

An empty liposome solution with a total lipid concentration of 50 mM was prepared by the same procedure as for the compounds of Example 7, Example 8 and Example 17. Alvocidib hydrochloride (2.5 mg and 5 mg) was weighed, the empty liposome solution (0.5 mL) with a total lipid concentration of 50 mM was added thereto, and the solution was warmed in a 65° C. water bath for 60 minutes, and ice-cooled. Hereafter, the encapsulation rate, encapsulation efficiency and encapsulated compound content per 50 μmol of lipid were calculated by the same procedure as for the compound of Example 2.

The test results of Experimental Example 4 are shown in Table 82.

In particular, it was confirmed that each compound of Example 1, Example 2, Example 3, Example 4, Example 5, Example 6, Example 7, Example 8 and Example 9 could achieve high encapsulation rate, encapsulation efficiency and encapsulated compound content per 50 μmol of lipid. Alvocidib hydrochloride could not be encapsulated in liposomes at a concentration of 10 mg/mL due to gelation of the solution, but could be encapsulated in liposomes by lowering the concentration to 5 mg/mL.

From the above, the compound of the present disclosure has an exceptional effect, that is, it is efficiently encapsulated in liposomes.

TABLE 82

| Compound | Compound concentration when encapsulated (mg/mL) | Encap-sulation rate (%) | Encap-sulation efficiency (%) | Encapsulated compound content per 50 μmol of lipid (mg) |
|---|---|---|---|---|
| Example 1 | 10 | 82.9 | 73.2 | 7.3 |
| Example 2 | 10 | 81.1 | 71.1 | 7.1 |
| Example 3 | 15 | 61.0 | 60.2 | 6.0 |
| Example 4 | 15 | 72.2 | 71.2 | 7.1 |
| Example 5 | 10 | 75.7 | 71.6 | 7.2 |
| Example 6 | 10 | 73.8 | 65.9 | 6.6 |
| Example 7 | 10 | 81.1 | 72.8 | 7.3 |
| Example 8 | 10 | 60.6 | 61.1 | 6.1 |
| Example 9 | 10 | 78.5 | 72.1 | 7.2 |
| Example 10 | 10 | 22.8 | 23.0 | 2.3 |
| Example 11 | 10 | 45.5 | 46.1 | 4.6 |
| Example 12 | 10 | 35.8 | 36.2 | 3.6 |
| Example 13 | 10 | 35.2 | 34.6 | 3.5 |
| Example 14 | 10 | 26.6 | 28.4 | 2.8 |
| Example 15 | 10 | 23.6 | 22.2 | 2.2 |
| Example 16 | 10 | 20.7 | 21.7 | 2.2 |
| Example 17 | 10 | 26.5 | 23.8 | 2.4 |
| Alvocidib hydrochloride | 10 | not encapsulated due to gelation | | |
| Alvocidib hydrochloride | 5 | 99.5 | 96.2 | 4.8 |

Experimental Example 5. Stability Evaluation of Liposome Formulation Under Storage Conditions For Example 1, Example 2, Example 5, Example 6, Example 7, Example 8, Comparative Example 7 and Comparative Example 9, the storage stability of liposome formulation was evaluated by the following method.

For the liposome formulations of Example 1, Example 2, Example 5, Example 6, Example 7, Example 8, Comparative Example 7, and Comparative Example 9, the liposome outer solution was replaced with 10% sucrose solution or 10 mM tartrate buffer solution/10% sucrose solution (pH 4) using Sephadex G-25 column (PD-10, manufactured by GE Healthcare) or a dialysis cassette (Slide-A-Lyzer G2 Dialysis Cassettes 20K MWCO, manufactured by Thermo Scientific) to remove unencapsulated compound. The liposome formulation was filtered through a 0.22 μm membrane filter, and stored at 5° C. After 0 to 18 months, the Alvocidib content in the liposome formulations of Example 1, Example 2, Example 5, Example 6, Example 7, Example 8, Comparative Example 7 and Comparative Example 9 was determined by HPLC.

The HPLC measurement conditions are as follows.

<HPLC Conditions> column: Acquity UPLC BEH C18, 1.7 um, 50×2.1 mm column temperature: 40° C.

mobile phase:

A: water containing 0.1% trifluoroacetic acid

B: acetonitrile

A/B (min): 95/5(0)→0/100(3.5)→0/100(4)→95/5(4.01)→95/5(5), or

A/B (min): 80/20(0)→70/30(3)→0/100(3.5)→0/100(4)→80/20(4.01)→80/20(5), or

A/B (min): 80/20(0)→75/25(3)→0/100(3.5)→0/100(4)→80/20(4.01)→80/20(5)

flow rate: 0.8 mL/min detection: ultraviolet visible detector, measurement wavelength 254 nm injection: 3 to 5 μL The test results of Experimental Example 5 are shown in Table 83 and Table 84. It was confirmed that the liposome formulations of the compounds of Example 1, Example 2, Example 5, Example 6, Example 7 and Example 8 were stable for 3 months or more under 5° C. conditions. In particular, the Alvocidib content hardly increased after 15 months in Example 7 and after 18 months in Example 8.

On the other hand, it was confirmed that the liposomal formulations of the compounds of Comparative Example 7 and Comparative Example 9 showed a significant increase in the Alvocidib content at 6 to 7 months under 5° C. conditions.

From the above, it is shown that the compound of the present disclosure has an exceptional effect, that is, it is available as a liposome formulation with excellent storage stability.

TABLE 83

| (Alvocidib content % in liposome formulation) | | | | | | |
|---|---|---|---|---|---|---|
| Time (month) | Example 1 | Example 2 | Example 5 | Example 6 | Example 7 | Example 8 |
| 0 | 0.88 | 0.88 | 2.64 | 1.63 | 0.89 | 1.86 |
| 1 | 0.88 | 0.87 | 2.59 | 1.60 | — | 1.93 |
| 2 | 0.89 | 0.89 | 2.66 | 1.64 | — | — |
| 3 | 0.90 | 0.91 | 2.69 | 1.66 | — | — |
| 15 | — | — | — | — | 1.17 | — |
| 18 | — | — | — | — | — | 2.03 |

TABLE 84

| (Alvocidib content % in liposome formulation) | | |
|---|---|---|
| Time (month) | Comparative Example 7 | Comparative Example 9 |
| 0 | 0.56 | 1.17 |
| 6 | — | 27.2 |
| 7 | 23.2 | — |

Experimental Example 6. Pharmacokinetic Test

The solution formulations and liposome formulations of Example 1, Example 2, Example 3, Example 4, Example 5, Example 6, Example 11 and Comparative Example 6 were administered intravenously to mice, and the blood levels of the compound and Alvocidib were measured.

For the solution formulations of Example 1, Example 2, Example 3, Example 4, Example 5, Example 6, Example 11 and Comparative Example 6, the test compound was dissolved in a 10 mmol/L aqueous glycine solution (pH 2) containing 5% mannitol and filtered through a 0.22 μm membrane filter. This was used as a solution formulation.

For the liposome formulations of Example 1, Example 2, Example 3, Example 4, Example 5, Example 6, Example 11 and Comparative Example 6, liposomes containing the test compound were prepared in the same manner as in Experimental Example 4, the liposome outer solution was replaced with 10% sucrose solution, 10 mM phosphate buffer solution/10% sucrose solution (pH 6.5) or 10 mM tartrate buffer solution/10% sucrose solution (pH 4) using Sephadex G-25 column (PD-10, manufactured by GE Healthcare), followed by filtration through a 0.22 μm membrane filter to adjust the concentration. This was used as a liposome formulation.

For the liposome formulation of Example 1, in addition to the liposome formulation prepared by the above method, a liposome formulation prepared by the following method was also used (liposome formulation B).

Hydrogenated soybean phosphatidylcholine (COATSOME NC-21E, manufactured by NOF CORPORATION, 3.238 g), cholesterol (manufactured by Sigma, 1.160 g) and 1,2-disteroyl-rac-glycero-3-methylpolyoxyethylen 2000 (SUNBRIGHT GS-020, manufactured by NOF CORPORATION, 0.983 g) were dissolved in tert-butyl alcohol (300 mL) warmed to 65° C. The solution was placed in an eggplant flask and frozen in a dry ice-acetone bath, and then the tert-butyl alcohol was removed by evaporation under reduced pressure to give a lipid mixture.

To the above lipid mixture was added to a 250 mM ammonium sulfate solution (100 mL), and the mixture was warmed to 65° C., and dispersed by a homogenizer (ULTRA-TURRAX, manufactured by IKA) to give a crude liposome dispersion. Then, the crude liposome dispersion was dispersed by a high pressure homogenizer (Nano-Mizer NM2, manufactured by YOSHIDA KIKAI CO., LTD.) at a pressure of 100 MPa to give liposomes with an average particle size (Z-average) of about 80 nm. The liposome outer solution was replaced with 10 mM L-histidine/9.4% sucrose solution (pH 6.5) using a dialysis cassette (Slide-A-Lyzer G2 Dialysis Cassettes 20K MWCO, manufactured by Thermo Scientific) to give an empty liposome solution. The solution was filtered through a 0.22 μm membrane filter to adjust the total lipid concentration to 75 mM (75 μmol/mL). The compound (150 mg) of Example 1 was weighed, and the empty liposome solution with a total lipid concentration of 75 mM (10 mL) was added thereto. The solution was adjusted to pH 5 to 6 with 1 mol/L aqueous sodium hydroxide solution, warmed in a 65° C. water bath for 3 minutes, and ice-cooled. The liposome outer solution was replaced with 10 mM tartrate buffer solution/10% sucrose solution (pH 4) using a dialysis cassette (Slide-A-Lyzer G2 Dialysis Cassettes 20K MWCO, manufactured by Thermo Scientific), followed by filtration through a 0.22 μm membrane filter to adjust the concentration.

The solution formulation or liposome formulation was instantly administered intravenously to 7-week-old female BALB/c mice, and the blood was collected over time from the jugular vein without anesthesia up to 24 hours after administration for the solution formulation administration group and up to 72 hours after administration for the liposome formulation administration group. To the obtained blood was added 46% citric acid in a 1% volume, and centrifuged to give plasma. To the collected plasma was added acetonitrile containing 0.1 mol/L HCl in a 20-fold volume (in a 33-fold volume only for the solution formulations of Example 1 and Example 5) to give a plasma sample. The plasma sample was centrifuged, and the concentrations of the test compound and Alvocidib in the obtained supernatant were determined by LC-MS/MS.

The measurement conditions for LC-MS/MS are as follows.

HPLC: Prominence system (Shimadzu Corporation)

MS/MS:

Example 1, Example 2, Example 3, Example 4, Example 5 and Example 6

QTRAP5500 (SCIEX)

Example 11

4000 QTRAP (SCIEX)

column: Cadenza CD-C18, 3 μm, 50×2 mm (Imtakt Corporation)

column temperature: 40° C.

mobile phase:

A: water containing 0.1% formic acid

B: acetonitrile containing 0.1% formic acid

A/B (min):

Example 1, Example 2, Example 5 and Example 6

90/10(0)→40/60(5.0)→10/90(5.1)→10/90(6.5)→90/10(6.6)→90/10(8.0)

Example 3 and Example 4

90/10(0)→50/50(4.0)→10/90(4.2)→10/90(5.2)→90/10(5.3)→90/10(7.0)

Example 11 and Comparative Example 6

90/10(0)→10/90(2.5)→10/90(3.5)→90/10(3.6)→90/10(5.0)

flow rate: 0.4 mL/min detection: ESI (positive mode)

injection: 0.1 to 5 μL

The test results of Experimental Example 6 are shown in Tables 85 to 102. In the tables, "mean" means average and "S.D." means standard deviation. When the liposome formulation encapsulating Example 1, Example 2, Example 3, Example 4, Example 5, Example 6 or Example 11 was administered intravenously, it showed higher blood retention, compared with the corresponding solution formulation. On the other hand, when the liposome formulation encapsulating Comparative Example 6, it did not show improved blood retention, compared with the solution formulation of Comparative Example 6.

Considering these test results as well as the test results of Experimental Example 1 and Experimental Example 3, a series of the compounds of the present disclosure can be expected to produce an active form in humans as well as in mice, and thus are expected to expand the use of Alvocidib, which is limited in its use as a liposomal formulation, and are extremely useful.

TABLE 85

Solution formulation containing Example 1

| 1.0 mg/kg (Alvocidib conversion) i.v. administration | Example 1 compound concentration ($10^{-9}$ mol/L) | | Alvocidib compound concentration ($10^{-9}$ mol/L) | |
|---|---|---|---|---|
| Elapsed time | mean | S.D. | mean | S.D. |
| 0.083 hr | 839 | 235 | 108 | 25.3 |
| 0.25 hr | 384 | 56.3 | 157 | 34.9 |
| 0.50 hr | 147 | 35.6 | 161 | 7.64 |
| 1 hr | 77.6 | 26.9 | 126 | 13.8 |
| 2 hr | 19.4 | 1.78 | 54.3 | 13.3 |
| 6 hr | 11.9 | 2.38 | 48.4 | 4.56 |
| 24 hr | <6.02 | — | <8.54 | — |

TABLE 86

Liposome encapsulating Example 1

| 1.0 mg/kg (Alvocidib conversion) i.v. administration | Example 1 compound concentration ($10^{-9}$ mol/L) | | Alvocidib compound concentration ($10^{-9}$ mol/L) | |
|---|---|---|---|---|
| Elapsed time | mean | S.D. | mean | S.D. |
| 0.083 hr | 99600 | 3070 | 67.1 | 2.96 |
| 0.25 hr | 105100 | 8670 | 62.7 | 6.87 |
| 0.50 hr | 85100 | 2630 | 48.3 | 5 |
| 1 hr | 91600 | 14400 | 42.5 | 6.29 |
| 6 hr | 45900 | 3040 | 25.7 | 1.21 |
| 24 hr | 16700 | 3950 | 19.5 | 2.89 |

TABLE 86-continued

| Liposome encapsulating Example 1 | | | | |
|---|---|---|---|---|
| 1.0 mg/kg (Alvocidib conversion) i.v. administration | Example 1 compound concentration ($10^{-9}$ mol/L) | | Alvocidib compound concentration ($10^{-9}$ mol/L) | |
| Elapsed time | mean | S.D. | mean | S.D. |
| 48 hr | 4670 | 782 | <15.7 | — |
| 72 hr | 1130 | 231 | <15.7 | — |

TABLE 87

| Liposome encapsulating Example 1 (Liposome Formulation B) | | | | |
|---|---|---|---|---|
| 1.0 mg/kg (Alvocidib conversion) i.v. administration | Example 1 compound concentration ($10^{-9}$ mol/L) | | Alvocidib compound concentration ($10^{-9}$ mol/L) | |
| Elapsed time | mean | S.D. | mean | S.D. |
| 0.083 hr | 111500 | 20200 | 124 | 13.5 |
| 0.25 hr | 123600 | 13400 | 120 | 21.7 |
| 0.50 hr | 84200 | 12100 | 75.4 | 4.97 |
| 1 hr | 72100 | 59600 | 76.6 | 7.75 |
| 6 hr | 56100 | 15300 | 55.1 | 14.4 |
| 24 hr | 23000 | 1270 | 30.4 | 8.44 |
| 48 hr | 6170 | 1680 | <15.7 | — |
| 72 hr | 2570 | 864 | <15.7 | — |

TABLE 88

| Solution formulation containing Example 2 | | | | |
|---|---|---|---|---|
| 1.0 mg/kg (Alvocidib conversion) i.v. administration | Example 2 compound concentration ($10^{-9}$ mol/L) | | Alvocidib compound concentration ($10^{-9}$ mol/L) | |
| Elapsed time | mean | S.D. | mean | S.D. |
| 0.083 hr | 1490 | 25.2 | 4.78 | 0.902 |
| 0.25 hr | 510 | 51.2 | 6.25 | 1.45 |
| 0.50 hr | 147 | 16.1 | 5.73 | 0.376 |
| 1 hr | 94.4 | 3.43 | 4.67 | 1.13 |
| 2 hr | 46.7 | 25 | 2.59 | 0.287 |
| 6 hr | 17.9 | 2.63 | 2.05 | 0.339 |
| 24 hr | 5.29 | 0.556 | <1.57 | — |

TABLE 89

| Liposome encapsulating Example 2 | | | | |
|---|---|---|---|---|
| 1.0 mg/kg (Alvocidib conversion) i.v. administration | Example 2 compound concentration ($10^{-9}$ mol/L) | | Alvocidib compound concentration ($10^{-9}$ mol/L) | |
| Elapsed time | mean | S.D. | mean | S.D. |
| 0.083 hr | 110800 | 3880 | 62.7 | 3.42 |
| 0.25 hr | 101800 | 7120 | 49.9 | 4.12 |
| 0.50 hr | 80400 | 4160 | 39.5 | 8.37 |
| 1 hr | 95000 | 4050 | 41.2 | 4.67 |
| 6 hr | 45200 | 7480 | 24.9 | 3.1 |
| 24 hr | 16300 | 2020 | 17 | 0.651 |
| 48 hr | 2280 | 221 | <15.7 | — |
| 72 hr | 830 | 216 | <15.7 | — |

TABLE 90

| Solution formulation containing Example 3 | | | | |
|---|---|---|---|---|
| 1.0 mg/kg (Alvocidib conversion) i.v. administration | Example 3 compound concentration ($10^{-9}$ mol/L) | | Alvocidib compound concentration ($10^{-9}$ mol/L) | |
| Elapsed time | mean | S.D. | mean | S.D. |
| 0.083 hr | 649 | 180 | 93.3 | 20.9 |
| 0.25 hr | <113 | — | 96 | 6.44 |
| 0.50 hr | <113 | — | 96.1 | 13.8 |
| 1 hr | <113 | — | 82.8 | 6.45 |
| 2 hr | <113 | — | 51.1 | 11.1 |
| 6 hr | <113 | — | 37.3 | 7.18 |
| 24 hr | <113 | — | <15.7 | — |

TABLE 91

| Liposome encapsulating Example 3 | | | | |
|---|---|---|---|---|
| 1.0 mg/kg (Alvocidib conversion) i.v. administration | Example 3 compound concentration ($10^{-9}$ mol/L) | | Alvocidib compound concentration ($10^{-9}$ mol/L) | |
| Elapsed time | mean | S.D. | mean | S.D. |
| 0.083 hr | 66600 | 10100 | 48.3 | 8.6 |
| 0.25 hr | 76200 | 11200 | 43.8 | 15.3 |
| 0.50 hr | 63900 | 3500 | 33 | 4.26 |
| 1 hr | 73600 | 3740 | 35 | 6.24 |
| 6 hr | 28900 | 3940 | <15.7 | — |
| 24 hr | 13600 | 3650 | <15.7 | — |
| 48 hr | 3030 | 350 | <15.7 | — |
| 72 hr | 636 | 500 | <15.7 | — |

TABLE 92

| Solution formulation containing Example 4 | | | | |
|---|---|---|---|---|
| 1.0 mg/kg (Alvocidib conversion) i.v. administration | Example 4 compound concentration ($10^{-9}$ mol/L) | | Alvocidib compound concentration ($10^{-9}$ mol/L) | |
| Elapsed time | mean | S.D. | mean | S.D. |
| 0.083 hr | 661 | 284 | 59.2 | 14.8 |
| 0.25 hr | <113 | — | 83.2 | 9.76 |
| 0.50 hr | <113 | — | 67.8 | 4.14 |
| 1 hr | <113 | — | 79.5 | 5.75 |
| 2 hr | <113 | — | 43.9 | 7.52 |
| 6 hr | <113 | — | 29.1 | 8.75 |
| 24 hr | <113 | — | <15.7 | — |

TABLE 93

| Liposome encapsulating Example 4 | | | | |
|---|---|---|---|---|
| 1.0 mg/kg (Alvocidib conversion) i.v. administration | Example 4 compound concentration ($10^{-9}$ mol/L) | | Alvocidib compound concentration ($10^{-9}$ mol/L) | |
| Elapsed time | mean | S.D. | mean | S.D. |
| 0.083 hr | 68700 | 7090 | 29 | 6.92 |
| 0.25 hr | 83000 | 7210 | 32.7 | 7.86 |
| 0.50 hr | 69300 | 3030 | 32.9 | 1.89 |
| 1 hr | 62800 | 5090 | 20.1 | 4.47 |
| 6 hr | 29600 | 3460 | <15.7 | — |
| 24 hr | 11300 | 200 | <15.7 | — |

TABLE 93-continued

| Liposome encapsulating Example 4 | | | | |
|---|---|---|---|---|
| 1.0 mg/kg (Alvocidib conversion) i.v. administration | Example 4 compound concentration ($10^{-9}$ mol/L) | | Alvocidib compound concentration ($10^{-9}$ mol/L) | |
| Elapsed time | mean | S.D. | mean | S.D. |
| 48 hr | 2700 | 921 | <15.7 | — |
| 72 hr | 606 | 232 | <15.7 | — |

TABLE 94

| Solution formulation containing Example 5 | | | | |
|---|---|---|---|---|
| 1.0 mg/kg (Alvocidib conversion) i.v. administration | Example 5 compound concentration ($10^{-9}$ mol/L) | | Alvocidib compound concentration ($10^{-9}$ mol/L) | |
| Elapsed time | mean | S.D. | mean | S.D. |
| 0.083 hr | 1400 | 180 | 118 | 36.7 |
| 0.25 hr | 476 | 98.2 | 204 | 17.2 |
| 0.50 hr | 241 | 36 | 224 | 15.1 |
| 1 hr | 72.1 | 17.2 | 152 | 40.1 |
| 2 hr | 36.2 | 1.45 | 99.6 | 15.2 |
| 6 hr | 16.5 | 1.67 | 59.4 | 11.8 |
| 24 hr | <5.87 | — | <8.54 | — |

TABLE 95

| Liposome encapsulating Example 5 | | | | |
|---|---|---|---|---|
| 1.0 mg/kg (Alvocidib conversion) i.v. administration | Example 5 compound concentration ($10^{-9}$ mol/L) | | Alvocidib compound concentration ($10^{-9}$ mol/L) | |
| Elapsed time | mean | S.D. | mean | S.D. |
| 0.083 hr | 102000 | 18600 | 220 | 52 |
| 0.25 hr | 94800 | 36400 | 195 | 68.9 |
| 0.50 hr | 89100 | 14600 | 157 | 11.9 |
| 1 hr | 80600 | 4780 | 142 | 14.8 |
| 6 hr | 41400 | 7740 | 77 | 10.2 |
| 24 hr | 10300 | 1420 | 44.6 | 4.31 |
| 48 hr | 2740 | 1750 | <15.7 | — |
| 72 hr | <1080 | — | <15.7 | — |

TABLE 96

| Solution formulation containing Example 6 | | | | |
|---|---|---|---|---|
| 1.0 mg/kg (Alvocidib conversion) i.v. administration | Example 6 compound concentration ($10^{-9}$ mol/L) | | Alvocidib compound concentration ($10^{-9}$ mol/L) | |
| Elapsed time | mean | S.D. | mean | S.D. |
| 0.083 hr | 729 | 364 | 109 | 44.4 |
| 0.25 hr | 224 | 35.5 | 144 | 9.61 |
| 0.50 hr | 98.7 | 14.9 | 125 | 58.3 |
| 1 hr | 38.3 | 8.55 | 66.9 | 6.25 |
| 2 hr | 19.9 | 1.75 | 67 | 9.31 |
| 6 hr | 8.28 | 1.24 | 39.4 | 13.3 |
| 24 hr | <3.6 | — | <15.7 | — |

TABLE 97

| Liposome encapsulating Example 6 | | | | |
|---|---|---|---|---|
| 1.0 mg/kg (Alvocidib conversion) i.v. administration | Example 6 compound concentration ($10^{-9}$ mol/L) | | Alvocidib compound concentration ($10^{-9}$ mol/L) | |
| Elapsed time | mean | S.D. | mean | S.D. |
| 0.083 hr | 110100 | 11700 | 161 | 34.7 |
| 0.25 hr | 100200 | 8350 | 163 | 31.2 |
| 0.50 hr | 95800 | 14200 | 143 | 27.2 |
| 1 hr | 82300 | 8370 | 112 | 5.29 |
| 6 hr | 43600 | 3270 | 77 | 3.2 |
| 24 hr | 6450 | 1640 | 30.3 | 8.43 |
| 48 hr | 375 | 50.1 | <15.7 | — |
| 72 hr | <108 | — | <15.7 | — |

TABLE 98

| Solution formulation containing Example 11 | | | | |
|---|---|---|---|---|
| 1.0 mg/kg (Alvocidib conversion) i.v. administration | Example 11 compound concentration ($10^{-9}$ mol/L) | | Alvocidib compound concentration ($10^{-9}$ mol/L) | |
| Elapsed time | mean | S.D. | mean | S.D. |
| 0.083 hr | 497 | 99.3 | 175 | 50.3 |
| 0.25 hr | <107 | — | 278 | 33.7 |
| 0.50 hr | <107 | — | 214 | 18 |
| 1 hr | <107 | — | 142 | 15.7 |
| 2 hr | <107 | — | 104 | 14.8 |
| 6 hr | <107 | — | 45.5 | 3.72 |
| 24 hr | <107 | — | <15.7 | — |

TABLE 99

| Liposome encapsulating Example 11 | | | | |
|---|---|---|---|---|
| 1.0 mg/kg (Alvocidib conversion) i.v. administration | Example 11 compound concentration ($10^{-9}$ mol/L) | | Alvocidib compound concentration ($10^{-9}$ mol/L) | |
| Elapsed time | mean | S.D. | mean | S.D. |
| 0.083 hr | 65700 | 19900 | 124 | 36.5 |
| 0.25 hr | 92400 | 7430 | 146 | 20.6 |
| 0.50 hr | 36100 | 14600 | 83 | 32.5 |
| 1 hr | 69300 | 7190 | 58 | 21.8 |
| 6 hr | 28600 | 2570 | 26.4 | 4.33 |
| 24 hr | 11700 | 1580 | <15.7 | — |
| 48 hr | 2110 | 258 | <15.7 | — |
| 72 hr | 541 | 321 | <15.7 | — |

TABLE 100

| Solution formulation containing Comparative Example 6 | | | | |
|---|---|---|---|---|
| 1.0 mg/kg (Alvocidib conversion) i.v. administration | Comparative Example 6 compound concentration ($10^{-9}$ mol/L) | | Alvocidib compound concentration ($10^{-9}$ mol/L) | |
| Elapsed time | mean | S.D. | mean | S.D. |
| 0.083 hr | 2200 | 276 | 206 | 32 |
| 0.25 hr | 1100 | 261 | 255 | 44.7 |
| 0.50 hr | 493 | 44.5 | 236 | 28.8 |
| 1 hr | 178 | 52.6 | 144 | 17.2 |
| 2 hr | 17.4 | 3.63 | 86.1 | 14.2 |

TABLE 100-continued

| Solution formulation containing Comparative Example 6 | | | | |
|---|---|---|---|---|
| 1.0 mg/kg (Alvocidib conversion) i.v. administration | Comparative Example 6 compound concentration ($10^{-9}$ mol/L) | | Alvocidib compound concentration ($10^{-9}$ mol/L) | |
| Elapsed time | mean | S.D. | mean | S.D. |
| 6 hr | <4.59 | — | 43.8 | 16.2 |
| 24 hr | <4.59 | — | <15.7 | — |

TABLE 101

| Liposome encapsulating Comparative Example 6 | | | | |
|---|---|---|---|---|
| 1.0 mg/kg (Alvocidib conversion) i.v. administration | Comparative Example 6 compound concentration ($10^{-9}$ mol/L) | | Alvocidib compound concentration ($10^{-9}$ mol/L) | |
| Elapsed time | mean | S.D. | mean | S.D. |
| 0.083 hr | 2700 | 11.5 | 111 | 4.73 |
| 0.25 hr | 1160 | 245 | 168 | 3.06 |
| 0.50 hr | 688 | 193 | 159 | 27.3 |
| 1 hr | 105 | 64.9 | 79.6 | 13.6 |
| 6 hr | <4.59 | — | 45.3 | 14 |
| 24 hr | <4.59 | — | <15.7 | — |
| 48 hr | <4.59 | — | <15.7 | — |
| 72 hr | <4.59 | — | <15.7 | — |

TABLE 102

| Pharmacokinetic parameters | | |
|---|---|---|
| Compound | Half-life (hr) | AUC0-t (nmol · hr/L) |
| Solution formulation of Example 1 | 2.3 | 412 |
| Liposome encapsulating Example 1 | 12.4 | 1230000 |
| Solution formulation of Example 2 | 7.8 | 823 |
| Liposome encapsulating Example 2 | 10.2 | 1140000 |
| Solution formulation of Example 3 | NA | 54.1 |
| Liposome encapsulating Example 3 | 10.8 | 879000 |
| Solution formulation of Example 4 | NA | 55.1 |
| Liposome encapsulating Example 4 | 11.4 | 811000 |
| Solution formulation of Example 5 | 2.6 | 606 |
| Liposome encapsulating Example 5 | 10.8 | 924000 |
| Solution formulation of Example 6 | 2.5 | 305 |
| Liposome encapsulating Example 6 | 6.1 | 802000 |
| Solution formulation of Example 11 | NA | NA |
| Liposome encapsulating Example 11 | 11.3 | 792000 |
| Solution formulation of Comparative Example 6 | 0.3 | 896 |
| Liposome encapsulating Comparative Example 6 | 0.2 | 965 |

Experimental Example 7. Drug Efficacy Evaluation Test Using Tumor-Bearing Mice Transplanted with EMT6 Cells The liposome formulation encapsulating the compound of the present disclosure was treated and evaluated for anti-tumor effect.

The liposome formulations were prepared as follows. The liposomes encapsulating the compounds of Example 3 and Example 4 were prepared in the same manner as in Experimental Example 4, respectively. The liposome outer solution was replaced with 10 mM tartrate buffer solution/10% sucrose solution (pH 4) using Sephadex G-25 column (PD-10, manufactured by GE Healthcare), followed by concentration by an ultrafiltration filter (AmiconUltra, 100K, 15 mL, manufactured by Merck), and filtration through a 0.22 μm membrane filter.

EMT6 cells (ATCC) were intradermally transplanted into 5-week-old BALB/c mice (BALB/cAnNCrlCrlj, female, Charles River, Japan) around the ventral region at $5\times10^5$ cells/mouse. After confirming the engraftment of EMT6 cells 5 days after transplantation, they were divided into groups based on tumor diameter and body weight, and liposome formulations encapsulating Example 3 and Example 4 were administered through the tail vein at doses of 25 mg/kg and 50 mg/kg twice a week, respectively. The tumor volume was measured over time from the start of administration, and the tumor volume reduction effect due to compound administration was evaluated. The tumor volume was calculated by the following formula using the short and long diameters of the tumor measured with an electronic caliper (Mitutoyo). For comparison in this test, an empty liposome solution prepared in the same manner as in Experimental Example 1 was used.

$$\text{Tumor volume } [\text{mm}^3] = 0.5\times(\text{short diameter [mm]})^2\times\text{long diameter [mm]}$$

The anti-tumor effect was evaluated by comparing the control group administered with the empty liposome solution and the administration group of the compound of the present disclosure, and calculating T/C by the following formula.

$$T/C\,(\%) = (\text{Tumor volume at the end of administration in administration group of the compound of the present disclosure} - \text{Tumor volume at the start of administration in administration group of the compound of the present disclosure})/(\text{Tumor volume at the end of administration in control group} - \text{Tumor volume at the start of administration in control group})\times100$$

Table 103 shows the T/C (%) in tumor-bearing mice transplanted with EMT6 cells, at each dose and dosing period of the compound of the present disclosure. The liposome formulations encapsulating the compound of Example 3 and Example 4 significantly inhibited the increase in tumor volume.

TABLE 103

| | Dose (mg/kg) (Alvocidib conversion) | Dosing period (day) | Schedule (times/ week) | T/C (%) |
|---|---|---|---|---|
| Liposome encapsulating Example 3 | 25 | 10 | 2 | 26 |
| Liposome encapsulating Example 3 | 50 | 10 | 2 | 28 |
| Liposome encapsulating Example 4 | 25 | 10 | 2 | 28 |
| Liposome encapsulating Example 4 | 50 | 10 | 2 | 47 |

Experimental Example 8. Drug Efficacy Evaluation Test Using Tumor-Bearing Mice Transplanted with A673 Cells The liposome formulation encapsulating the compound of the present disclosure was treated and evaluated for anti-tumor effect and weight loss.

The liposome formulations were prepared as follows. The liposomes encapsulating the compounds of Example 1, Example 2, Example 5 and Example 6 were prepared in the same manner as in Experimental Example 4, respectively. The liposome outer solution was replaced with 10 mM tartrate buffer solution/10% sucrose solution (pH4.0) using a dialysis cassette (Slide-A-Lyzer G2 Dialysis Cassettes 20K MWCO, manufactured by Thermo Scientific), followed by filtration through a 0.22 μm membrane filter.

A673 cells (ATCC) were intradermally transplanted into 5-week-old BALB/c mice (CAnN.Cg-Foxnlnu/CrlCrlj, female, Charles River, Japan) around the ventral region at $3\times10^6$ cells/mouse. After confirming the engraftment of A673 cells 6 days after transplantation, they were divided into groups based on tumor diameter and body weight, and liposome formulations encapsulating Example 1, Example 2, Example 5 and Example 6 were administered through the tail vein at dose of 50 mg/kg twice a week, respectively. If weight loss of 10% or more was observed in the compound administration group compared to the start of administration, the administration was rest or performed at a dose of 37.5 mg/kg. The tumor volume was measured over time from the start of administration, and the tumor volume reduction effect due to compound administration was evaluated. The tumor volume was calculated by the following formula using the short and long diameters of the tumor measured with an electronic caliper (Mitutoyo). For comparison in this test, an empty liposome solution prepared in the same manner as in Experimental Example 1 was used.

$$\text{Tumor volume } [\text{mm}^3] = 0.5\times(\text{short diameter [mm]})^2\times\text{long diameter [mm]}$$

The anti-tumor effect was evaluated by comparing the control group administered with the empty liposome solution and the administration group of the compound of the present disclosure, and calculating T/C by the following formula.

$$T/C\,(\%) = (\text{Tumor volume at the end of administration in administration group of the compound of the present disclosure} - \text{Tumor volume at the start of administration in administration group of the compound of the present disclosure})/(\text{Tumor volume at the end of administration in control group} - \text{Tumor volume at the start of administration in control group})\times 100$$

Table 104 shows the T/C (%) and the presence or absence of weight loss of 10% or more compared to the start of administration in tumor-bearing mice transplanted with A673 cells, at each dosing period, dose and dosing schedule of the compound of the present disclosure. The liposome formulations encapsulating Example 1, Example 2, Example 5 and Example 6 inhibited the increase in tumor volume. Among them, the liposome formulations encapsulating Example 1 and Example 2 inhibited the increase in tumor volume without weight loss. In particular, the liposome formulation encapsulating Example 1 significantly inhibited the increase in tumor volume without weight loss.

TABLE 104

| | Dosing period (day) | Dose (Alvocidib conversion), Dosing schedule | T/C (%) | Weight loss |
|---|---|---|---|---|
| Liposome encapsulating Example 1 | 13 | 50 mg/ kg × 4 (twice/week) | 33 | not observed |
| Liposome encapsulating Example 2 | 13 | 50 mg/ kg × 4 (twice/week) | 51 | not observed |
| Liposome encapsulating Example 5 | 13 | 50 mg/kg, single dose (rest after one administration) | 67 | observed |
| Liposome encapsulating Example 6 | 13 | 50 mg/kg × 1, 37.5 mg/kg × 2 | 58 | observed |

The present disclosure relates to prodrugs of Alvocidib. When attempting to encapsulate Alvocidib in liposomes, the present inventors found a problem in that Alvocidib was unexpectedly immediately released from the liposomes. The present inventors have conducted intensive studies in an attempt and found that the compounds of formula (1), formula (1'), formula (1A) and formula (1A') can solve the above problem, and particularly, the compounds represented by formula (1A) or formula (1A') have exceptional and heterogeneous effects, that is, it exhibits excellent anti-tumor activity and not cause weight loss as a side effect. These findings resulted in the completion of the present disclosure.

Specifically, the present inventors found that, in particular, a series of the compounds represented by formula (1A) or formula (1A') have the characteristics of being stable under acidic conditions while being rapidly degraded under neutral conditions, and therefore, they have the exceptionally remarkable effects as a pharmaceutical formulation, that is, they can be stored stably, and can be rapidly degraded and converted to Alvocidib in the blood. The compounds described in Patent Documents 2 or 3 were unstable in a buffer solution of pH 5 and were not converted to the activated form at pH 7.4, and the above exceptionally remarkable effects were not observed in these compounds (Experimental Example 1). The compound described in Patent Document 3 had a problem with solution stability. On the other hand, in particular, a series of the compounds represented by Formula (1A) or Formula (1A') were stable in solution (Experimental Example 2).

In particular, a series of the compounds represented by formula (1A) or formula (1A') were rapidly converted to Alvocidib in human and mouse plasma without difference between species (Experimental Example 3). On the other hand, the compound described in Patent Document 2 was not efficiently converted to the activated form in human plasma.

In particular, a series of the compounds represented by formula (1A) or formula (1A') were efficiently encapsulated in liposomes (Experimental Example 4), the liposome formulations were stable (Experimental Example 5), and showed higher blood retention (Experimental Example 6). On the other hand, the compound described in Patent Document 2 was unstable in the liposome formulation.

In particular, the liposome formulations of a series of the compounds represented by formula (1A) or formula (1A') exhibited the exceptionally remarkable effect, that is, they significantly inhibited the increase in tumor volume in a in vivo mouse model (Experimental Examples 7 and 8). Among the compounds represented by formula (1A) or formula (1A'), Examples 1 and 2 exhibited the exceptionally remarkable effect and heterogeneous effect, that is, they significantly inhibited the increase in tumor volume without weight loss in a in vivo mouse model (Experimental Example 8), leading to the completion of this invention.

The present invention enables administration over a relatively short period of time, rather than continuous administration over a long period of time, which places a heavy burden on patients, and can be expected to have significant anticancer effects while reducing side effects.

As shown above, the compounds of the present disclosure were shown to have exceptional anti-tumor effects.

Note

As described above, although the present disclosure has been illustrated using the preferable embodiments thereof, it is understood that the scope of the present disclosure should be interpreted only by the claims. This application claims priority to Japanese Patent Application No. 2021-135603 (filed on Aug. 23, 2021), and their contents are incorporated herein by reference in their entirety. It is understood that the patents, patent applications, scientific literature, and other documents cited herein should be incorporated by reference into this specification to the same extent as if the contents themselves were specifically set forth herein.

INDUSTRIAL APPLICABILITY

A pharmaceutical composition comprising an Alvocidib prodrug, a pharmaceutically acceptable salt thereof, or a hydrate or solvate thereof exhibits excellent conversion efficiency to Alvocidib, storage stability, encapsulation efficiency in liposomes, and blood retention by introducing a side chain having a specific structure to Alvocidib. Furthermore, the drug released from the liposomes is rapidly converted to Alvocidib, thereby exhibiting its medicinal efficacy. Therefore, the compound of the present disclosure is extremely useful because it can expand the use of Alvocidib, whose use as a liposome formulation is limited, due to its rapid release from liposomes.

The invention claimed is:

1. A compound represented by of formula (1):

(1)

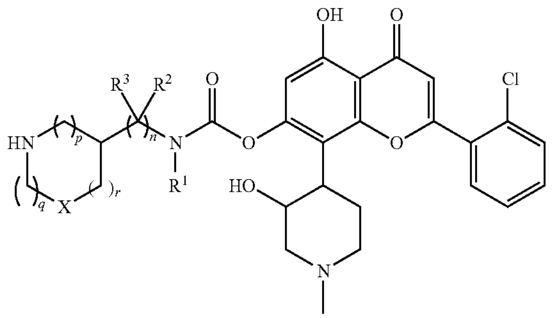

or a pharmaceutically acceptable salt thereof, wherein $R^1$ is an optionally substituted $C_{1-6}$ alkyl group, $R^2$ and $R^3$ are the same or different, each independently a hydrogen atom or an optionally substituted $C_{1-6}$ alkyl group, X is $CH_2$ or an oxygen atom, n is 1 or 2, p is 0, 1 or 2, q is 1 or 2, and r is 0, 1 or 2, wherein, if X is an oxygen atom, q is 2.

2. The compound of claim 1, which has a structure of formula (1'):

(1')

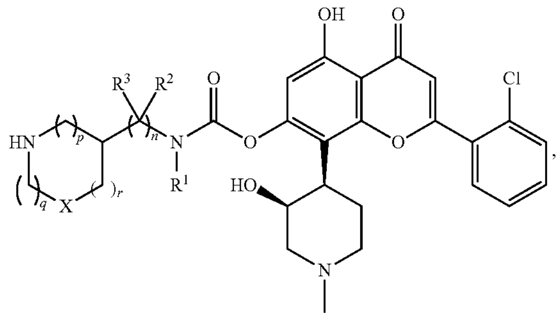

or a pharmaceutically acceptable salt thereof.

3. The compound of claim 1, wherein the optionally substituted $C_{1-6}$ alkyl groups in $R^1$, $R^2$, and $R^3$ are each independently a $C_{1-6}$ alkyl group optionally substituted with 1 to 5 of the same or different substituents independently selected from the group consisting of:

(1) a halogen atom, (2) a hydroxyl group, (3) a carboxyl group, (4) a sulfinic acid group, (5) a sulfonic acid group, (6) a phosphoric acid group, (7) an optionally substituted $C_{3-8}$ cycloalkyl group, (8) an optionally substituted $C_{6-10}$ aryl group, (9) an optionally substituted 5- to 10-membered heteroaryl group,

(10) an optionally substituted $C_{1-6}$ alkoxy group,

(11) an optionally substituted $C_{3-10}$ cycloalkoxy group,

(12) an optionally substituted $C_{1-6}$ alkoxycarbonyl group,

(13) an optionally substituted $C_{1-6}$ alkylcarbonyl group,

(14) an optionally substituted 3- to 10-membered saturated heterocyclic group,

(15) $—NR^4R^5$,

(16) $—CO_2R^4$,

(17) a guanidine group,

(18) $—CONR^4R^5$,

(19) $—SO_2R^4$,

(20) $—SO_2NR^4R^5$, and

(21) cyano, wherein the substituents in (7), (8), (9), (10), (11), (12), (13), and (14) are groups which are optionally substituted with 1 to 5 of the same or different substituents selected from the group consisting of:

(a) a halogen atom, (b) a hydroxyl group, (c) a $C_{1-6}$ alkyl group, (d) a $C_{1-6}$ alkoxy group, (e) a cyano group, (f) a carboxyl group, (g) a sulfinic acid group, (h) a sulfonic acid group, (i) a phosphoric acid group, (j) a $C_{1-6}$ alkoxycarbonyl group, (k) a $C_{1-6}$ alkylcarbonyl group, (l) $—NR^4R^5$, (m) $—CO_2R^4$, (n) a guanidine group, (o) $—CONR^4R^5$, (p) $—SO_2R^4$, and (q) $—SO_2NR^4R^5$, and $R^4$ and $R^5$ are the same or different hydrogen atoms or $C_{1-6}$ alkyl groups, or a pharmaceutically acceptable salt thereof.

4. The compound of claim 1, wherein p is 0, or a pharmaceutically acceptable salt thereof.

5. The compound of claim 1, wherein r is 2, or a pharmaceutically acceptable salt thereof.

6. The compound of claim 1, wherein $R^2$ and $R^3$ are the same or different, each independently (1) a hydrogen atom, or (2) a $C_{1-6}$ alkyl group, which is optionally substituted with 1 to 3 of the same or different, each substituent is independently selected from the group consisting of a fluorine atom and $C_{1-6}$ alkoxy, or a pharmaceutically acceptable salt thereof.

7. The compound of claim 1, wherein $R^2$ and $R^3$ are hydrogen atoms, or a pharmaceutically acceptable salt thereof.

8. The compound of claim 1, wherein X is $CH_2$, or a pharmaceutically acceptable salt thereof.

9. The compound of claim 8, which has a structure of formula (1A):

(1A)

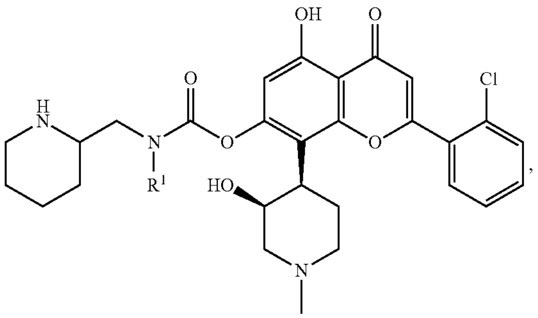

or a pharmaceutically acceptable salt thereof.

10. The compound of claim 9, which has a structure of formula (1A'):

(1A')

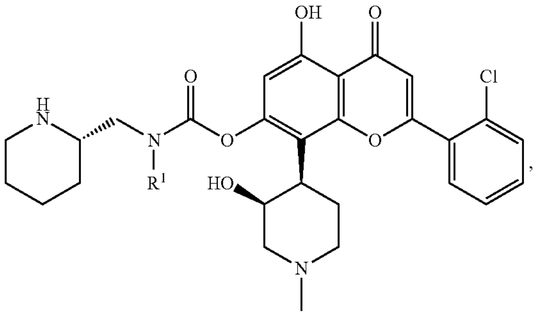

or a pharmaceutically acceptable salt thereof.

11. The compound of claim 1, wherein $R^1$ is a $C_{1-6}$ alkyl group, which is optionally substituted with 1 to 3 of the same or different, each substituent is independently selected from the group consisting of a halogen atom, a $C_{6-10}$ aryl group, a hydroxyl group, a carboxyl group, a sulfinic acid group, a sulfonic acid group, a phosphoric acid group, $C_{1-6}$ alkoxy, $—NR^4R^5$, $—CO_2R^4$, $—CONR^4R^5$, $—SO_2R^4$, and $—SO_2NR^4R^5$, or a pharmaceutically acceptable salt thereof.

12. The compound of claim 1, wherein $R^1$ is an ethyl group, or a pharmaceutically acceptable salt thereof.

13. The compound of claim 1, which is 2-(2-chlorophenyl)-5-hydroxy-8-[(3S,4R)-3-hydroxy-1-methylpiperidin-4-yl]-4-oxo-4H-1-benzopyran-7-yl ethyl {[(2S)-piperidin-2-yl]methyl}carbamate, 2-(2-chlorophenyl)-5-hydroxy-8-[(3S,4R)-3-hydroxy-1-methylpiperidin-4-yl]-4-oxo-4H-1-benzopyran-7-yl ethyl {[(2R)-piperidin-2-yl]methyl}carbamate, 2-(2-chlorophenyl)-5-hydroxy-8-[(3S,4R)-3-hydroxy-1-methylpiperidin-4-yl]-4-oxo-4H-1-benzopyran-7-yl methyl {[(2S)-piperidin-2-yl]methyl}carbamate, 2-(2-chlorophenyl)-5-hydroxy-8-[(3S,4R)-3-hydroxy-1-methylpiperidin-4-yl]-4-oxo-4H-1-benzopyran-7-yl methyl {[(2R)-piperidin-2-yl]methyl}carbamate, 2-(2-chlorophenyl)-5-hydroxy-8-[(3S,4R)-3-hydroxy-1-methylpiperidin-4-yl]-4-oxo-4H-1-benzopyran-7-yl {[(2S)-piperidin-2-yl]methyl}propylcarbamate, 2-(2-chlorophenyl)-5-hydroxy-8-[(3S,4R)-3-hydroxy-1-methylpiperidin-4-yl]-4-oxo-4H-1-benzopyran-7-yl {[(2R)-piperidin-2-yl]methyl}propylcarbamate, 2-(2-chlorophenyl)-5-hydroxy-8-[(3S,4R)-3-hydroxy-1-methylpiperidin-4-yl]-4-oxo-4H-1-benzopyran-7-yl ethyl[(piperidin-2-yl)methyl]carbamate, 2-(2-chlorophenyl)-5-hydroxy-8-[(3S,4R)-3-hydroxy-1-methylpiperidin-4-yl]-4-oxo-4H-1-benzopyran-7-yl methyl[(piperidin-2-yl)methyl]carbamate, 2-(2-chlorophenyl)-5-hydroxy-8-[(3S,4R)-3-hydroxy-1-methylpiperidin-4-yl]-4-oxo-4H-1-benzopyran-7-yl [(piperidin-2-yl)methyl]propylcarbamate, 2-(2-chlorophenyl)-5-hydroxy-8-[(3S,4R)-3-hydroxy-1-methylpiperidin-4-yl]-4-oxo-4H-1-benzopyran-7-yl [(piperidin-2-yl)methyl]propan-2-ylcarbamate, 2-(2-chlorophenyl)-5-hydroxy-8-[(3S,4R)-3-hydroxy-1-methylpiperidin-4-yl]-4-oxo-4H-1-benzopyran-7-yl (2-fluoroethyl) [(piperidin-2-yl)methyl]carbamate, 2-(2-chlorophenyl)-5-hydroxy-8-[(3S,4R)-3-hydroxy-1-methylpiperidin-4-yl]-4-oxo-4H-1-benzopyran-7-yl (2-methoxyethyl) [(piperidin-2-yl)methyl]carbamate, 2-(2-chlorophenyl)-5-hydroxy-8-[(3S,4R)-3-hydroxy-1-methylpiperidin-4-yl]-4-oxo-4H-1-benzopyran-7-yl [(piperidin-2-yl)methyl](3,3,3-trifluoropropyl) carbamate, 2-(2-chlorophenyl)-5-hydroxy-8-[(3S,4R)-3-hydroxy-1-methylpiperidin-4-yl]-4-oxo-4H-1-benzopyran-7-yl [(piperidin-2-yl)methyl](4,4,4-trifluorobutyl) carbamate, 2-(2-chlorophenyl)-5-hydroxy-8-[(3S,4R)-3-hydroxy-1-methylpiperidin-4-yl]-4-oxo-4H-1-benzopyran-7-yl benzyl[(piperidin-2-yl)methyl]carbamate, 2-(2-chlorophenyl)-5-hydroxy-8-[(3S,4R)-3-hydroxy-1-methylpiperidin-4-yl]-4-oxo-4H-1-benzopyran-7-yl ethyl[2-(piperidin-2-yl)ethyl]carbamate, 2-(2-chlorophenyl)-5-hydroxy-8-[(3S,4R)-3-hydroxy-1-methylpiperidin-4-yl]-4-oxo-4H-1-benzopyran-7-yl methyl {[(3R)-morpholin-3-yl]methyl}carbamate, 2-(2-chlorophenyl)-5-hydroxy-8-[(3S,4R)-3-hydroxy-1-methylpiperidin-4-yl]-4-oxo-4H-1-benzopyran-7-yl ethyl[(pyrrolidin-2-yl)methyl]carbamate, 2-(2-chlorophenyl)-5-hydroxy-8-[(3S,4R)-3-hydroxy-1-methylpiperidin-4-yl]-4-oxo-4H-1-benzopyran-7-yl methyl {1-[(2R)-piperidin-2-yl]ethyl}carbamate, 2-(2-chlorophenyl)-5-hydroxy-8-[(3S,4R)-3-hydroxy-1-methylpiperidin-4-yl]-4-oxo-4H-1-benzopyran-7-yl methyl {1-[(2S)-piperidin-2-yl]ethyl}carbamate, 2-(2-chlorophenyl)-5-hydroxy-8-[(3S,4R)-3-hydroxy-1-methylpiperidin-4-yl]-4-oxo-4H-1-benzopyran-7-yl ethyl[(piperidin-3-yl)methyl]carbamate, or 2-(2-chlorophenyl)-5-hydroxy-8-[(3S,4R)-3-hydroxy-1-methylpiperidin-4-yl]-4-oxo-4H-1-benzopyran-7-yl ethyl[(pyrrolidin-3-yl)methyl]carbamate, or a pharmaceutically acceptable salt thereof.

14. The compound of claim 1, which is 2-(2-chlorophenyl)-5-hydroxy-8-[(3S,4R)-3-hydroxy-1-methylpiperidin-4-yl]-4-oxo-4H-1-benzopyran-7-yl ethyl {[(2S)-piperidin-2-yl]methyl}carbamate, or a pharmaceutically acceptable salt thereof.

15. A composition, comprising:

the compound of claim 1 or a pharmaceutically acceptable salt thereof.

16. A liposome, comprising:

the compound of claim 1 or a pharmaceutically acceptable salt thereof.

17. A composition, comprising:

a liposome encapsulating the compound of claim 1 or a pharmaceutically acceptable salt thereof.

18. The composition of claim 17, wherein the liposome comprises a phospholipid, and the compound of claim 1 or a pharmaceutically acceptable salt thereof.

19. The composition of claim 18, wherein the phospholipid comprises at least one selected from the group consisting of phosphatidylcholine, phosphatidylglycerol, phosphatidic acid, phosphatidylethanolamine, phosphatidylserine, phosphatidylinositol, sphingomyelin, soybean lecithin, egg yolk lecithin, hydrogenated egg yolk lecithin, and hydrogenated soybean lecithin.

20. The composition of claim 17, wherein the liposome further comprises a sterol.

21. The composition of claim 20, wherein the sterol is a cholesterol.

22. The composition of claim 17, wherein the liposome further comprises a polymer-modified lipid.

23. The composition of claim 22, wherein the polymer-modified lipid has a polymer moiety which is polyethylene glycol, polypropylene glycol, polyvinyl alcohol, polyvinylpyrrolidone, methoxypolyethylene glycol, methoxypolypropylene glycol, methoxypolyvinyl alcohol, methoxypolyvinylpyrrolidone, ethoxypolyethylene glycol, ethoxypolypropylene glycol, ethoxypolyvinyl alcohol, ethoxypolyvinylpyrrolidone, propoxypolyethylene glycol, propoxypolypropylene glycol, propoxypolyvinyl alcohol, or propoxypolyvinylpyrrolidone.

24. The composition of claim 22, wherein the polymer-modified lipid has a lipid moiety which is phosphatidylethanolamine or diacylglycerol.

25. The composition of claim 17, wherein the liposome further comprises at least one additive selected from the group consisting of an inorganic acid, an inorganic acid salt, an organic acid, an organic acid salt, a saccharide, buffer, an antioxidant, and a polymer.

26. A method for treating cancer in a subject in need thereof, comprising:

administering to the subject a therapeutically and/or prophylactically effective amount of the compound of claim 1 or a pharmaceutically acceptable salt thereof.

27. The method of claim 26, wherein the cancer is at least one selected from the group consisting of acute leukemia, chronic lymphocytic leukemia, chronic myelogenous leukemia, polycythemia vera, malignant lymphoma, plasma cell tumor, multiple myeloma, myelodysplastic syndrome, brain tumor, head and neck cancer, esophageal cancer, thyroid cancer, small cell lung cancer, non-small cell lung cancer, thymoma/thymic carcinoma, breast cancer, gastric cancer, gallbladder/bile duct cancer, liver cancer, hepatocellular carcinoma, pancreatic cancer, colon cancer, rectal cancer, anal cancer, gastrointestinal stromal tumor, choriocarcinoma, endometrial cancer, cervical cancer, ovarian cancer, bladder cancer, prostate cancer, urothelial cancer, renal cancer, renal cell cancer, testicular tumor, testicular germ cell tumor, ovarian germ cell tumor, Wilms tumor, skin cancer, malignant melanoma, neuroblastoma, osteosarcoma, Ewing sarcoma, and soft tissue sarcoma.

28. A combination, comprising:

the compound of claim 1 or a pharmaceutically acceptable salt thereof; and a concomitantly used medicament or a pharmaceutically acceptable salt thereof, wherein the concomitantly used medicament is at least one selected from the group consisting of a hormonal therapy agent, a chemotherapeutic agent, an immunotherapeutic agent, and an agent that inhibits a cell growth factor and a receptor action thereof.

29. A compound, which is 2-(2-chlorophenyl)-5-hydroxy-8-[(3S,4R)-3-hydroxy-1-methylpiperidin-4-yl]-4-oxo-4H-1-benzopyran-7-yl ethyl {[(2S)-piperidin-2-yl] methyl}carbamate ditrifluoroacetate.

30. A method for treating cancer in a subject in need thereof, comprising: administering to the subject a therapeutically and/or prophylactically effective amount of the compound of claim 29.

31. A composition, comprising: a liposome encapsulating the compound of claim 29.

32. A method for treating cancer in a subject in need thereof, comprising: administering to the subject a therapeutically and/or prophylactically effective amount of the compound of claim 14 or a pharmaceutically acceptable salt thereof.

33. A method for treating cancer in a subject in need thereof, comprising: administering to the subject a therapeutically and/or prophylactically effective amount of the liposome of claim 16.

* * * * *